(12) United States Patent
De Block et al.

(10) Patent No.: US 7,851,675 B2
(45) Date of Patent: Dec. 14, 2010

(54) STRESS RESISTANT PLANTS

(75) Inventors: Marc De Block, Merelbeke (BE); Michael Metzlaff, Tervuren (BE); Veronique Gossele, Ghent (BE)

(73) Assignee: Bayer Bioscience N.V., Ghent (BE)

( * ) Notice: Subject to any disclaimer, the term of this patent is extended or adjusted under 35 U.S.C. 154(b) by 498 days.

(21) Appl. No.: 11/663,657

(22) PCT Filed: Sep. 16, 2005

(86) PCT No.: PCT/EP2005/010168

§ 371 (c)(1),
(2), (4) Date: Mar. 23, 2007

(87) PCT Pub. No.: WO2006/032469

PCT Pub. Date: Mar. 30, 2006

(65) Prior Publication Data

US 2007/0300322 A1      Dec. 27, 2007

Related U.S. Application Data

(60) Provisional application No. 60/628,826, filed on Nov. 17, 2004.

(30) Foreign Application Priority Data

Sep. 24, 2004  (EP) ................................. 04077624

(51) Int. Cl.
C12N 15/82 (2006.01)
C12N 15/31 (2006.01)
A01H 5/00 (2006.01)
A01H 5/10 (2006.01)

(52) U.S. Cl. .................... 800/289; 435/320.1; 435/419; 800/298; 800/314; 800/306; 800/320.3; 800/320.1; 800/320; 800/322; 800/320.2; 800/312; 800/305; 800/317.4; 800/317.3; 800/317.2

(58) Field of Classification Search ....................... None
See application file for complete search history.

(56) References Cited

U.S. PATENT DOCUMENTS 5,792,921 A * 8/1998 Londesborough et al. ... 800/284
2005/0267023 A1* 12/2005 Sinclair et al. ................ 514/12

FOREIGN PATENT DOCUMENTS

| JP | 2004-261136 | | 9/2004 |
|---|---|---|---|
| WO | WO 89/03887 | | 5/1989 |
| WO | WO 89/10396 | | 11/1989 |
| WO | WO 92/13956 | | 8/1992 |
| WO | WO 96/06932 | | 3/1996 |
| WO | WO 97/13865 | | 4/1997 |
| WO | WO 00/04173 | | 1/2000 |
| WO | WO 2004/016726 | | 2/2004 |
| WO | WO2004/016726 | * | 2/2004 |
| WO | WO 2004/090140 | | 10/2004 |

OTHER PUBLICATIONS

Hunt et al. NAD—new roles in signaling and gene regulation in plants. New Phytologist. Jul. 2004,vol. 163, No. 1, pp. 31-44.*
Wagner R. et al. The pyridine-nucleotide cycle in tobacco: enzyme activities for the recycling of NAD. Planta 1986, vol. 167 pp. 226-232.*
Yan Q. et al. The NAD+ precursors, nicotinic acid and nicotinamide upregulate glyceraldehyde-3-phosphate dehydrogenase and glucose-6-phosphate dehydrogenase mRNA in Jurkat cells Biochem Biophys Res Commun. Feb. 5, 1999;255(1):133-6.*
An, et al., "Conserved Expression of the Arabidopsis ACT1 and ACT3 Actin Subclass on Organ Primordia and Mature Pollen", The Plant Cell, vol. 8, p. 15-30, Jan. 1996.
Anderson, et al., "Nicotinamide and PNC1 Govern Lifespan extension by Calorie Restriction in *Saccharomyces cerevisiae*", Nature, vol. 423, p. 181-185, May 8, 2003.
EMBL BT002920 *Arabidopsis thalian* clone RAFL14-96-I10 (R20098) unknown protein (At5g23220) mRNA, complete cds. (Jan. 16, 2003).
EMBL AY093004 *Arabidopsis thaliana* unknown protein (At4g36940) mRNA, complete cds. (Apr. 22, 2002).
EMBL AY114544 *Arabidopsis thaliana* unknown protein (At5g55810) mRNA, complete cds. (Jun. 11, 2002).
EMBL BT010741 *Arabidopsis thaliana* At1g55090 gene, complete cds. (Nov. 20, 2003).
De Block, et al., "A simple and robust in vitro assay to quantify the vigour of oilseed rape lines and hybrids", Plant Physiol. Biochem., vol. 40, p. 845-852, 2002.
Gallo, et al., "Nicotinamide Clearance by Pnc1 Directly Regulates Sir2-Mediated Silencing and Longevity", Molecular and Cellular Biology, vol. 24, No. 3, p. 1301-1312, Feb. 2004.
Harpster, et al., "Relative Stengths of the 35S Califlower Mosiac Virus, 1', 2', and nopaline synthase promoters in transformed tobacco sugarbeet and oilseed rape callus tissue", Mol. Gen. Genet., vol. 212, p. 182-190, 1988.
Hudspeth, et al., "Structure and Expression of the Maize gene encoding the phosphoenolpyruvate carboxylase isozyme involved in $C_4$ photosynthesis", Plant Molecular Biology, vol. 12, p. 579-589, 1989.
Hunt, et al., NAD—new roles in signalling and gene regulation in plants, New Phytologist, vol. 163, p. 31-44, 2004.
Keil, et al., "Both Wound-inducible and tuber-specific expression are mediated by the promoter of a single member of the potato protinase II gene family,"The EMBO Journal, vol. 8, No. 5, p. 1323-1330, 1989.
Keller, et al., "Glycine-rich cell wall proteins in bean: gene structure and association of the protein with the vascular system", The EMBO Journal, vol. 7, No. 12, p. 3625-3633, 1988.

(Continued)

*Primary Examiner*—Cynthia Collins
(74) *Attorney, Agent, or Firm*—Hunton & Williams LLP

(57) ABSTRACT

Stress tolerance in plants and plant cells is achieved by using nucleotide sequences encoding enzymes involved in the NAD salvage synthesis pathway and/or the NAD de novo synthesis pathway e.g. for overexpression in plants.

14 Claims, 11 Drawing Sheets

OTHER PUBLICATIONS

Keller, et al., "Specific Expression of a Novel cell Wall hydroxyproline-rich glycoprotein gene in lateral root initiation", Genes & Development, vol. 3, p. 1639-1646, 1989.

Nakamura, et al., "Quantitation of intracellular NAD(P)H can monitor an imbalance of DNA single strand break repair in base excision repair deficient cells in real time", Nucleic Acids Research, vol. 31, No. 17, e104, 7 pages, 2003.

Peleman, et al., "Structure and expression analyses of the S-adenosylmethionine synthetase gene family in *Arabidopsis thaliana*", Gene, vol. 84, p. 359-369, 1989.

Uchimiya, et al., "Transgenic rice plants conferring increased tolerance to rice blast and multiple environmental stresses", Molecular Breeding, vol. 9, p. 25-31, 2002.

Uchimiya, et al., "Metabolic activation of NAD pathway down-regulated cell death leading to biotic and abiotic stress resistance", Poster Abstracts, Saturday, Apr. 12: Programmed Cell Death Development, p. 61, 2003.

Wang, et al., "Plant responses to drought, salinity and extreme temperatures: towards genetic engineering for stress tolerance", Planta, vol. 218, p. 1-14, 2003.

* cited by examiner

STRESS RESISTANT PLANTS

CROSS-REFERENCE TO RELATED APPLICATIONS

This application is a U.S. national stage application of International Application No. PCT/EP2005/010168, filed on Sep. 16, 2005, which claims the benefit of European Application No. EPO4077624.7, filed on Sep. 24, 2004 and U.S. Provisional Application Ser. No. 60/628,826, filed on Nov. 17, 2004, the disclosures of each of which are herein incorporated by reference in their entireties.

BACKGROUND OF THE INVENTION

Methods are provided for increasing the stress resistance in plants and plant cells whereby enzymes involved in the NAD salvage synthesis pathway and/or the NAD de novo synthesis pathway are expressed in plants.

BACKGROUND ART

Tolerance of plants to adverse growing conditions, including drought, high light intensities, high temperatures, nutrient limitations, saline growing conditions and the like, is a very desired property for crop plants, in view of the never-ending quest to ultimately increase the actual yield of these plants.

Various ways of achieving that goal of improving what is commonly known as the stress resistance or stress tolerance of plants have been described. Since different abiotic stress conditions frequently result in the generation of harmful reactive oxygen species ("ROS") such as superoxides or hydrogen peroxides, initial attempts to improve stress resistance in plants focused on prevention of the generation of the ROS or the removal thereof. Examples of these approaches are over-expression of ROS scavenging enzymes such as catalases, peroxidases, superoxide dismutases etc. or even increasing the amount of ROS scavenging molecules such as ascorbic acid, glutathione etc. These approaches and other attempts to engineer stress tolerant plants are reviewed e.g. in Wang et al. 2003, Planta 218:1-14.

Stress tolerance in plant cells and plants can also be achieved by reducing the activity or the level of the endogenous poly-ADP-ribose polymerases (ParP) or poly(ADP-ribose) glycohydrolases (ParG) as described in WO00/04173 and PCT/EP2004/003995, respectively. It is thought that in this way, fatal NAD and ATP depletion in plant cells subject to stress conditions, resulting in traumatic cell death, can be avoided or sufficiently postponed for the stressed cells to survive and acclimate to the stress conditions.

Uchimiya et al. (2002) et al. describe the isolation of a rice gene denoted YK1, as well as use of a chimeric YK1 gene to increase the tolerance of transgenic rice plants harboring that gene to rice blast and several abiotic stresses such as NaCl, UV—C, submergence, and hydrogen peroxide. (Uchimiya et al., 2002, Molecular breeding 9: 25-31).

Uchimiya et al. further published a poster abstract describing that overexpression of a NAD dependent reductase gene (YK1) in rice cells also promoted the level of NAD(P)(H) through up-regulating NAD synthetase activities, and concluded that this modification in turn generated a pool of redox substances needed for ROS stress resistance (Uchimiya et al. 2003 Keystone symposium on Plant biology: Functions and control of cell death, Snowbird Utah Apr. 10-15, 2003).

NAD synthetase from yeast has been well characterized and is the last enzyme in both the NAD de novo synthesis pathway and the NAD salvage pathway (see FIG. 1). In the de novo pathway, quinolate is the precursor for NAD synthesis and is generated as a product of tryptophan degradation. In the salvage pathway, nicotinamide (which is a degradation product of NAD, generated through the action of various enzymes such as PARP, NAD-dependent deacetylases or other NAD glycohydrolases) is the precursor molecule. In a first step, nicotinamide is deamidated to nicotinic cid by a nicotinamidase. The nicotinic acid is transferred to 5-phosphoribosyl-1-pyrophosphate by the enzyme nicotinate phosphoribosyl transferase to yield nicotinic acid mononucleotide. This compound is shared between the de novo and the salvage pathway. Hence, further conversion of this compound by NAD+ pyrophosphorylase and NAD synthetase is achieved as in the de novo pathway.

In yeast, overexpression of PNC1 (encoding nicotinamidase) has been correlated with life span extension by calorie restriction and low-intensity stress (Anderson et al., 2003 Nature 423: p 181-185; Gallo et al., 2004, Molecular and Cellular Biology 24: 1301-1312).

Little is known about the respective enzymes of the NAD biosynthesis pathways in plants. Hunt et al., 2004 describe the use of the available genomic information from *Arabidopsis* to identify the plant homologues of these enzymes (Hunt et al., 2004, New Phytologist 163(1): 31-44). The identified DNA sequences have the following Accession numbers: for nicotinamidase: At5g23220; At5g23230 and At3g16190; for nicotinate phosphoribosyltransferase: At4g36940, At2g23420, for nicotinic acid mononucleotide adenyltransferase: At5g55810 and for NAD synthetase: At1g55090 (all nucleotide sequences are incorporated herein by reference).

Alternative methods for increasing stress tolerance in plants are still required and the embodiments described hereinafter, including the claims, provide such methods and means.

SUMMARY OF THE INVENTION

In one embodiment of the invention, a method is provided for obtaining a plant with increased stress resistance comprising introducing a chimeric gene into a cells of a plant to obtain transgenic cells whereby the chimeric gene comprises the following operably linked DNA fragments:

i. A plant-expressible promoter;

ii. A DNA region coding for a plant-functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase;

iii. A 3' end region involved in transcription termination and polyadenylation, followed by regenerating the transgenic cells to obtain a population of transgenic plants; and selecting a plant from the population of transgenic plants which exhibits increased stress resistance or selecting a plant which exhibits a reduced level of reactive oxygen species or maintains a high level of NADH under stress conditions when compared to a similar non-transgenic plant. The DNA region may code for a protein comprising an amino acid sequence selected from the aminoacid sequence of SEQ ID No.:2, SEQ ID No.:4, SEQ ID No.:6; SEQ ID No.:8, SEQ ID No.:10, SEQ ID No.:12; SEQ ID No.:14; SEQ ID No.:16, SEQ ID No.:18, SEQ ID No.:20, SEQ ID No.: 22, SEQ ID No.:24 or a protein having about 60% sequence identity and having the enzymatic activity of nicotinamide adenine dinucleotide salvage synthesis pathway such as the nucleotide sequences of SEQ ID No.:1, SEQ ID No.:3, SEQ ID No.:5; SEQ ID No.:7, SEQ ID No.:9, SEQ ID No.:11; SEQ ID No.:13; SEQ ID No.:15, SEQ ID No.:17, SEQ ID No.:19, SEQ ID No.: 21 or SEQ ID No.:23.

In another embodiment, the invention relates to the chimeric genes as described herein, plant cells comprising these chimeric genes, and plants consisting essentially of plant cells comprising these chimeric genes, and seeds of such plants. These plants and plant cells may be characterized in that they have a lower level of reactive oxygen species under stress conditions than a similar plant not comprising such a chimeric gene.

In yet another embodiment, the invention relates to the use of the described chimeric genes to increase the stress resistance of a plant or to decrease the level of reactive oxygen species in a plant or a plant cell under stress conditions.

The invention further provides the use of a DNA sequence encoding a plant functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase, such as a a DNA sequence encoding a protein comprising an amino acid sequence selected from the aminoacid sequence of SEQ ID No.:2, SEQ ID No.:4, SEQ ID No.:6; SEQ ID No.:8, SEQ ID No.:10, SEQ ID No.:12; SEQ ID No.:14; SEQ ID No.:16, SEQ ID No.:18, SEQ ID No.:20, SEQ ID No.: 22, SEQ ID No.:24 or a protein having about 60% sequence identity and having the enzymatic activity of nicotinamide adenine dinucleotide salvage synthesis pathway, including a DNA sequence comprising an nucleotide sequence selected from the nucleotide sequence of SEQ ID No.:1, SEQ ID No.:3, SEQ ID No.:5; SEQ ID No.:7, SEQ ID No.:9, SEQ ID No.:11; SEQ ID No.:13; SEQ ID No.:15, SEQ ID No.:17, SEQ ID No.:19, SEQ ID No.:21 or SEQ ID No.:23, to increase the stress resistance of a plant or to decrease the level of reactive oxygen species or maintain the level of NADH in a plant or a plant cell under stress conditions.

DETAILED DESCRIPTION

Figure 1:
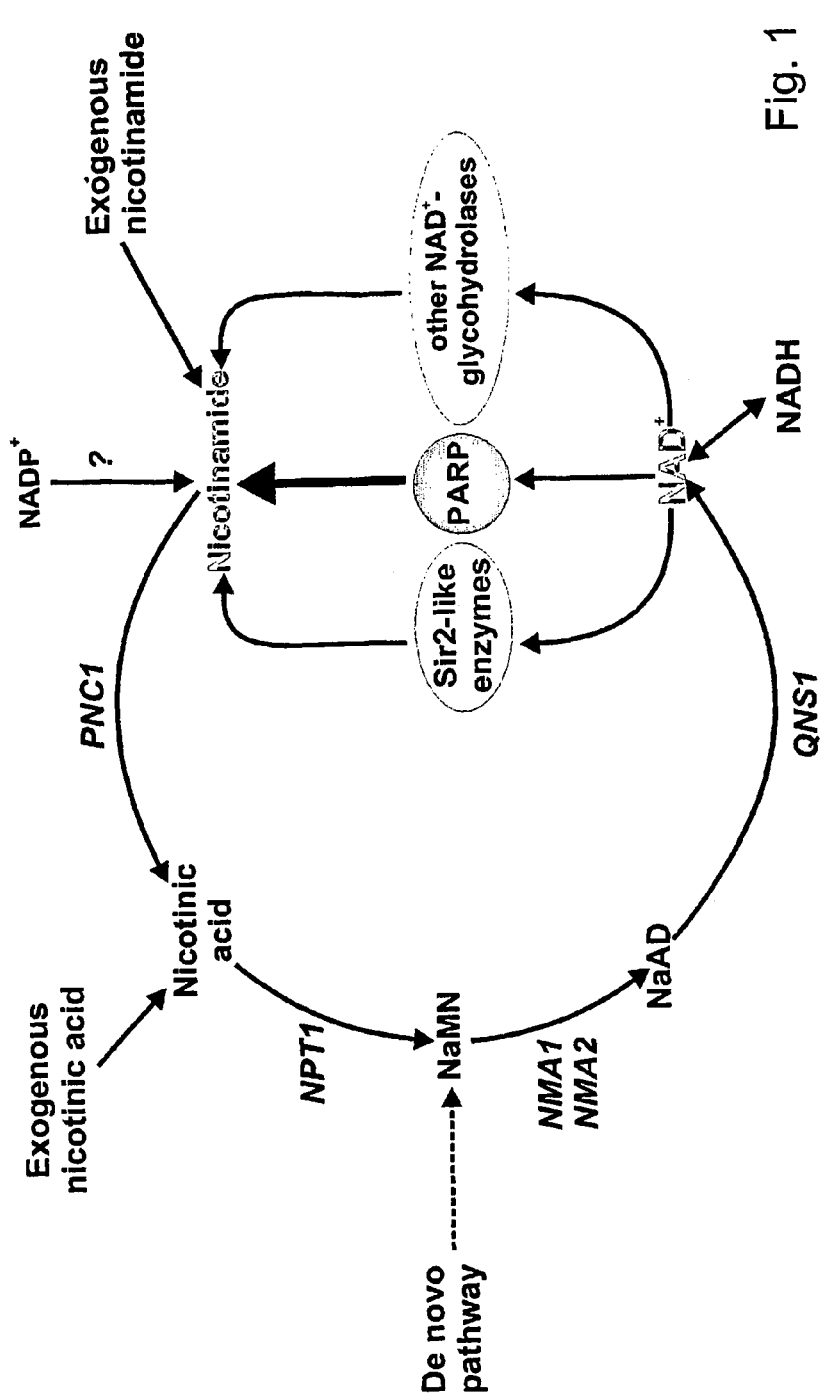
FIG. 1 is a schematic representation of the NAD salvage pathway and the de novo NAD synthesis pathway as known in baker's yeast (*Saccharomyces cerevisea*)

The current invention is based on the finding that DNA sequences encoding plant-functional enzymes from the NAD salvage pathway in yeasts could be used to obtain transgenic plants which were more resistant to stress, particularly abiotic stress, than plants not comprising these DNA sequences. The transgenic plants also exhibited a significantly reduced level of reactive oxygen species ("ROS") and maintained a high level of NADH, when put under stress conditions, compared to control plants Thus in one embodiment of the invention, a method is provided to obtain a plant with increased stress resistance, whereby the method comprises the steps of introducing a stress resistant chimeric gene as herein described into cells of a plant to obtain cells comprising the stress resistant chimeric gene;

regenerating these cells comprising the stress resistant chimeric gene to obtain a population of plants comprising the stress resistant chimeric gene; and selecting a plant from the population of these plants which exhibits increased stress resistance and/or decreased ROS level under stress conditions and/or maintains a high level of NADH, when compared to a similar non-transgenic plant.

The stress resistant chimeric gene thereby comprises a plant-expressible promoter operably linked to a DNA region coding for a plant-functional enzyme of the nicotinamide adenine dinucleotide salvage synthesis pathway selected from nicotinamidase, nicotinate phosphoribosyltransferase, nicotinic acid mononucleotide adenyl transferase or nicotinamide adenine dinucleotide synthetase and a 3' end region involved in transcription termination and polyadenylation.

As used herein, "a plant-functional enzyme of the nicotinamide adenine dinucleotide salvage synthesis pathway" is an enzyme which when introduced into plants, linked to appropriate control elements such as plant expressible promoter and terminator region, can be transcribed and translated to yield a enzyme of the NAD salvage synthesis pathway functional in plant cells. Included are the enzymes (and encoding genes) from the NAD salvage synthesis, which are obtained from a plant source, but also the enzymes obtained from yeast (*Saccharomyces cereviseae*) or from other yeasts or fungi. It is thought that the latter proteins may be even more suitable for the methods according to the invention, since these are less likely to be subject to the enzymatic feedback regulation etc. to which similar plant-derived enzymes may be subject.

Enzymes involved in the NAD salvage synthesis pathway comprise the following

Nicotinamidase (EC 3.5.1.19) catalyzing the hydrolysis of the amide group of nicotinamide, thereby releasing nicotinate and NH3. The enzyme is also known as nicotinamide deaminase, nicotinamide amidase, YNDase or nicotinamide amidohydrolase Nicotinate phophoribosyltransferase (EC 2.4.2.11) also known as niacin ribonucleotidase, nicotinic acid mononucleotide glycohydrolase; nicotinic acid mononucleotide pyrophosphorylase; nicotinic acid phosphoribosyltransferase catalyzing the following reaction

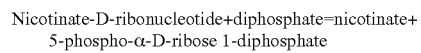

Nicotinate-D-ribonucleotide+diphosphate=nicotinate+
5-phospho-α-D-ribose 1-diphosphate Nicotinate-nucleotide adenylyltransferase, (EC 2.7.7.18) also known as deamido-NAD+ pyrophosphorylase; nicotinate mononucleotide adenylyltransferase; deamindonicotinamide adenine dinucleotide pyrophosphorylase; NaMT-ATase; nicotinic acid mononucleotide adenylyltransferase catalyzing the following reaction ATP+nicotinate ribonucleotide=diphosphate+deamido-NAD+

NAD-synthase (EC 6.3.1.5) also known as NAD synthetase; NAD+ synthase; nicotinamide adenine dinucleotide synthetase; diphosphopyridine nucleotide synthetase, catalyzing the following reaction Deamido-NAD++ATP+NH3=AMP+diphosphate+NAD+

In one embodiment of the invention, the coding regions encoding the different enzymes of the NAD salvage pathway comprise a nucleotide sequence encoding proteins with the amino acid sequences as set forth in SEQ ID Nos 2, 4, 6, 8 or 10, such as the nucleotide sequences of SEQ ID Nos 1, 3, 5, 7 or 9.

However, it will be clear that variants of these nucleotide sequences, including insertions, deletions and substitutions thereof may be also be used to the same effect. Equally, homologues to the mentioned nucleotide sequences from species different from *Saccharomyces cerevisea* can be used. These include but are not limited to nucleotide sequences from plants, and nucleotide sequences encoding proteins with the same amino acid sequences, as well as variants of such nucleotide sequences. Examples of the latter are nucleotide sequences encoding a protein with an amino acid sequence as set forth in SEQ ID Nos 12, 14, 16, 18, 20, 22 or 24 such as the nucleotide sequences of SEQ ID Nos 11, 13, 15, 17, 19, 21 or 23.

Variants of the described nucleotide sequence will have a sequence identity which is preferably at least about 80%, or 85 or 90% or 95% with identified nucleotide sequences encoding enzymes from the NAD salvage pathway, such as the ones identified in the sequence listing. Preferably, these variants will encode functional proteins with the same enzymatic activity as the enzymes from the NAD salvage pathway. For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Nucleotide sequences homologous to the nucleotide sequences encoding an enzyme from the NAD salvage pathway in yeast, or encoding a homologous enzyme from an organism different than yeast may be identified by in silico analysis of genomic data, as described by Hunt et al. (vide supra).

Homologous nucleotide sequence may also be identified and isolated by hybridization under stringent conditions using as probes identified nucleotide sequences encoding enzymes from the NAD salvage pathway, such as the ones identified in the sequence listing.

"Stringent hybridization conditions" as used herein means that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared carrier DNA such as salmon sperm DNA, followed by washing the hybridization support in 0.1×SSC at approximately 65° C., preferably twice for about 10 minutes. Other hybridization and wash conditions are well known and are exemplified in Sambrook et al, Molecular Cloning: A Laboratory Manual, Second Edition, Cold Spring Harbor, N.Y. (1989), particularly chapter 11.

Such variant sequences may also be obtained by DNA amplification using oligonucleotides specific for genes encoding enzymes from the NAD salvage pathway as primers, such as but not limited to oligonucleotides comprising about 20 to about 50 consecutive nucleotides selected from the nucleotide sequences of SEQ ID Nos 1, 3, 5, 7, 9, 11, 13, 15, 17, 19, 21, 23 or their complement.

The methods of the invention can be used to obtain plants tolerant to different kinds of stress-inducing conditions, particularly abiotic stress conditions including submergence, high light conditions, high UV radiation levels, increased hydrogen peroxide levels, drought conditions, high or low temperatures, increased salinity conditions. The methods of the invention can also be used to reduce the level of ROS in the cells of plants growing under adverse conditions, particularly abiotic stress conditions including submergence, high light conditions, high UV radiation levels, increased hydrogen peroxide levels, drought conditions, high or low temperatures, increased salinity conditions etc. The level of ROS or the level of NADH can be determined using the methods known in the art, including those described in Example 3.

Using the methods described herein, plants may be obtained wherein the level of ROS is equal to or lower than in control plants under non-stressed conditions, such as but not limited to low light. In these plants, under non-stressed conditions, the level of ROS may range from 50% to 100% of the level of control plants under low light conditions, more particularly from about 60% to about 85%. The level of the ROS in these plants under stress conditions is about 50% to 80% of the level of ROS in control plants under stress conditions, corresponding to about 60 to 80% of the level of ROS in control plants under non-stressed conditions. Similarly, the NADH level in these plants is equal to or higher than in control plants under non-stressed conditions, such as but not limited to low light. In these plants, under non-stressed conditions, the level of NADH may range from 100% to 160% of the level of NADH in control plants under low light conditions, more particularly from about 120% to about 140%. The level of NADH in these plants under stress conditions is about 200 to 300% of the level of NADH in control plants under stress conditions, corresponding to about 100 to 160% of the level of ROS in control plants under non-stressed conditions.

Methods to obtain transgenic plants are not deemed critical for the current invention and any transformation method and regeneration suitable for a particular plant species can be used. Such methods are well known in the art and include *Agrobacterium*-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. The transformed cells obtained in this way may then be regenerated into mature fertile plants.

The obtained transformed plant can be used in a conventional breeding scheme to produce more transformed plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

It will be clear that the different stress resistant chimeric genes described herein, with DNA regions encoding different enzymes from the NAD salvage pathway can be combined within one plant cell or plant, to further enhance the stress tolerance of the plants comprising the chimeric genes. Thus, in one embodiment of the invention, plant cells and plants are provided which comprise at least two stress resistant chimeric genes each comprising a different coding region.

The transgenic plant cells and plant lines according to the invention may further comprise chimeric genes which will reduce the expression of endogenous PARP and/or PARG genes as described in WO 00/04173 and PCT/EP2004/003995. These further chimeric genes may be introduced e.g. by crossing the transgenic plant lines of the current invention with transgenic plants containing PARP and/or PARG gene expression reducing chimeric genes. Transgenic plant cells or plant lines may also be obtained by introducing or transforming the chimeric genes of the invention into transgenic plant cells comprising the PARP or PARG gene expression reducing chimeric genes or vice versa.

For the purpose of the invention, the promoter is a plant-expressible promoter. As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al., 1988 *Mol. Gen. Genet* 212, 182-190), the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al., 1996, *The Plant Cell* 8, 15-30), stem-specific promoters (Keller et al., 1988, *EMBO J.* 7, 3625-3633), leaf specific promoters (Hudspeth et al., 1989, *Plant Mol Biol* 12, 579-589), mesophyl-specific promoters (such as the light-inducible Rubisco promoters), root-specific promoters (Keller et al., 1989, *Genes Devel.* 3, 1639-1646), tuber-specific promoters (Keil et al., 1989, *EMBO J.* 8, 1323-1330), vascular tissue specific promoters (Peleman et al., 1989, *Gene* 84, 359-369), stamen-selective promoters (WO 89/10396, WO 92/13956), dehiscence zone specific promoters (WO 97/13865) and the like.

The chimeric genes of the inventions may also be equipped with a nuclear localization signal ("NLS") functional in plants, operably linked to the DNA region encoding an enzyme of the NAD salvage pathway such as the SV40 NLS.

Having read this document, a person skilled in the art will immediately realize that similar effects with regard to increased stress resistance can be obtained whenever natural variants of plants are obtained wherein the endogenous genes coding for NAD salvage pathway enzymes are more active or expressed at a higher level. Such variant plants can be obtained by subjecting a population of plants to mutagenesis, such as, but not limited to EMS mutagenesis, followed by a screening for an increased activity of any one of the NAD salvage pathway enzymes, or a combination thereof.

It will also be immediately clear that a population of different varieties or cultivars can be screened for increased tolerance to the above mentioned stress conditions in general or particular selected abiotic stresses, followed by a correlation of the increased tolerance to stress conditions with the presence of a particular allele of any of the endogenous genes encoding an enzyme of the NAD salvage pathway enzyme. Such alleles can than be introduced into a plant of interest by crossing, if the species are sexually compatible, or they may be identified using conventional techniques as described herein (including hybridization or PCR amplification) and introduced using recombinant DNA technology. Introduction of particularly desired alleles using breeding techniques may be followed using molecular markers specific for the alleles of interest.

The methods and means described herein are believed to be suitable for all plant cells and plants, both dicotyledonous and monocotyledonous plant cells and plants including but not limited to cotton, *Brassica* vegetables, oilseed rape, wheat, corn or maize, barley, sunflowers, rice, oats, sugarcane, soybean, vegetables (including chicory, lettuce, tomato), tobacco, potato, sugarbeet, papaya, pineapple, mango, *Arabidopsis thaliana*, but also plants used in horticulture, floriculture or forestry.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

The following non-limiting Examples describe the construction of chimeric genes to increase stress resistance in plant cells and plants and the use of such genes.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:

SEQ ID No. 1: nucleotide sequence of the nicotinamidase from *Saccharomyces cereviseae* (PNC1).

SEQ ID No. 2: amino acid sequence of the nicotinamidase from *Saccharomyces cereviseae* (PNC1).

SEQ ID No. 3: nucleotide sequence of the nicotinate phosphoribosyltransferase from *Saccharomyces cereviseae* (NPT1) (complement)

SEQ ID No. 4: amino acid sequence of the nicotinate phosphoribosyltransferase from *Saccharomyces cereviseae* (NPT1)

SEQ ID No. 5: nucleotide sequence of the nicotinic acid mononucleotide adenyl transferase 1 (NMA1) from *Saccharomyces cereviseae*.

SEQ ID No. 6: amino acid sequence of the nicotinic acid mononucleotide adenyl transferase 1 (NMA1) from *Saccharomyces cereviseae*

SEQ ID No. 7: nucleotide sequence of the nicotinic acid mononucleotide adenyl transferase 2 (NMA2) from *Saccharomyces cereviseae*.

SEQ ID No. 8: amino acid sequence of the nicotinic acid mononucleotide adenyl transferase 2 (NMA2) from *Saccharomyces cereviseae*.

SEQ ID No. 9: nucleotide sequence of the NAD synthetase (QNS1) from *Saccharomyces cereviseae*.

SEQ ID No. 10: amino acid sequence of the NAD synthetase (QNS1) from *Saccharomyces cereviseae*.

SEQ ID No. 11: nucleotide sequence of the nicotinamidase from *Arabidopsis thaliana* (isoform 1).

SEQ ID No. 12: Amino acid sequence of the nicotinamidase from *Arabidopsis thaliana* (isoform 1).

SEQ ID No. 13: nucleotide sequence of the nicotinamidase from *Arabidopsis thaliana* (isoform 2)

SEQ ID No. 14: Amino acid sequence of the nicotinamidase from *Arabidopsis thaliana* (isoform 2).

SEQ ID No. 15: nucleotide sequence of the nicotinamidase from *Arabidopsis thaliana* (isoform 3)

SEQ ID No. 16: Amino acid sequence of the nicotinamidase from *Arabidopsis thaliana* (isoform 3).

SEQ ID No. 17: nucleotide sequence of the nicotinate phosphoribosyltransferase from *Arabidopsis thaliana* (isoform 1).

SEQ ID No. 18: amino acid sequence of the nicotinate phosphoribosyltransferase from *Arabidopsis thaliana* (isoform 1).

SEQ ID No. 19: nucleotide sequence of the nicotinate phosphoribosyltransferase from *Arabidopsis thaliana* (isoform 2).

SEQ ID No. 20: amino acid sequence of the nicotinate phosphoribosyltransferase from *Arabidopsis thaliana* (isoform 2).

SEQ ID No. 21: nucleotide sequence of the nicotinic acid mononucleotide adenyl transferase from *Arabidopsis thaliana*.

SEQ ID No. 22: amino acid sequence of the nicotinic acid mononucleotide adenyl transferase from *Arabidopsis thaliana*.

SEQ ID No. 23: nucleotide sequence of the NAD synthetase from *Arabidopsis thaliana*.

SEQ ID No. 24: amino acid sequence of the NAD synthetase from *Arabidopsis thaliana*.

SEQ ID No. 25: nucleotide sequence of T-DNA vector pTVE 467

SEQ ID No. 26: nucleotide sequence of T-DNA vector pTVE 468

SEQ ID No. 27: nucleotide sequence of T-DNA vector pTVE 469

SEQ ID No. 28: nucleotide sequence of T-DNA vector pTVE 470

SEQ ID No. 29: nucleotide sequence of T-DNA vector pTVE 496

SEQ ID No. 30: nucleotide sequence of T-DNA vector pTVE 497

SEQ ID No. 31: nucleotide sequence of T-DNA vector pTVE 500

SEQ ID No. 32: nucleotide sequence of T-DNA vector pTVE 501

SEQ ID No. 33: nucleotide sequence of T-DNA vector pTVE 502

SEQ ID No. 34: nucleotide sequence of T-DNA vector pTVE 503

EXAMPLES

Example 1

Assembly of Stress Resistant Chimeric Genes and Introduction into Plants pTVE67

Top increase the stress resistance in plants, a chimeric gene was constructed using conventional techniques comprising the following DNA fragments in order:

A promoter region from Cauliflower Mosaic Virus (CaMV 35S);

A DNA fragment of about 60 bp corresponding to the untranslated leader Cab22L;

A DNA fragment encoding nicotinamidase from *Saccharomyces cereviseae* (SEQ ID NO 1);

A fragment of the 3' untranslated end from the 35 S transcript of CaMV (3'35S)

Figure 2:
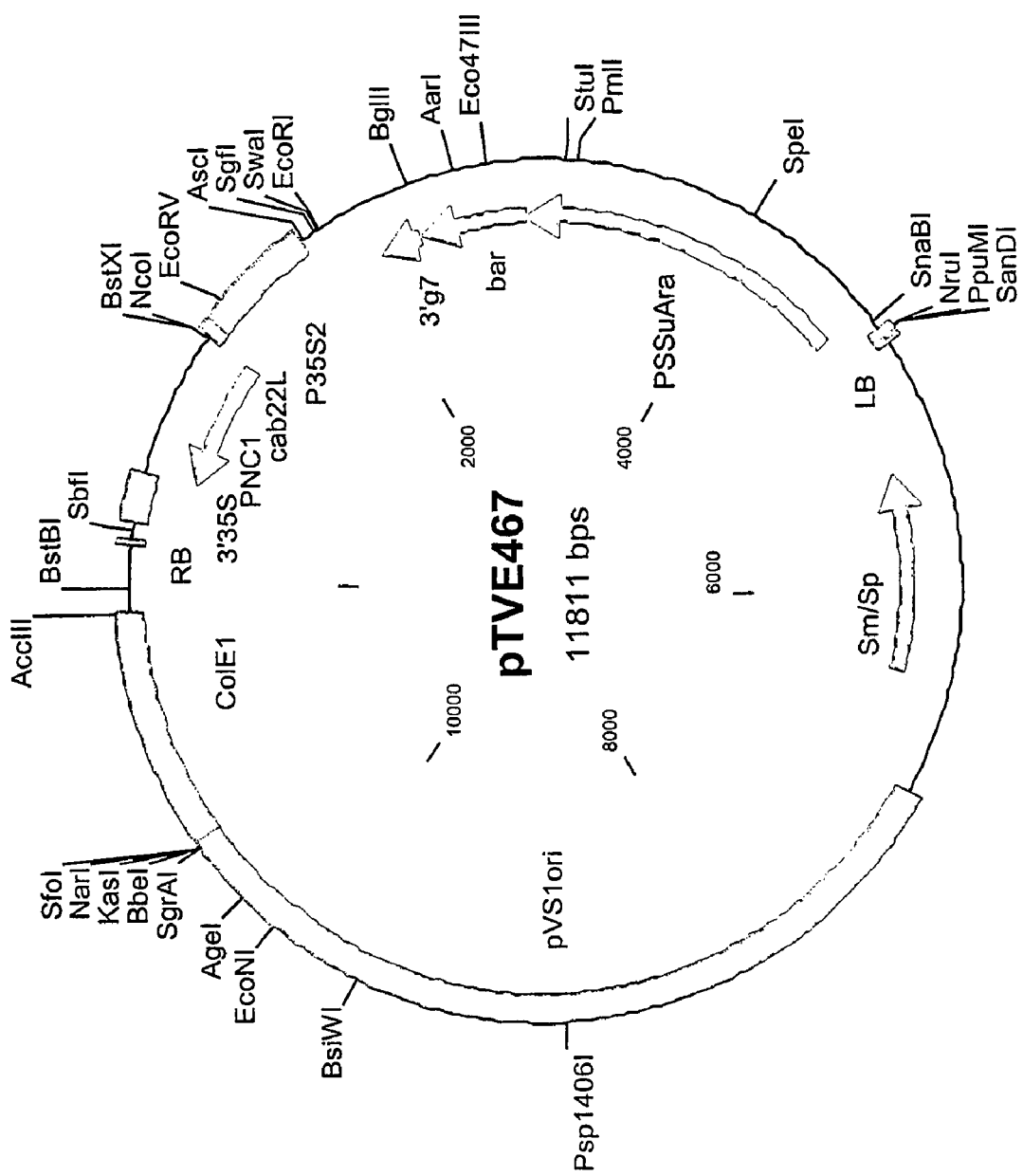
FIGS. 2 to 11 are schematic representations of the various T-DNA vectors comprising DNA regions encoding enzymes from the NAD salvage pathway or the NAD de novo synthesis pathway under control of plant-expressible control elements. Abbreviations used are: RB: right T-DNA border; 3'35S: transcription termination and polyadenylation signal from CaMV 35S transcript; Cab22L:untranslated leader sequence of the Cab22L transcript; P35S2: CaMV 35S promoter; 3'g7: transcription termination and polyadenylation signal from *Agrobacterium tumefaciens* T-DNA gene 7; bar: phosphinotricin acetyltransferase coding region; pSSUAra promoter of the Rubisco small subunit transcript from *Arabidopsis*; LB; left T-DNA border; Sm/Sp: Spectinomycin and streptomycin resistance gene; pVS1ori; origin of VS1 suitable for replication in *Agrobacterium*; ColE1: origin of replication; NLS: nuclear localization signal; PNC1: DNA region coding for nicotinamidase from *Saccharomyces cereviseae*; npt1: the nicotinate phosphoribosyltransferase from *Saccharomyces cereviseae*; nma1: nicotinic acid mononucleotide adenyl transferase 1 from *Saccharomyces cereviseae*; nma2: nicotinic acid mononucleotide adenyl transferase 2 from *Saccharomyces cereviseae*; qns1: NAD synthetase (QNS1) from *Saccharomyces cerevisea*.

This chimeric gene was introduced in a T-DNA vector, between the left and right border sequences from the T-DNA, together with a selectable marker gene providing resistance to the herbicide phosphinotricin, to yield pTVE467 (SEQ ID 25). T-DNA vector pTVE467 is schematically represented in FIG. 2.

T-DNA vector pTVE467 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1181 | 534 (C) | PNC1 coding region |
| 1250 | 1191 (C) | cab22 leader |
| 1781 | 1251 (C) | P35S2 promoter |
| 2293 | 2082 (C) | 3'g7 transcription termination signal |
| 2866 | 2315 (C) | bar coding region |
| 4592 | 2867 (C) | PSSuAra promoter |
| 4760 | 4784 | Left T-DNA border |
| 6352 | 5352 (C) | Sm/Sp resistance gene |
| 6875 | 10645 | pVS1 origin of replication |
| 10646 | 11709 | ColE1 origin of replication | pTVE468

A similar chimeric gene as present in pTVE467 was constructed, wherein the nicotinamidase was equipped with a conventional nuclear localization signal. The chimeric gene thus comprises the following operably linked DNA fragments:

A promoter region from Cauliflower mosaic Virus (CaMV 35S);

A DNA fragment of about 60 nt corresponding to the untranslated leader Cab22L;

A DNA fragment of about 20 nt encoding a peptide comprising a nuclear localization signal (NLS), A DNA fragment encoding nicotinamidase from *Saccharomyces cereviseae* (SEQ ID NO 1); whereby the NLS signal is fused in frame;

A fragment of the 3' untranslated end from the 35 S transcript of CaMV (3'35S)

Figure 3:
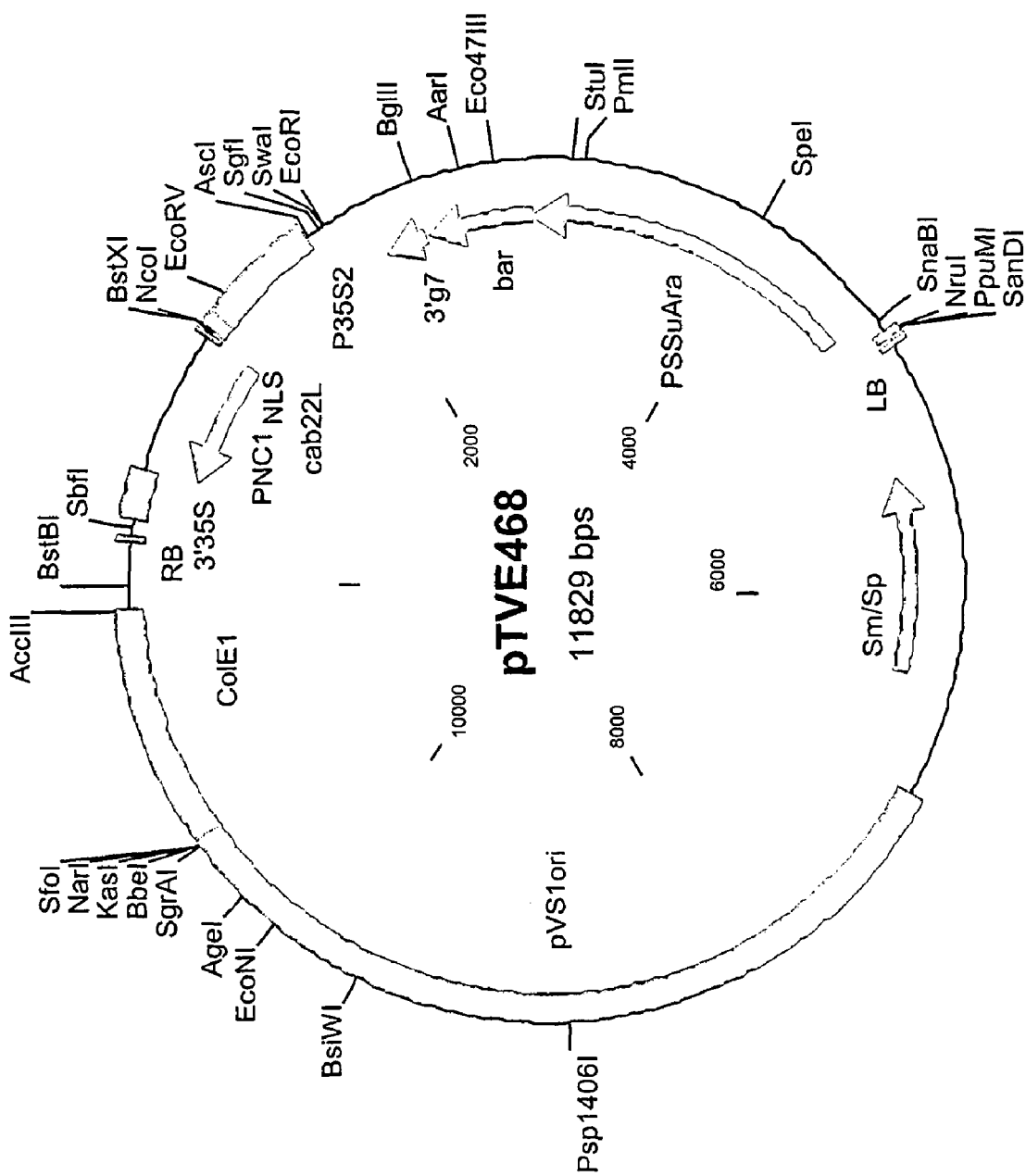

This chimeric gene was introduced in a T-DNA vector, between the left and right border sequences from the T-DNA, together with a selectable marker gene providing resistance to the herbicide phosphinotricin, to yield pTVE468 (SEQ ID 26). T-DNA vector pTVE468 is schematically represented in FIG. 3.

T-DNA vector pTVE468 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1169 | 534 (C) | PNC1 coding region |
| 1187 | 1167 (C) | Nuclear localization signal |
| 1268 | 1209 (C) | cab22 leader |
| 1799 | 1269 (C) | P35S2 promoter |
| 2311 | 2100 (C) | 3'g7 transcription termination signal |
| 2884 | 2333 (C) | bar coding region |
| 4610 | 2885 (C) | PSSuAra promoter |
| 4778 | 4802 | Left T-DNA border |
| 6370 | 5370 (C) | Sm/Sp resistance gene |
| 6893 | 10663 | pVS1origin of replication |
| 10664 | 11727 | ColE1 origin of replication | pTVE469

To increase stress resistance in plants, a chimeric gene was constructed using conventional techniques comprising the following DNA fragments in order:

A promoter region from Cauliflower mosaic Virus (CaMV 35S);

A DNA fragment of about 60 bp corresponding to the untranslated leader Cab22L;

A DNA fragment encoding nicotinate phosphoribosyltransferase from *Saccharomyces cereviseae* (NPT1; SEQ ID NO 3);

A fragment of the 3' untranslated end from the 35 S transcript of CaMV (3'35S)

Figure 4:
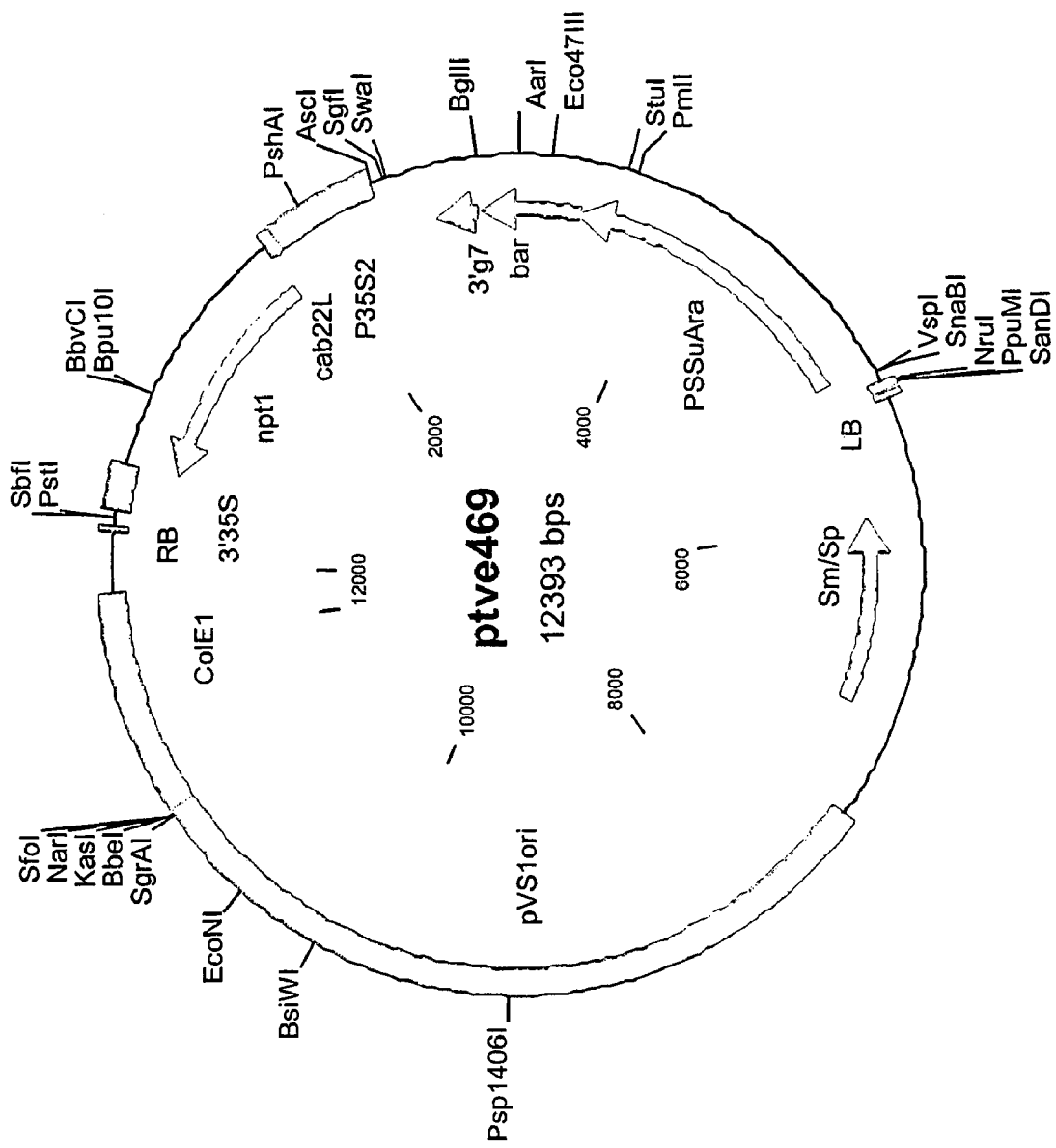

This chimeric gene was introduced in a T-DNA vector, between the left and right border sequences from the T-DNA, together with a selectable marker gene providing resistance to the herbicide phosphinotricin, to yield pTVE469 (SEQ ID 27). T-DNA vector pTVE469 is schematically represented in FIG. 4.

T-DNA vector pTVE469 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1765 | 534 (C) | NPT1 coding region |
| 1832 | 1773 (C) | cab22 leader |
| 2363 | 1833 (C) | P35S2 promoter |
| 2875 | 2664 (C) | 3'g7 transcription termination signal |
| 3448 | 2897 (C) | bar coding region |
| 5175 | 3449 (C) | PSSuAra promoter |
| 5342 | 5366 | Left T-DNA border |
| 6934 | 5934 (C) | Sm/Sp resistance gene |
| 7457 | 11227 | pVS1origin of replication |
| 11228 | 12291 | ColE1 origin of replication | pTVE470

A similar chimeric gene as present in pTVE469 was constructed, wherein the nicotinate phosphoribosyltransferase from *Saccharomyces cereviseae* was equipped with a conventional nuclear localization signal The chimeric gene thus comprises the following operably linked DNA fragments:

A promoter region from Cauliflower mosaic Virus (CaMV 35S);

A DNA fragment of about 60 nt corresponding to the untranslated leader Cab22L;

A DNA fragment of about 20 nt encoding a peptide comprising a nuclear localization signal (NLS), A DNA fragment encoding nicotinate phosphoribosyltransferase from *Saccharomyces cereviseae* (NPT1; SEQ ID NO 3); whereby the NLS signal is fused in frame;

A fragment of the 3' untranslated end from the 35 S transcript of CaMV (3'35S)

Figure 5:
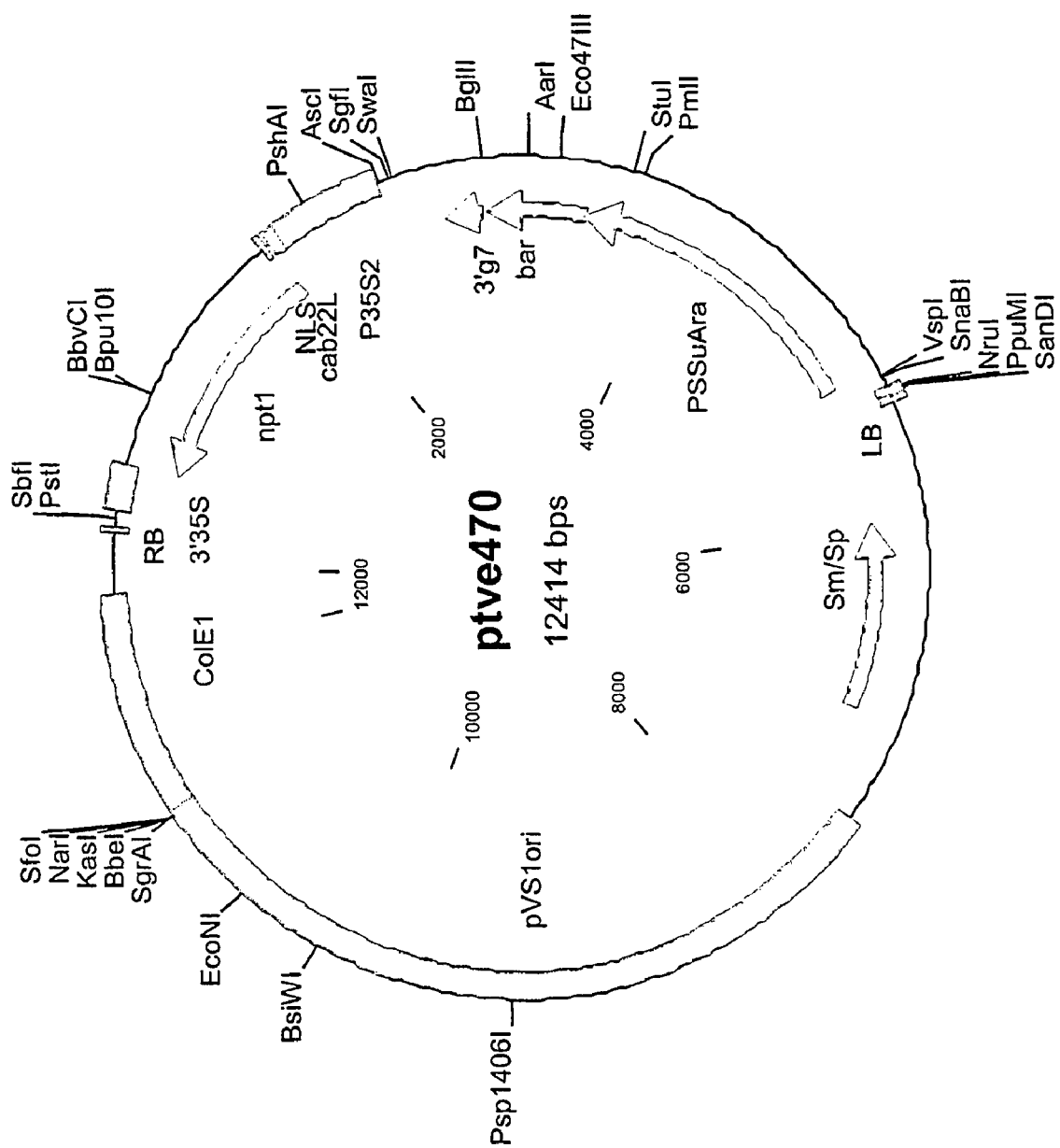

This chimeric gene was introduced in a T-DNA vector, between the left and right border sequences from the T-DNA, together with a selectable marker gene providing resistance to the herbicide phosphinotricin, to yield pTVE470 (SEQ ID 28). T-DNA vector pTVE470 is schematically represented in FIG. 5.

T-DNA vector pTVE470 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1787 | 534 (C) | NPT1 coding region |
| 1775 | 1755 (C) | Nuclear localization signal SV40 |
| 1853 | 1794 (C) | cab22 leader |
| 2384 | 1854 (C) | P35S2 promoter |
| 2896 | 2685 (C) | 3'g7 transcription termination signal |
| 3469 | 2918 (C) | bar coding region |
| 5195 | 3470 (C) | PSSuAra promoter |
| 5363 | 5387 | Left T-DNA border |
| 6955 | 5955 (C) | Sm/Sp resistance gene |
| 7478 | 11248 | pVS1origin of replication |
| 11249 | 12312 | ColE1 origin of replication | pTVE496

To increase stress resistance in plants, a chimeric gene was constructed using conventional techniques comprising the following DNA fragments in order:

A promoter region from Cauliflower mosaic Virus (CaMV 35S);

A DNA fragment of about 60 bp corresponding to the untranslated leader Cab22L;

A DNA fragment encoding nicotinic acid mononucleotide adenyl transferase I from *Saccharomyces cereviseae* (NMA1; SEQ ID NO 5);

A fragment of the 3' untranslated end from the 35 S transcript of CaMV (3'35S)

Figure 6:
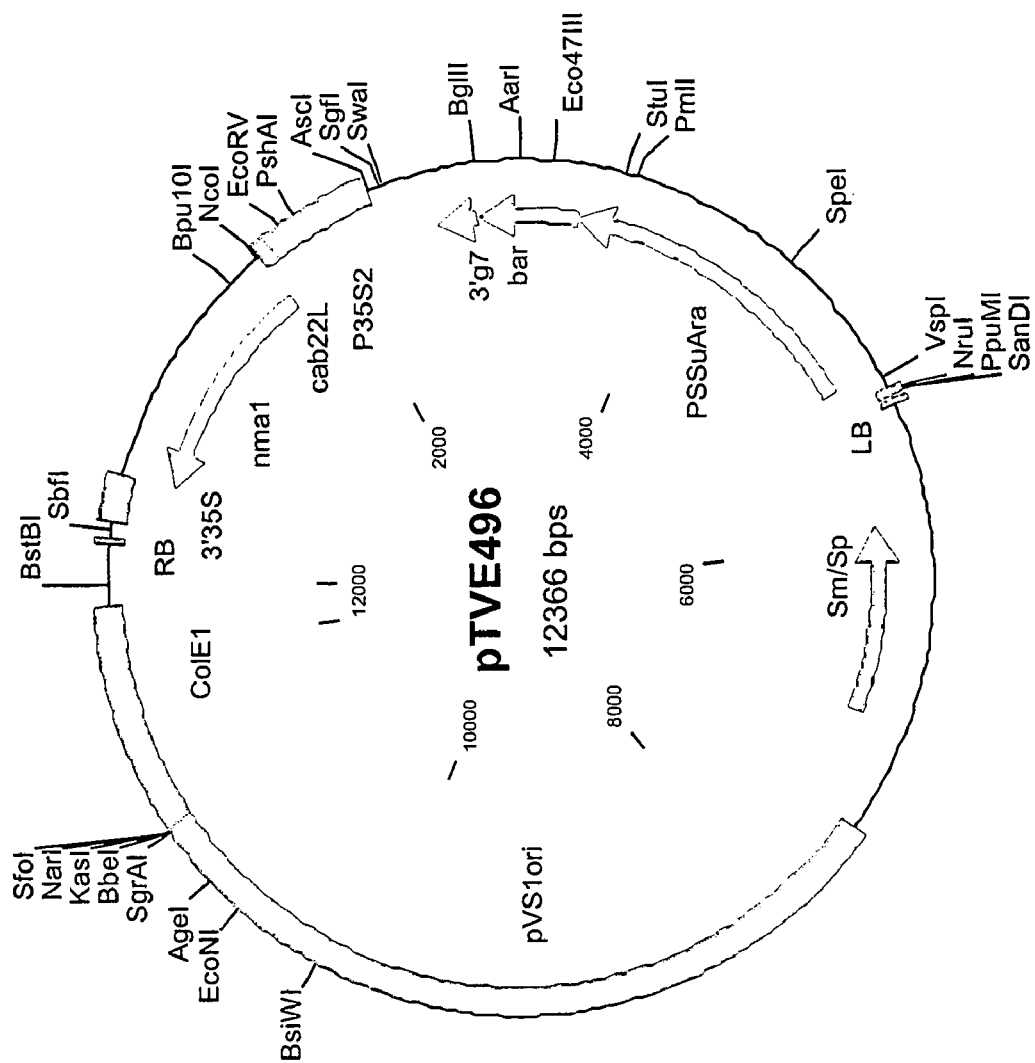

This chimeric gene was introduced in a T-DNA vector, between the left and right border sequences from the T-DNA, together with a selectable marker gene providing resistance to the herbicide phosphinotricin, to yield pTVE496 (SEQ ID 29). T-DNA vector pTVE496 is schematically represented in FIG. 6.

T-DNA vector pTVE496 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1739 | 534 (C) | NMA1 coding region |
| 1805 | 1746 (C) | cab22 leader |
| 2336 | 1806 (C) | P35S2 promoter |
| 2848 | 2637 (C) | 3'g7 transcription termination signal |
| 3421 | 2870 (C) | bar coding region |
| 5147 | 3422 (C) | PSSuAra promoter |
| 5315 | 5339 | Left T-DNA border |
| 6907 | 5907 (C) | Sm/Sp resistance gene |
| 7430 | 11200 | pVS1 origin of replication |
| 11201 | 12264 | ColE1 origin of replication | pTVE497

A similar chimeric gene as present in pTVE496 was constructed, wherein the nicotinic acid mononucleotide adenyl transferase 1 from *Saccharomyces cereviseae* was equipped with a conventional nuclear localization signal The chimeric gene thus comprises the following operably linked DNA fragments:

A promoter region from Cauliflower mosaic Virus (CaMV 35S);

A DNA fragment of about 60 nt corresponding to the untranslated leader Cab22L;

A DNA fragment of about 20 nt encoding a peptide comprising a nuclear localization signal (NLS), A DNA fragment encoding nicotinic acid mononucleotide adenyl transferase 1 from *Saccharomyces cereviseae* (NMA1; SEQ ID NO 5); whereby the NLS signal is fused in frame;

A fragment of the 3' untranslated end from the 35 S transcript of CaMV (3'35S)

Figure 7:
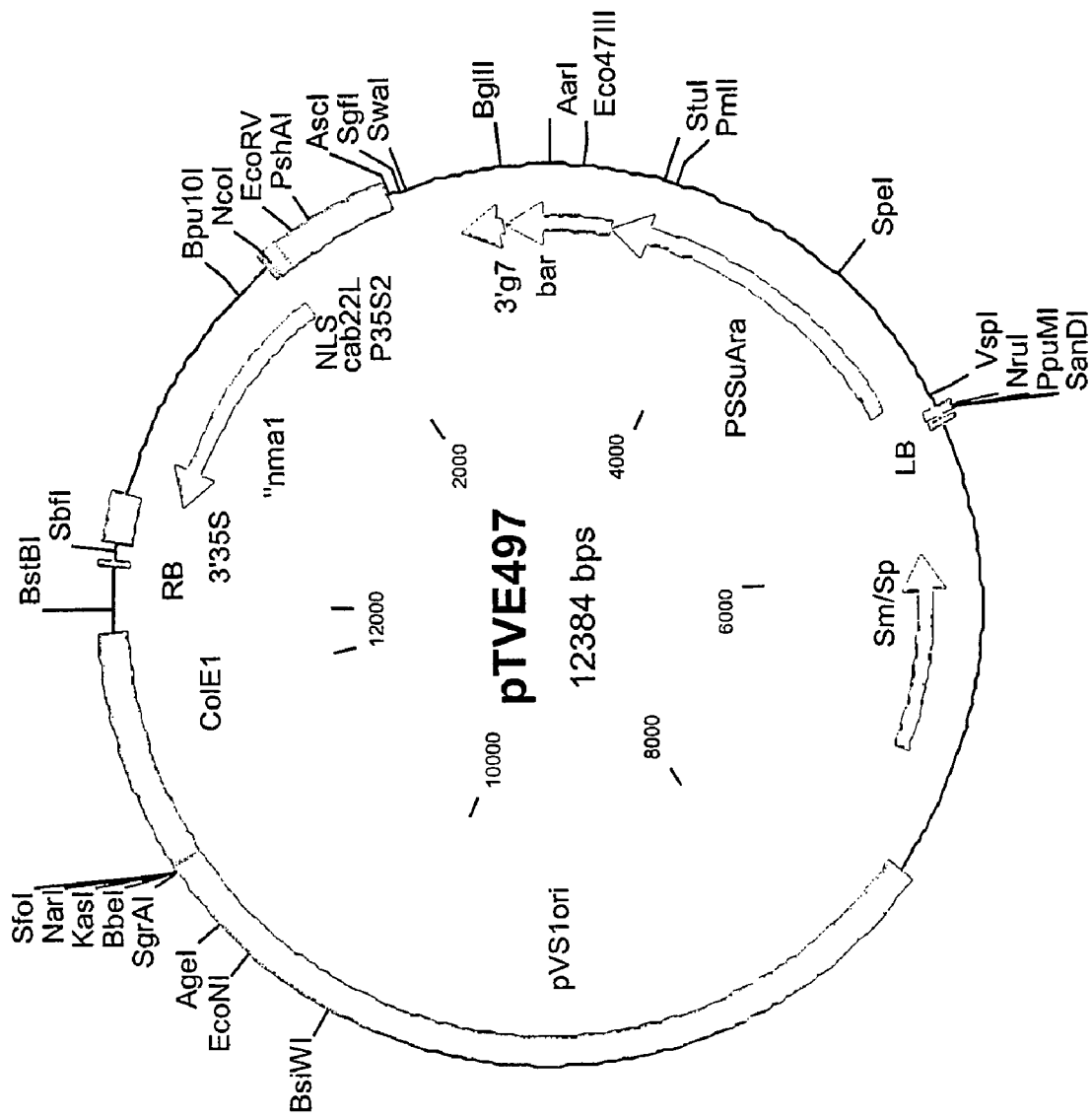

This chimeric gene was introduced in a T-DNA vector, between the left and right border sequences from the T-DNA, together with a selectable marker gene providing resistance to the herbicide phosphinotricin, to yield pTVE497 (SEQ ID 30). T-DNA vector pTVE497 is schematically represented in FIG. 7.

T-DNA vector pTVE497 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |

-continued

| Start (nt) | End (nt) | |
|---|---|---|
| 1757 | 534 (C) | NMA1 coding region |
| 1748 | 1731 (C) | Nuclear localization signal SV40 |
| 1823 | 1764 (C) | cab22 leader |
| 2354 | 1824 (C) | P35S2 promoter |
| 2866 | 2655 (C) | 3'g7 transcription termination signal |
| 3439 | 2888 (C) | bar coding region |
| 5165 | 3440 (C) | PSSuAra promoter |
| 5333 | 5357 | Left T-DNA border |
| 6925 | 5925 (C) | Sm/Sp resistance gene |
| 7448 | 11218 | pVS1 origin of replication |
| 11219 | 12282 | ColE1 origin of replication | pTVE500

To increase stress resistance in plants, a chimeric gene was constructed using conventional techniques comprising the following DNA fragments in order:

A promoter region from Cauliflower mosaic Virus (CaMV 35S);

A DNA fragment of about 60 bp corresponding to the untranslated leader Cab22L;

A DNA fragment encoding nicotinic acid mononucleotide adenyl transferase 2 from *Saccharomyces cereviseae* (NMA2; SEQ ID No. 7);

A fragment of the 3' untranslated end from the 35S transcript of CaMV (3'35S).

Figure 8:
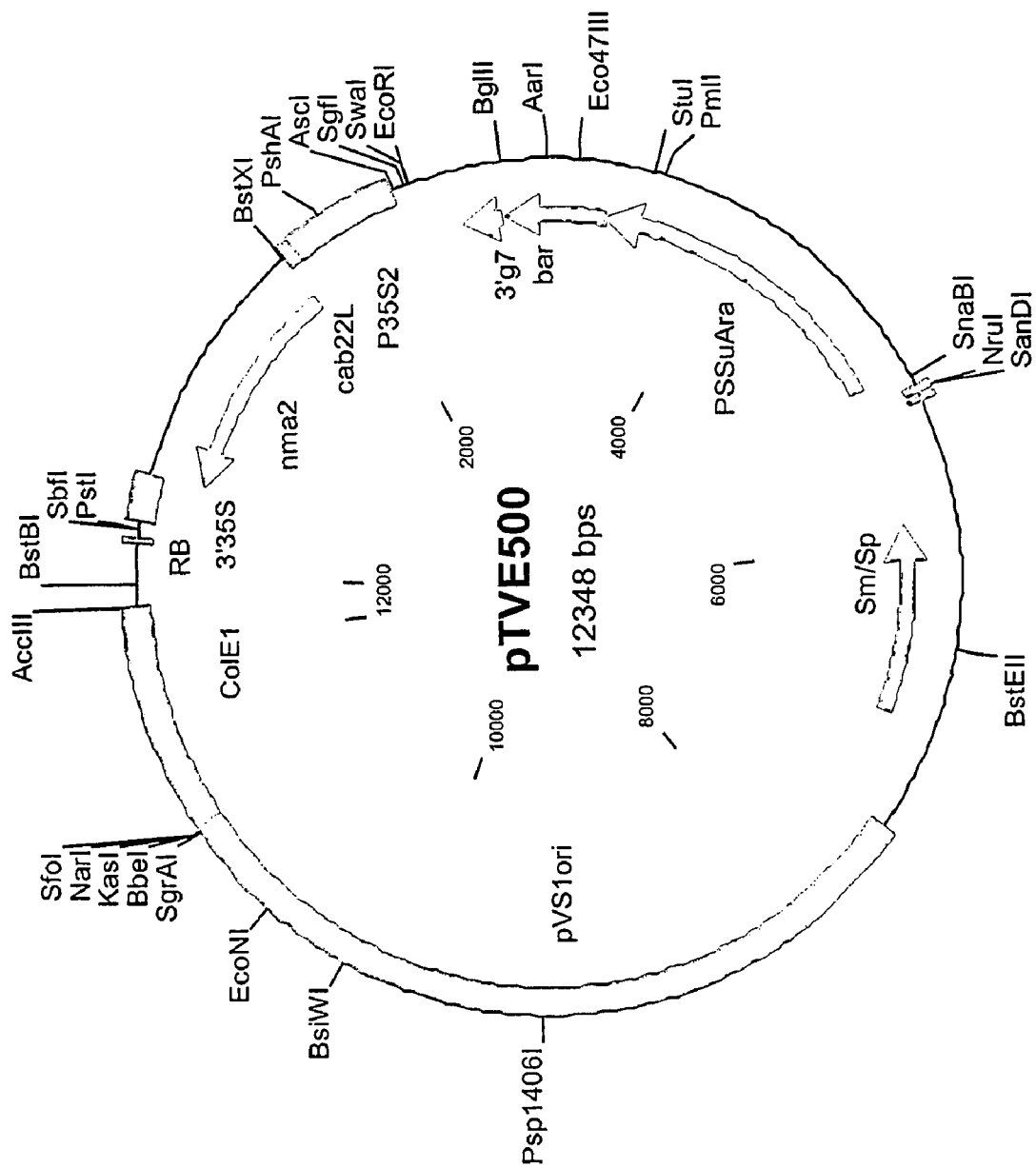

This chimeric gene was introduced in a T-DNA vector, between the left and right border sequences from the T-DNA, together with a selectable marker gene providing resistance to the herbicide phosphinotricin, to yield pTVE500 (SEQ ID 31). T-DNA vector pTVE500 is schematically represented in FIG. 8.

T-DNA vector pTVE500 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1721 | 534 (C) | NMA2 coding region |
| 1787 | 1728 (C) | cab22 leader |
| 2318 | 1788 (C) | P35S2 promoter |
| 2830 | 2619 (C) | 3'g7 transcription termination signal |
| 3403 | 2852 (C) | bar coding region |
| 5129 | 3404 (C) | PSSuAra promoter |
| 5297 | 5321 | Left T-DNA border |
| 6889 | 5889 (C) | Sm/Sp resistance gene |
| 7412 | 11182 | pVS1 origin of replication |
| 11183 | 12246 | ColE1 origin of replication | pTVE501

A similar chimeric gene as present in pTVE500 was constructed, wherein the nicotinic acid mononucleotide adenyl transferase 2 from *Saccharomyces cereviseae* was equipped with a conventional nuclear localization signal The chimeric gene thus comprises the following operably linked DNA fragments:

A promoter region from Cauliflower mosaic Virus (CaMV 35S);

A DNA fragment of about 60 nt corresponding to the untranslated leader Cab22L;

A DNA fragment of about 20 nt encoding a peptide comprising a nuclear localization signal (NLS), A DNA fragment encoding nicotinic acid mononucleotide adenyl transferase 2 from *Saccharomyces cereviseae* (NMA2; SEQ ID No. 7); whereby the NLS signal is fused in frame;

A fragment of the 3' untranslated end from the 35 S transcript of CaMV (3'35S)

Figure 9:
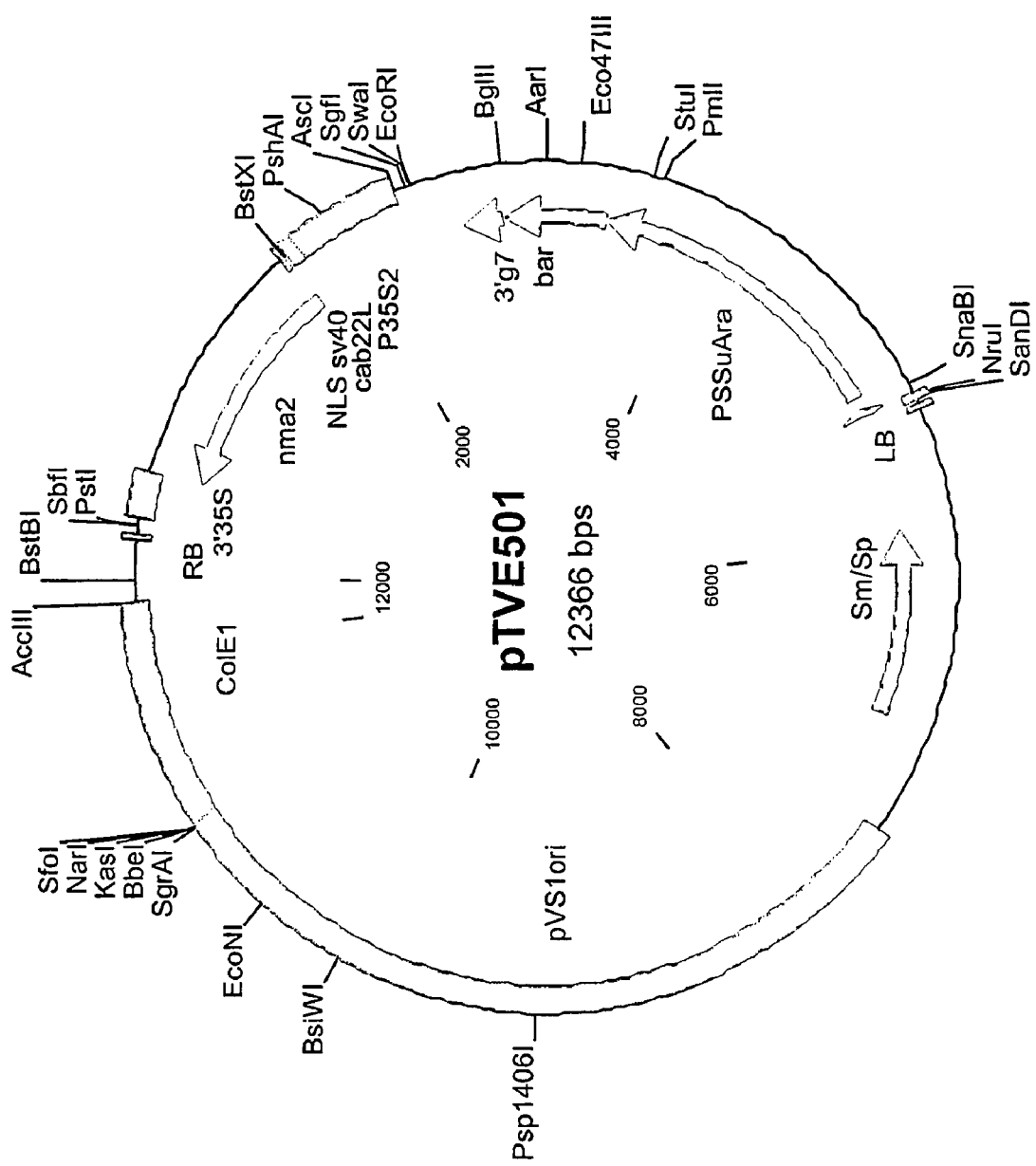

This chimeric gene was introduced in a T-DNA vector, between the left and right border sequences from the T-DNA, together with a selectable marker gene providing resistance to the herbicide phosphinotricin, to yield pTVE502 (SEQ ID 32). T-DNA vector pTVE501 is schematically represented in FIG. 9.

T-DNA vector pTVE501 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 1739 | 534 (C) | NMA2 coding region |
| 1733 | 1713 (C) | Nuclear localization signal SV40 |
| 1805 | 1746 (C) | cab22 leader |
| 2336 | 1806 (C) | P35S2 promoter |
| 2848 | 2637 (C) | 3'g7 transcription termination signal |
| 3421 | 2870 (C) | bar coding region |
| 5165 | 3440 (C) | PSSuAra promoter |
| 5315 | 5339 | Left T-DNA border |
| 6907 | 5907 (C) | Sm/Sp resistance gene |
| 7430 | 11200 | pVS1 origin of replication |
| 11201 | 12264 | ColE1 origin of replication | pTVE502

To increase stress resistance in plants, a chimeric gene was constructed using conventional techniques comprising the following DNA fragments in order:

A promoter region from Cauliflower mosaic Virus (CaMV 35S);

A DNA fragment of about 60 bp corresponding to the untranslated leader Cab22L;

A DNA fragment encoding NAD synthase from *Saccharomyces cereviseae* (QNS1; SEQ ID No. 9);

A fragment of the 3' untranslated end from the 35S transcript of CaMV (3'35S).

Figure 10:
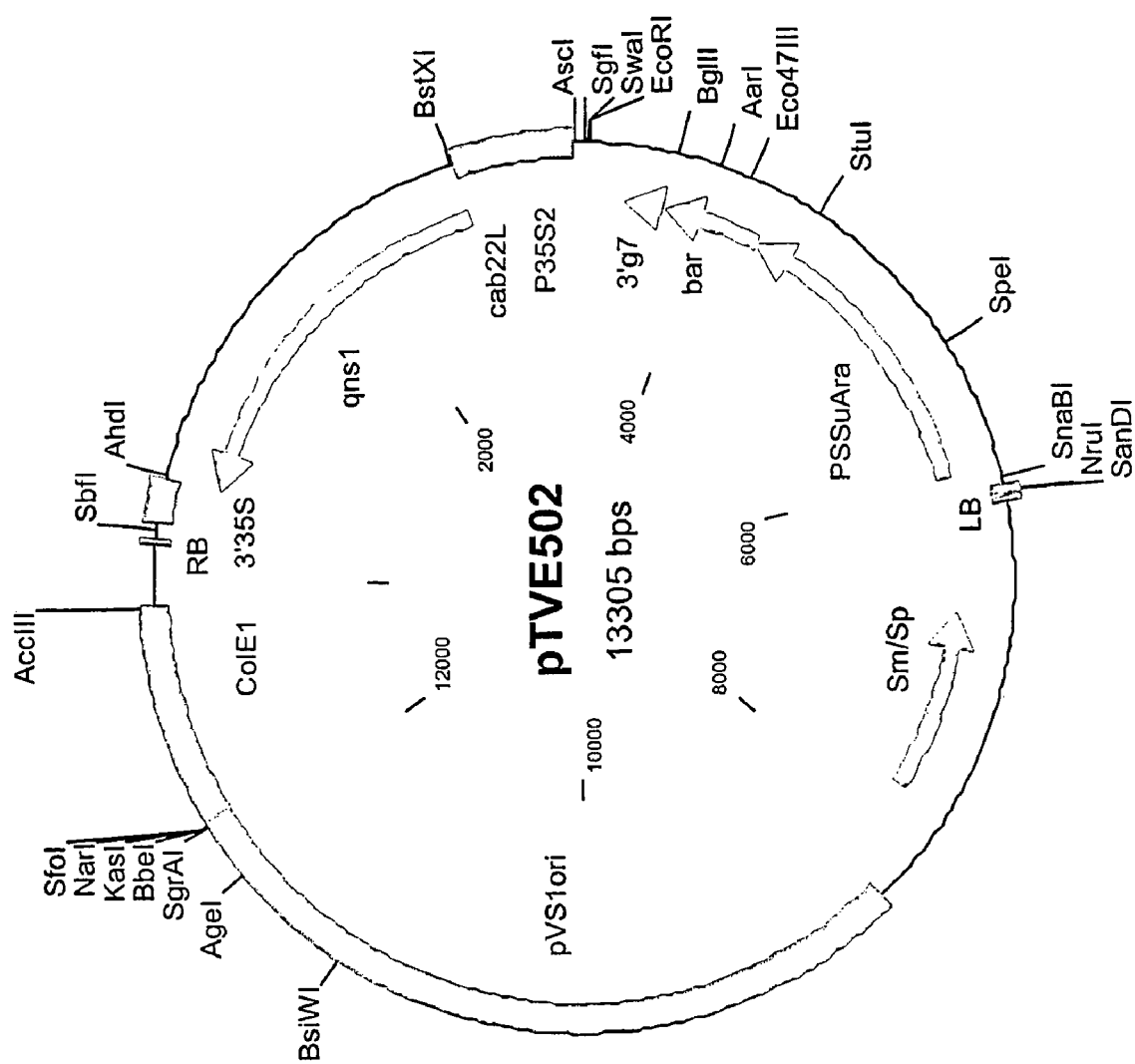

This chimeric gene was introduced in a T-DNA vector, between the left and right border sequences from the T-DNA, together with a selectable marker gene providing resistance to the herbicide phosphinotricin, to yield pTVE502 (SEQ ID 33). T-DNA vector pTVE502 is schematically represented in FIG. 10.

T-DNA vector pTVE502 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 2678 | 534 (C) | QNS1 coding region |
| 2744 | 2685 (C) | cab22 leader |
| 3275 | 2745 (C) | P35S2 promoter |
| 3787 | 3576 (C) | 3'g7 transcription termination signal |
| 4360 | 3809 (C) | bar coding region |
| 6086 | 4361 (C) | PSSuAra promoter |
| 6254 | 6278 | Left T-DNA border |
| 7846 | 6846 (C) | Sm/Sp resistance gene |
| 8369 | 12139 | pVS1 origin of replication |
| 12140 | 13203 | ColE1 origin of replication | pTVE503

A similar chimeric gene as present in pTVE502 was constructed, wherein the NAD synthase from *Saccharomyces cereviseae* was equipped with a conventional nuclear localization signal The chimeric gene thus comprises the following operably linked DNA fragments:

A promoter region from Cauliflower mosaic Virus (CaMV 35S);

A DNA fragment of about 60 nt corresponding to the untranslated leader Cab22L;

A DNA fragment of about 20 nt encoding a peptide comprising a nuclear localization signal (NLS), A DNA fragment encoding NAD synthase from *Saccharomyces cereviseae* (QNS1; SEQ ID No. ç); whereby the NLS signal is fused in frame;

A fragment of the 3' untranslated end from the 35 S transcript of CaMV (3'35S)

Figure 11:
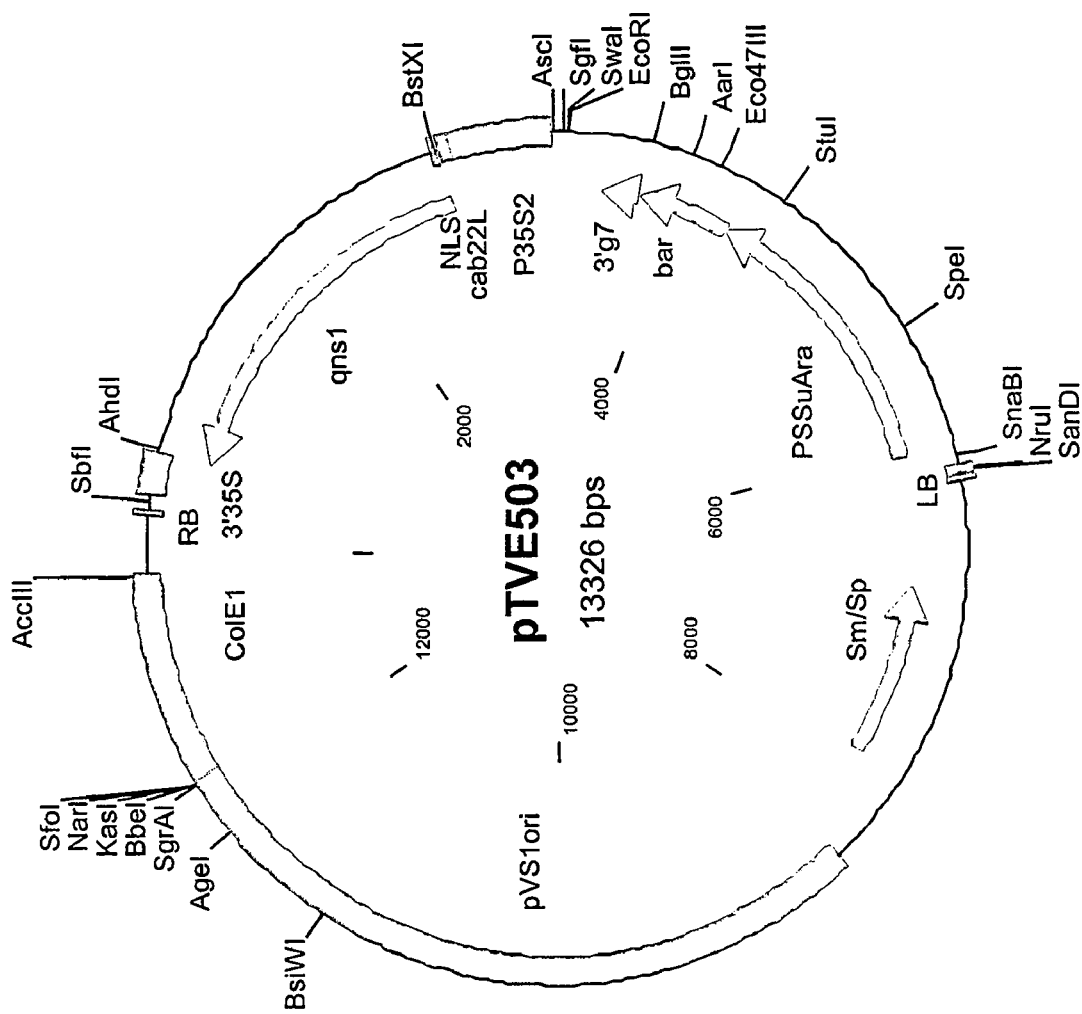

This chimeric gene was introduced in a T-DNA vector, between the left and right border sequences from the T-DNA, together with a selectable marker gene providing resistance to the herbicide phosphinotricin, to yield pTVE503 (SEQ ID No. 34). T-DNA vector pTVE503 is schematically represented in FIG. 11.

T-DNA vector pTVE503 comprises the following molecule features:

(C) indicates complementary strand.

| Start (nt) | End (nt) | |
|---|---|---|
| 198 | 222 | RB: right T-DNA border |
| 521 | 300 (C) | 3'35S: transcription termination signal |
| 2699 | 534 (C) | QNS1 coding region |
| 2690 | 2670 (C) | Nuclear localization signal SV40 |
| 2765 | 2706 (C) | cab22 leader |
| 3296 | 2766 (C) | P35S2 promoter |
| 3808 | 3597 (C) | 3'g7 transcription termination signal |
| 4381 | 3830 (C) | bar coding region |
| 6107 | 4382 (C) | PSSuAra promoter |
| 6275 | 6299 | Left T-DNA border |
| 7867 | 6867 (C) | Sm/Sp resistance gene |
| 8390 | 12610 | pVS1 origin of replication |
| 12161 | 13224 | ColE1 origin of replication |

The T-DNA vectors were introduced into *Agrobacterium* strains comprising a helper Ti-plasmid using conventional methods. The chimeric genes were introduced into *Arabidopsis* plants by *Agrobacterium* mediated transformation as described in the art.

Example 2

Analysis of Transgenic *Arabidopsis* Lines Comprising the Chimeric Genes Described in Example 1

Seed of transgenic *Arabidopsis* lines (T1-generation) expressing the yeast genes of the NAD-salvage pathway, obtained as described in Example 1 were germinated and grown on medium containing 15 mg $L^{-1}$ phosphinotricin (PPT). *Arabidopsis thaliana* cv Col-0 was used as a control.

All plants were subjected to high light stress. Two week old plants grown at 30 µEinstein $m^{-2}$ $sec^{-1}$ were transferred to 250 µEinstein $m^{-2}$ $sec^{-1}$ (high light) for 6 hours, followed by 8 hours in the dark and again 8 hours high light.

After this treatment, NADH content and superoxide radicals content were determined for all lines and compared to measurement of the same compounds in transgenic and control lines grown under low light conditions. The results are summarized in Table 1.

Transgenic plants exhibited a higher NADH content under high light than control plants, and produced less reactive oxygen species under high light than control plants. No difference was observed between constructs wherein the encoded NAD salvage pathway enzyme was equipped with a nuclear localization signal or not.

Transgenic plant lines were also phenotypically scored for tolerance to high light stress conditions. To this end, plants were grown in vitro at low light conditions (30 µEinstein $m^{-2}$ $sec^{-1}$) for two weeks and transferred for 3 days to high light conditions (250 µEinstein $m^{-2}$ $sec^{-1}$; 16 hrs light –8 hrs dark). After the high light treatment the plants were returned to low light conditions and grown for another three days before scoring the phenotype.

Whereas control plants were small, and had started flowering (stress-induced), the plants of the transgenic lines comprising the chimeric genes as described in Example 1 were larger than the control plants and only had started to bolt.

TABLE 1

High light tolerance of transgenic *Arabidopsis* lines over-expressing the chimeric yeast genes as described in Example 1.

| Chimeric genes | Segregation for PPT tolerance | % NADH versus low light control | | % superoxides versus low light control | |
|---|---|---|---|---|---|
| | | Low light | High light | Low light | High light |
| Control | — | 100 | 68 | 100 | 145 |
| PNC1 (NLS) line 1 | 3:1 | 108 | 128 | 80 | 73 |
| PNC1 (NLS) line 2 | 3:1 | 139 | 128 | 82 | 76 |
| NPT1 line 1 | 6:1 | 128 | 147 | 66 | 70 |
| NPT1 line 2 | 6:1 | 122 | 135 | 82 | 76 |
| NPT1 (NLS) | 12:1 | 106 | 150 | 61 | 80 |

STANDARD ERROR OF MEAN <10%

Example 3

Protocols for Measurement of NADH Content and Superoxide Content

Intracellular NAD(P)H Quantification Using a Water-Soluble Tetrazolium Salt

Reference
Jun Nakamura, Shoji Asakura, Susan D. Hester, Gilbert de Murcia, Keith W. Caldecott and James A. Swenberg (2003) Quantitation of intracellular NAD(P)H can monitor an imbalance of DNA single strand break repair in base excision repair deficient cells in real time. Nucleic Acids Research 31(17), e104.

Plant Material
  Most plant material can be used:
  In vitro grown *Arabidopsis* shoots 14-18 days old but NOT flowering
  Hypocotyl explants of oilseed rape Cell Counting Kit-8 (CCK-8)
  Sopachem n.v./Belgium
  72A, Avenue du Laarbeeklaan—1090 Brussels Belgium
  Contents:
  5 mL bottles containing 5 mMol/L WST-8 (tetrazolium salt), 0.2 mMol/L 1-Methoxy PMS, 150 mMol/L NaCl
  Reaction Solution:
  10 mL 25mM K-phosphate buffer pH7.4
  0.5 mL CCK-8
  0.1 mM 1-Methoxy-5-methylphenazinium methyl sulfate (=1-Methoxyphenazine methosulfate): 1 µUL/mL of 100 mM stock (MW=336.4; 100 mg in 2.973 mL water)
  1 drop Tween20/25 mL Procedure
  Harvest plant material and put in 25 mM K-phosphate buffer pH7.4 e.g.: 150 oilseed rape hypocotyl explants
    1 gr *Arabidopsis* shoots (without roots)
  Replace buffer with reaction solution
    15 mL for 1 gr *Arabidopsis* shoots
    15 mL for 150 oilseed rape hypocotyl explants
  Incubate at 26° C. in the dark for about ½ hour (follow reaction)
  Measure the absorbance of the reaction solution at 450 nm Measuring Superoxide Production by Quantifying the Reduction of XTT
Ref.: De Block, M., De Brouwer, D. (2002) A simple and robust in vitro assay to quantify the vigour of oilseed rape lines and hybrids. Plant Physiol. Biochem. 40, 845-852

A. *BRASSICA NAPUS*

Media and Reaction Buffers
  Sowing medium (medium 201):
  Half concentrated Murashige and Skoog salts
  2% sucrose
  pH 5.8
  0.6% agar (Difco Bacto Agar)
  250 mg/l triacillin
  Callus inducing medium A2S3:
  MS medium, 0.5 g/l Mes (pH 5.8), 3% sucrose, 40 mg/l adenine-$SO_4$, 0.5% agarose, 1 mg/l 2,4-D, 0.25 mg/l NM, 1 mg/l BAP, 250 mg/l triacillin Reaction Buffer:
25 mM K-phosphate buffer pH 8
1 mM sodium, 3'-{1-[phenylamino-carbonyl]-3,4-tetrazolium}-bis(4-methoxy-6-nitro)=XTT (BioVectra, Canada) (MW 674.53)
Dissolve XTT by careful warming solution (±37° C.) (cool down to room temperature before use)
1 drop Tween20 for 25 ml buffer Sterilization of Seeds—Pregermination of Seeds—Growing of the Seedlings Seeds are soaked in 70% ethanol for 2 min, then surface-sterilized for 15 min in a sodium hypochlorite solution (with about 6% active chlorine) containing 0.1% Tween20. Finally, the seeds are rinsed with 1l of sterile tap water.

Incubate seeds for at least one hour in sterile tap water (to allow diffusion from seeds of components that may inhibit germination).

Seeds are put in 250 ml erlenmeyer flasks containing 50 ml of sterile tap water (+250 mg/l triacillin). Shake for about 20 hours.

Seeds from which the radicle is protruded are put in Vitro Vent containers from Duchefa containing about 125 ml of sowing medium (10 seeds/vessel, not too many to reduce loss of seed by contamination). The seeds are germinated at ±24° C. and 10-30 µEinstein $s^{-1}m^{-2}$ with a daylength of 16 h.
    P.S.: For calculating the amount of seeds that have to be sawn: 5 hypocytyl segments/seedling Preculture of the Hypocotyl Explants and Induction of Stress
    12-14 days after sowing, the hypocotyls are cut in about 7-10 mm segments.
    The hypocotyl explants (25 hypocotyls/Optilux Petridish, Falcon S1005, Denmark) are cultured for 5 days on medium A2S3 at 25° C. (at 10-30 µEinstein $s^{-1}m^{-2}$).
    P.S.: 150 hypocotyl explants are used per condition.
    Induction of stress:
        Transfer hypocotyl explants to A2S3 medium containing respectively 0, 25 and 50 mg/l acetylsalicylic acid.
        Incubate for about 24 hours at 25° C. and 10-30 µEinstein $s^{-1}m^{-2}$ with a daylength of 16 h.

XTT-Assay
    Transfer 150 hypocotyl explants to a 50 ml Falcon tube.
    Wash with reaction buffer (without XTT).
    Add 20 mL reaction buffer+XTT.
        (explants have to be submerged, but do not vacuum infiltrate)
    Incubate in the dark at 26° C.
    Follow the reaction by measuring the absorption of the reaction medium at 470 nm

B. *ARABIDOPSIS THALIANA*

Media and Reaction Buffers
    Plant medium:
    Half concentrated Murashige and Skoog salts
    B5 vitamins
    1.5% sucrose
    pH 5.8
    0.7% Difco agar
    Incubation medium:
    ½ concentrated MS-salts
    1% sucrose
    0.5 g/L MES pH 5.8
    1 drop Tween20 for 25 ml medium
    Reaction buffer:
    25 mM K-phosphate buffer pH 8
    1 mM sodium, 3'-{1-[phenylamino-carbonyl]-3,4-tetrazolium}-bis(4-methoxy-6-nitro)=XTT (BioVectra, Canada) (MW 674.53)
    Dissolve XTT by careful warming solution (±37° C.) (cool down to room temperature before use)
    1 drop Tween20 for 25 ml buffer

*Arabidopsis* Plants
    *Arabidopsis* lines: control (mother line from which tested lines were derived) lines to test
    Sterilization of *Arabidopsis* seeds:
        2 min. 70% ethanol
        10 min. bleach (6% active chlorine)+1 drop Tween 20 for 20 ml solution wash 5 times with sterile tap water
        P.S.: sterilization is done in 2 ml eppendorf tubes *Arabidopsis* seeds sink to the bottom of the tube, allowing removal of the liquids by means of a 1 ml pipetman
    Pregermination of seeds:
        In 9 cm Optilux Petridishes (Falcon) containing 12 ml sterile tap water.
    Low light overnight to 24 hours.
    Growing of *Arabidopsis* plants
        Seeds are sown in Intergrid Tissue Culture disks of Falcon (nr. 3025) containing ±125 ml of plant medium: 1 seed/grid.
    Plants are grown at 24° C.
        30 µEinstein $s^{-1}m^{-2}$
        16 hours light-8 hours dark
        for about 18 days (before bolting)
        P.S.: 1 g of plant material (shoots without roots)/line/condition are needed to carry out the assay. 1 g shoots corresponds with 40-60 plants.

Induction of Stress

Paraquat
    Harvest *Arabidopsis* shoots (without roots)
    Put 1 g shoots in incubation medium (shoots have to be submerged, but do not vacuum infiltrate) containing respectively 0, 5 and 10 µM paraquat
    Incubation medium: +150 ml in Intergrid Tissue Culture disks of Falcon (nr. 3025)
    Incubate at 24° C. in the dark for ±24 hours and 30-50 µEinstein $s^{-1}m^{-2}$ with a daylength of 16 h.

High Light
    Transfer half of the plates to high light (250 µEinstein $s^{-1}m^{-2}$) and incubate for 4 to 20 hours XTT-Assay
    Harvest shoots (without roots) from agar plates (high light stress) or from liquid incubation medium (paraquat stress) and put them in 50 ml Falcon tubes containing reaction buffer (without XTT)
    Replace reaction buffer with buffer containing XTT (15 mL/gr)
    Shoots have to be submerged, but do not vacuum infiltrate
    Incubate in the dark at 26° C.
    Follow the reaction by measuring the absorption of the reaction medium at 470 nm (about one hour)

Example 4

Increased Ozone Tolerance of *Arabidopsis thaliana* Plants Over-Expressing the Yeast Nicotineamidase (Pnc1) Gene The chimeric vector pTVE467 (Example 1) was used for transformation of *A. thaliana* ecotype Columbia. Primary transformants were analyzed by Southern-DNA- and Northern-RNA-blot analysis. One transgenic line was identified to carry a single copy of the Pnc1-transgene construct and to have a high steady state level of transgenic full-length Pnc1-mRNA (20 pg/5 µg total RNA).

6 weeks after germination 100 individual plants each of the single copy transgenic line and of wild-type Columbia as a control, were exposed to ozone in fumigation chambers. During 2 consecutive days the plants were treated for 5 h/day with ozone concentrations of 250, 350 and 500 ppb respectively. After treatment all plants were visually screened for ozone injury manifested as necrotic lesions. The results are summarized in Table 2. At 500 ppb ozone exposure nearly all plants showed necrotic lesions whereas at the 2 lower ozone concentrations a significantly lower percentage of transgenic plants were injured.

In addition, the evolution of the vitality performance index (PI) was determined for all plants of the transgenic line and of the wild-type plants under increasing ozone concentration. PI can be calculated by the formula: PI=(ABS/CS)×(TR/CS)×(ET/CS). (ABS=flux of photons absorbed by the antenna pigments Chl*; CS=cross section; TR=energy trapped by the reaction centre and converted into redox energy; ET=electron flux further downstream leading to $CO_2$ fixation) In the transgenic line, the vitality performance index PI significantly increased with increasing ozone concentrations whereas this index remains constant in wild-type plants treated with increasing ozone concentrations. This can be explained by a physiological compensation response within the transgenic line to counteract the ozone damage.

TABLE 2

Increased ozone tolerance of Arabidopsis thaliana plants over-expressing the yeast nicotineamidase (Pnc1) gene.

| | 250 ppb $O_3$ | 350 ppb $O_3$ | 500 ppb $O_3$ |
|---|---|---|---|
| Wild-type | 45%* | 50% | 100% |
| Pnc1 | 20% | 25% | 100% |

*percentage of the plants exhibiting necrotic lesions

Furthermore, control plants, homozygous transgenic populations of plants comprising the chimeric Pnc1 gene as well as a heterozygous transgenic population, were subjected to ozone fumigations and scored for visible injury and various physiological responses compared to non-fumigated plants. The assessment included measurement of non-modulated fluorescence, modulated fluorescence, chlorophyll measurement and fresh weight determination.

Based on the visible injury and physiological responses, a ranking was made for each population indicating the degree of the ozone impact. The more negative the evaluation, the more sensitive the population's response to ozone.

Whereas the control non-transgenic population and the heterozygous transgenic population had a cumulative score of −13, the two homozygous transgenic populations had a score of −6 and −2 respectively. It is therefore clear that the homozygous transgenic populations performed statistically significantly better than the control plants.

The invention claimed is:

1. A method for obtaining a plant with increased stress resistance comprising
   a. introducing a chimeric gene into cells of a plant to obtain transgenic cells, said chimeric gene comprising the following operably linked DNA fragments:
      i. a plant-expressible promoter;
      ii. a DNA region coding for a nicotinamidase comprising the amino acid sequence of SEQ ID No.: 2;
      iii. a 3' end region involved in transcription termination and polyadenylation;
   b. regenerating said transgenic cells to obtain a population of transgenic plants; and
   c. selecting a plant from said population of transgenic plants which exhibits increased stress resistance, exhibits a reduced level of reactive oxygen species, or maintains a high level of NADH under stress conditions when compared to a similar non-transgenic plant.

2. The method according to claim 1, wherein said DNA region comprises the nucleotide sequence of SEQ ID No.: 1.

3. The method according to claim 1, further comprising the step of crossing said plant with another plant.

4. A chimeric gene comprising the following operably linked DNA fragments:
   (i) a plant-expressible promoter;
   (ii) a DNA region coding for a nicotinamidase comprising the amino acid sequence of SEQ ID No.: 2;
   (iii) a 3' end region involved in transcription termination and polyadenylation.

5. A plant cell comprising a chimeric gene as described in claim 4.

6. A plant comprising a chimeric gene as described in claim 4.

7. The plant of claim 6, wherein said plant is cotton, *Brassica* vegetables, oilseed rape, wheat, corn or maize, barley, sunflower, rice, oats, sugarcane, soybean, vegetables, chicory, lettuce, tomato, tobacco, potato, sugarbeet, papaya, pineapple, mango or *Arabidopsis thaliana*.

8. The plant according to claim 6 wherein said plant has a lower level of reactive oxygen species under stress conditions than a similar plant not comprising such a chimeric gene.

9. A seed of a plant according to claim 6, wherein said seed comprises a chimeric gene as described in claim 4.

10. A method of increasing the stress resistance of a plant comprising introducing the chimeric gene according to claim 4, thereby increasing the stress resistance of said plant.

11. A method of decreasing the level of reactive oxygen species or maintaining the level of NAD in a plant or plant cell under stress conditions comprising introducing the chimeric gene according to claim 4, thereby decreasing the level of reactive oxygen species or maintaining the level of NAD in said plant or plant cell.

12. The chimeric gene according to claim 4, wherein said DNA region comprises the nucleotide sequence of SEQ ID No.: 1.

13. The method according to claim 1, wherein said transgenic plants are single copy transgenic lines.

14. The plant according to claim 6, wherein said plant is a single copy transgenic line.

* * * * *

SEQUENCE LISTING

```
<160> NUMBER OF SEQ ID NOS: 34

<210> SEQ ID NO 1
<211> LENGTH: 651
<212> TYPE: DNA
<213> ORGANISM: Saccharomyces cerevisiae

<400> SEQUENCE: 1
atgaagactt taattgttgt tgatatgcaa aatgatttta tttcaccttt aggttccttg      60
actgttccaa aaggtgagga attaatcaat cctatctcgg atttgatgca agatgctgat     120
agagactggc acaggattgt ggtcaccaga gattggcacc cttccagaca tatttcgttc     180
gcaaagaacc ataaagataa agaaccctat tcaacataca cctaccactc tccaaggcca     240
ggcgatgatt ccacgcaaga gggtattttg tggcccgtac actgtgtgaa aaacacctgg     300
ggtagtcaat tggttgacca aataatggac caagtggtca ctaagcatat taagattgtc     360
gacaagggtt tcttgactga ccgtgaatac tactccgcct tccacgacat ctggaacttc     420
cataagaccg acatgaacaa gtacttagaa aagcatcata cagacgaggt ttacattgtc     480
ggtgtagctt tggagtattg tgtcaaagcc accgccattt ccgctgcaga actaggttat     540
aagaccactg tcctgctgga ttacacaaga cccatcagcg atgatcccga agtcatcaat     600
aaggttaagg aagagttgaa ggcccacaac atcaatgtcg tggataaata a              651

<210> SEQ ID NO 2
<211> LENGTH: 216
<212> TYPE: PRT
<213> ORGANISM: Saccharomyces cerevisiae
```

<400> SEQUENCE: 2

```
Met Lys Thr Leu Ile Val Val Asp Met Gln Asn Asp Phe Ile Ser Pro
1               5                  10                  15

Leu Gly Ser Leu Thr Val Pro Lys Gly Glu Glu Leu Ile Asn Pro Ile
            20                  25                  30

Ser Asp Leu Met Gln Asp Ala Asp Arg Asp Trp His Arg Ile Val Val
        35                  40                  45

Thr Arg Asp Trp His Pro Ser Arg His Ile Ser Phe Ala Lys Asn His
    50                  55                  60

Lys Asp Lys Glu Pro Tyr Ser Thr Tyr Thr Tyr His Ser Pro Arg Pro
65                  70                  75                  80

Gly Asp Asp Ser Thr Gln Glu Gly Ile Leu Trp Pro Val His Cys Val
                85                  90                  95

Lys Asn Thr Trp Gly Ser Gln Leu Val Asp Gln Ile Met Asp Gln Val
            100                 105                 110

Val Thr Lys His Ile Lys Ile Val Asp Lys Gly Phe Leu Thr Asp Arg
        115                 120                 125

Glu Tyr Tyr Ser Ala Phe His Asp Ile Trp Asn Phe His Lys Thr Asp
    130                 135                 140

Met Asn Lys Tyr Leu Glu Lys His His Thr Asp Glu Val Tyr Ile Val
145                 150                 155                 160

Gly Val Ala Leu Glu Tyr Cys Val Lys Ala Thr Ala Ile Ser Ala Ala
                165                 170                 175

Glu Leu Gly Tyr Lys Thr Thr Val Leu Leu Asp Tyr Thr Arg Pro Ile
            180                 185                 190

Ser Asp Asp Pro Glu Val Ile Asn Lys Val Lys Glu Glu Leu Lys Ala
        195                 200                 205

His Asn Ile Asn Val Val Asp Lys
    210                 215
```

<210> SEQ ID NO 3
<211> LENGTH: 1290
<212> TYPE: DNA
<213> ORGANISM: Saccharomyces cerevisiae

<400> SEQUENCE: 3

```
ttaggtccat ctgtgcgctt cgttatcacc actccaactt cgttcagtat atcccaattc      60
ctctttcact ctcttcacag tggcaggatc tcccatattt ttacctaagt tatcagaaat     120
tttgatagcg tgattaccat ttacttctaa tagtttgata acgatgttta acggctcact     180
tttaacctgg ggttctgact tcttacgaaa tcattagta aagtttgtgc caataccgaa      240
tgtggctagc attccattct ctttagctgc atgggagtaa gttattgcct tttcgacgtt     300
caaagaatcg gaataacaga taatcttcga gaatttaggc aatttcaaca cgtcatggta     360
atggtgggaa atctttttgg tatactcaac tgggtctcca gaatcttgtc taacaccgac     420
gtaagcatca gaatatggtg gacggaatga ttttaaaaag tcatcagttc aaaagtatc      480 cgttaatgct aaaccagcat tttttgcacc aaaagtattg atccaacaat ccattgcatt     540
tttattggca tgcaaataat cttcactaat agaagcgact cccataaccc actcgtgagc     600
cacagtaccg attggcttga ctccatattt cttggcaaat aaaatatttg atgtgcctaa     660
taatagcgat ttgttttctgt ctgggttacc gttcacagct ttcatgattc cttgcataat     720
tagatcttga gccttcagag atctcgacg tcttgtacca aattcactga atctaatacc     780
attatcaaac aaagtttccg ccttcttctc agcttgttct aattggtttt cgtagtccca     840
```

-continued

```
gtcgatgtca acaaatttaa aatacgcttc tgatattagg gacagtaagg ggatctcata    900
aaggatagta tccttccaac taccactgac taaaattttc aatttgtagt gggtgggctt    960
gccctcgatt tcttctgaag tgaaggaaat ctgctcttca gggtgtagtt tgtaattaga   1020
actgctaata tacttaatat atgccgatgg caaatatggg atttcctgtt ttaagtattc   1080
aatttcctct tctgtgaacc tcaaatttcc caaatacgaa aattgctctt tcaaccaatt   1140
aatggcttcc ttattgaagg tcaattggga cgacctgttg gtatatttat aagtaactgt   1200
aacatctgga aaattagtga agacagcagc atgcatcgta atcttgtaca tgtctgtgtc   1260
caaaagagac tttatcactg gttctgacat                                    1290
```

<210> SEQ ID NO 4
<211> LENGTH: 429
<212> TYPE: PRT
<213> ORGANISM: Saccharomyces cerevisiae

<400> SEQUENCE: 4

```
Met Ser Glu Pro Val Ile Lys Ser Leu Leu Asp Thr Asp Met Tyr Lys
1               5                   10                  15

Ile Thr Met His Ala Ala Val Phe Thr Asn Phe Pro Asp Val Thr Val
            20                  25                  30

Thr Tyr Lys Tyr Thr Asn Arg Ser Ser Gln Leu Thr Phe Asn Lys Glu
        35                  40                  45

Ala Ile Asn Trp Leu Lys Glu Gln Phe Ser Tyr Leu Gly Asn Leu Arg
    50                  55                  60

Phe Thr Glu Glu Ile Glu Tyr Leu Lys Gln Glu Ile Pro Tyr Leu
65                  70                  75                  80

Pro Ser Ala Tyr Ile Lys Tyr Ile Ser Ser Asn Tyr Lys Leu His
            85                  90                  95

Pro Glu Glu Gln Ile Ser Phe Thr Ser Glu Glu Ile Glu Gly Lys Pro
        100                 105                 110

Thr His Tyr Lys Leu Lys Ile Leu Val Ser Gly Ser Trp Lys Asp Thr
    115                 120                 125

Ile Leu Tyr Glu Ile Pro Leu Leu Ser Leu Ile Ser Glu Ala Tyr Phe
130                 135                 140

Lys Phe Val Asp Ile Asp Trp Asp Tyr Glu Asn Gln Leu Glu Gln Ala
145                 150                 155                 160

Glu Lys Lys Ala Glu Thr Leu Phe Asp Asn Gly Ile Arg Phe Ser Glu
            165                 170                 175

Phe Gly Thr Arg Arg Arg Arg Ser Leu Lys Ala Gln Asp Leu Ile Met
        180                 185                 190

Gln Gly Ile Met Lys Ala Val Asn Gly Asn Pro Asp Arg Asn Lys Ser
    195                 200                 205

Leu Leu Leu Gly Thr Ser Asn Ile Leu Phe Ala Lys Lys Tyr Gly Val
210                 215                 220

Lys Pro Ile Gly Thr Val Ala His Glu Trp Val Met Gly Val Ala Ser
225                 230                 235                 240

Ile Ser Glu Asp Tyr Leu His Ala Asn Lys Asn Ala Met Asp Cys Trp
            245                 250                 255

Ile Asn Thr Phe Gly Ala Lys Asn Ala Gly Leu Ala Leu Thr Asp Thr
        260                 265                 270

Phe Gly Thr Asp Asp Phe Leu Lys Ser Phe Arg Pro Pro Tyr Ser Asp
    275                 280                 285
```

| | | | | | | | | | | |
|---|---|---|---|---|---|---|---|---|---|---|
| Ala | Tyr | Val | Gly | Val | Arg | Gln | Asp | Ser | Gly | Asp | Pro | Val | Glu | Tyr | Thr |
| | 290 | | | | 295 | | | | 300 | |

Lys Lys Ile Ser His His Tyr His Asp Val Leu Lys Leu Pro Lys Phe
305 310 315 320

Ser Lys Ile Ile Cys Tyr Ser Asp Ser Leu Asn Val Glu Lys Ala Ile
 325 330 335

Thr Tyr Ser His Ala Ala Lys Glu Asn Gly Met Leu Ala Thr Phe Gly
 340 345 350

Ile Gly Thr Asn Phe Thr Asn Asp Phe Arg Lys Lys Ser Glu Pro Gln
 355 360 365

Val Lys Ser Glu Pro Leu Asn Ile Val Ile Lys Leu Leu Glu Val Asn
 370 375 380

Gly Asn His Ala Ile Lys Ile Ser Asp Asn Leu Gly Lys Asn Met Gly
385 390 395 400

Asp Pro Ala Thr Val Lys Arg Val Lys Glu Glu Leu Gly Tyr Thr Glu
 405 410 415

Arg Ser Trp Ser Gly Asp Asn Glu Ala His Arg Trp Thr
 420 425

<210> SEQ ID NO 5
<211> LENGTH: 1206
<212> TYPE: DNA
<213> ORGANISM: Saccharomyces cerevisiae

<400> SEQUENCE: 5

```
atggatccca caagagctcc ggatttcaaa ccgccatctg cagacgagga attgattcct    60
ccacccgacc cggaatctaa aattcccaaa tctattccaa ttattccata cgtcttagcc   120
gatgcgaatt cctctataga tgcaccttct aatattaaga ggaagaaaaa gcatcctaag   180
catcatcatc accatcatca cagtcgtaaa gaaggcaatg ataaaaaaca tcagcatatt   240
ccattgaacc aagacgactt caaccacctt tccgcagaaa tgtcttccga agatgatgac   300
gcggatttta gatccaagga gagatacggt tcagattcaa ccacagaatc agaaactaga   360
ggtgttcaga aatatcagat tgctgattta agaagaagttc cacatggaat cgttcgtcaa   420
gcaagaacct tggaagacta cgaattcccc tcacacagat tatcgaaaaa attactggat   480
ccaaataaac tgccgttagt aatagtagca tgtgggtctt ttccaccaat cacctacttg   540
catctaagaa tgtttgaaat ggctttagat gcaatctctg aacaaacaag gtttgaagtc   600
ataggtggat attactcccc tgttagtgat aactatcaaa agcaaggctt ggccccatcc   660
taccatagag tacgtatgtg tgaattggcc tgcgaaagaa cctcatcttg gttgatggtg   720
gatgcatggg agtcattgca accttcatac acaagaactg ccaaggtctt ggatcatttc   780
aatcacgaaa tcaatattaa gagaggtggt gtagctactg ttactggaga aaaaattggt   840
gtgaaaataa tgttgctggc tggtggtgac ctaatagagt caatgggtga accaaacgtt   900
tgggcggacg ccgatttaca tcacattctc ggtaattacg gttgtttgat tgtcgaacgt   960
actggttctg atgtaaggtc ttttttgtta tcccatgata ttatgtatga acatagaagg  1020
aatattctta tcatcaagca actcatctat aatgatattt cttccacgaa agttcgtcta  1080
tttatcagac gcgccatgtc tgtacaatat ttgttaccta attcggtcat caggtatatc  1140
caagaacata gactatatgt ggaccaaacc gaacctgtta agcaagttct tggaaacaaa  1200
gaatga                                                             1206
```

<210> SEQ ID NO 6

<211> LENGTH: 401
<212> TYPE: PRT
<213> ORGANISM: Saccharomyces cerevisiae

<400> SEQUENCE: 6

```
Met Asp Pro Thr Arg Ala Pro Asp Phe Lys Pro Pro Ser Ala Asp Glu
 1               5                  10                  15

Glu Leu Ile Pro Pro Asp Pro Glu Ser Lys Ile Pro Lys Ser Ile
             20                  25                  30

Pro Ile Ile Pro Tyr Val Leu Ala Asp Ala Asn Ser Ser Ile Asp Ala
             35                  40                  45

Pro Phe Asn Ile Lys Arg Lys Lys His Pro Lys His His His His
 50                  55                  60

His His His Ser Arg Lys Glu Gly Asn Asp Lys Lys His Gln His Ile
 65                  70                  75                  80

Pro Leu Asn Gln Asp Asp Phe Gln Pro Leu Ser Ala Glu Val Ser Ser
                 85                  90                  95

Glu Asp Asp Asp Ala Asp Phe Arg Ser Lys Glu Arg Tyr Gly Ser Asp
                100                 105                 110

Ser Thr Thr Glu Ser Glu Thr Arg Gly Val Gln Lys Tyr Gln Ile Ala
            115                 120                 125

Asp Leu Glu Glu Val Pro His Gly Ile Val Arg Gln Ala Arg Thr Leu
130                 135                 140

Glu Asp Tyr Glu Phe Pro Ser His Arg Leu Ser Lys Lys Leu Leu Asp
145                 150                 155                 160

Pro Asn Lys Leu Pro Leu Val Ile Val Ala Cys Gly Ser Phe Ser Pro
                165                 170                 175

Ile Thr Tyr Leu His Leu Arg Met Phe Glu Met Ala Leu Asp Ala Ile
            180                 185                 190

Ser Glu Gln Thr Arg Phe Glu Val Ile Gly Gly Tyr Tyr Ser Pro Val
        195                 200                 205

Ser Asp Asn Tyr Gln Lys Gln Gly Leu Ala Pro Ser Tyr His Arg Val
210                 215                 220

Arg Met Cys Glu Leu Ala Cys Glu Arg Thr Ser Ser Trp Leu Met Val
225                 230                 235                 240

Asp Ala Trp Glu Ser Leu Gln Pro Ser Tyr Thr Arg Thr Ala Lys Val
                245                 250                 255

Leu Asp His Phe Asn His Glu Ile Asn Ile Lys Arg Gly Gly Val Ala
            260                 265                 270

Thr Val Thr Gly Glu Lys Ile Gly Val Lys Ile Met Leu Leu Ala Gly
        275                 280                 285

Gly Asp Leu Ile Glu Ser Met Gly Glu Pro Asn Val Trp Ala Asp Ala
290                 295                 300

Asp Leu His His Ile Leu Gly Asn Tyr Gly Cys Leu Ile Val Glu Arg
305                 310                 315                 320

Thr Gly Ser Asp Val Arg Ser Phe Leu Leu Ser His Asp Ile Met Tyr
                325                 330                 335

Glu His Arg Arg Asn Ile Leu Ile Lys Gln Leu Ile Tyr Asn Asp
            340                 345                 350

Ile Ser Ser Thr Lys Val Arg Leu Phe Ile Arg Arg Ala Met Ser Val
        355                 360                 365

Gln Tyr Leu Leu Pro Asn Ser Val Ile Arg Tyr Ile Gln Glu His Arg
370                 375                 380

Leu Tyr Val Asp Gln Thr Glu Pro Val Lys Gln Val Leu Gly Asn Lys
```

-continued

```
385                 390                 395                 400
Glu

<210> SEQ ID NO 7
<211> LENGTH: 1188
<212> TYPE: DNA
<213> ORGANISM: Saccharomyces cerevisiae

<400> SEQUENCE: 7
atggatccca ccaaagcacc cgattttaaa ccgccacagc caaatgaaga actacaacca      60
ccgccagatc caacacatac gataccaaaa tctggaccca tagttccata tgttttagct     120
gattataatt cttcgatcga tgctcctttc aatctcgaca tttacaaaac cctgtcgtca     180
aggaaaaaaa acgccaactc aagcaaccga atggaccata ttccattaaa tactagtgac     240
ttccagccac tatctcggga tgtatcatcg gaggaggaaa gtgaagggca atcgaatgga     300
attgacgcta ctctcaggat gttacgatg actgggaatt ggggggtact gaagagccaa      360
attgctgatt ggaagaagt tcctcacaca attgtaagac aagccagaac tattgaagat      420
tacgaatttc ctgtacacag attgacgaaa agttacaag atcctgaaaa actgcctctg      480
atcatcgttg cttgtggatc attttctccc ataacatacc tacatttgag aatgtttgaa     540
atggctttag atgatatcaa tgagcaaacg cgttttgaag tggttggtgg ttattttctc     600
ccagtaagtg ataactatca aaagcgaggg ttagccccag cttatcatcg tgtccgcatg     660
tgcgaattag catgcgagcg acatcatct tggttaatgg ttgatgcctg ggaatcttta      720
caatcaagtt atacaaggac agcaaaagtc ttggaccatt caatcatga ataaatatc       780
aagagaggtg gaatcatgac tgtagatggt gaaaaaatgg gcgtaaaaat catgttattg     840
gcaggcggtg atcttatcga atccatgggc gagcctcatg tgtgggctga ttcagacctg     900
caccatattt tgggtaatta tggatgtttg atcgtggaaa ggactggttc tgatgttagg     960
tccttcttgc tttcccatga tatcatgtat gaacacagaa gaaatatcct tattatcaaa    1020
caacttattt acaatgatat ttcctctacg aaagtgcggc ttttcatcag acgtggaatg    1080
tcagttcaat atcttcttcc aaactctgtc atccgttaca tccaagagta taatctatac    1140
attaatcaaa gtgaaccggt caagcaggtc ttggatagca aagagtga               1188

<210> SEQ ID NO 8
<211> LENGTH: 395
<212> TYPE: PRT
<213> ORGANISM: Saccharomyces cerevisiae

<400> SEQUENCE: 8

Met Asp Pro Thr Lys Ala Pro Asp Phe Lys Pro Gln Pro Asn Glu
1               5                   10                  15

Glu Leu Gln Pro Pro Asp Pro Thr His Thr Ile Pro Lys Ser Gly
                20                  25                  30

Pro Ile Val Pro Tyr Val Leu Ala Asp Tyr Asn Ser Ser Ile Asp Ala
            35                  40                  45

Pro Phe Asn Leu Asp Ile Tyr Lys Thr Leu Ser Ser Arg Lys Lys Asn
        50                  55                  60

Ala Asn Ser Ser Asn Arg Met Asp His Ile Pro Leu Asn Thr Ser Asp
65                  70                  75                  80

Phe Gln Pro Leu Ser Arg Asp Val Ser Glu Glu Ser Glu Gly
                85                  90                  95

Gln Ser Asn Gly Ile Asp Ala Thr Leu Gln Asp Val Thr Met Thr Gly
```

```
              100                 105                 110
Asn Leu Gly Val Leu Lys Ser Gln Ile Ala Asp Leu Glu Glu Val Pro
            115                 120                 125
His Thr Ile Val Arg Gln Ala Arg Thr Ile Glu Asp Tyr Glu Phe Pro
            130                 135                 140
Val His Arg Leu Thr Lys Lys Leu Gln Asp Pro Glu Lys Leu Pro Leu
145                 150                 155                 160
Ile Ile Val Ala Cys Gly Ser Phe Ser Pro Ile Thr Tyr Leu His Leu
                165                 170                 175
Arg Met Phe Glu Met Ala Leu Asp Asp Ile Asn Glu Gln Thr Arg Phe
            180                 185                 190
Glu Val Val Gly Gly Tyr Phe Ser Pro Val Ser Asp Asn Tyr Gln Lys
            195                 200                 205
Arg Gly Leu Ala Pro Ala Tyr His Arg Val Arg Met Cys Glu Leu Ala
            210                 215                 220
Cys Glu Arg Thr Ser Ser Trp Leu Met Val Asp Ala Trp Glu Ser Leu
225                 230                 235                 240
Gln Ser Ser Tyr Thr Arg Thr Ala Lys Val Leu Asp His Phe Asn His
                245                 250                 255
Glu Ile Asn Ile Lys Arg Gly Gly Ile Met Thr Val Asp Gly Glu Lys
            260                 265                 270
Met Gly Val Lys Ile Met Leu Leu Ala Gly Gly Asp Leu Ile Glu Ser
            275                 280                 285
Met Gly Glu Pro His Val Trp Ala Asp Ser Leu His His Ile Leu
            290                 295                 300
Gly Asn Tyr Gly Cys Leu Ile Val Glu Arg Thr Gly Ser Asp Val Arg
305                 310                 315                 320
Ser Phe Leu Leu Ser His Asp Ile Met Tyr Glu His Arg Arg Asn Ile
                325                 330                 335
Leu Ile Ile Lys Gln Leu Ile Tyr Asn Asp Ile Ser Ser Thr Lys Val
            340                 345                 350
Arg Leu Phe Ile Arg Arg Gly Met Ser Val Gln Tyr Leu Leu Pro Asn
            355                 360                 365
Ser Val Ile Arg Tyr Ile Gln Glu Tyr Asn Leu Tyr Ile Asn Gln Ser
            370                 375                 380
Glu Pro Val Lys Gln Val Leu Asp Ser Lys Glu
385                 390                 395

<210> SEQ ID NO 9
<211> LENGTH: 2145
<212> TYPE: DNA
<213> ORGANISM: Saccharomyces cerevisiae

<400> SEQUENCE: 9
atgtcacatc ttatcacttt agctacatgc aacttgaatc aatgggccct agattttgaa      60
ggtaatagag accgtatcct acagtccatt aagattgcca agagagggg tgccaggtta     120 cgtgtcggcc cagaactgga ataactggc tacggatgtt tagatcattt tttagaaaat     180
gacgtttgcc ttcattcatg ggaaatgtat gctcaaatca ttaagaataa agaaacccat     240
ggattaatac ttgacattgg tatgcccgtt ctacacaaga atgttcgtta taattgtcgt     300 tgttatcct tggatggtga gatattgttc ataagaccta agatttggtt agctaatgat     360
ggtaactata gggaaatgag attttttcaca ccttggatga aacctggcgt ggtgaggac     420 tttatccttc cacctgagat tcagaaagtt accggccaga gacttgtgcc atttggggac     480
```

```
gctgtgataa attcattgga tacatgcatt ggtacagaaa cttgtgaaga attgtttaca    540
cctcaatccc cccacatcgc catgtcttta gatggtgtgg aaatcatgac aaactcatct    600
ggttctcatc atgaactgcg taagttaaat aaaaggttag acctaatttt aaatgccact    660
aaacgttgtg gtggtgttta cttgtatgca aatcaaagag gttgtgatgg tgacagatta    720
tattatgatg ctgtgcact  aattgccatc aatggtacaa ttgtagccca aggttcacaa    780
ttttcgctag atgatgtgga agtagttact gctactgtgg acctagaaga ggtgaggagt    840
tatcgtgcag ctgtcatgtc tcgtggccta caagcctcct tggcagaaat aaagttcaag    900
cgtattgata ttcctgtaga attggcttta atgacctcca gatttgatcc tacagtgtgt    960
ccaacaaaag tccgcgagcc tttctatcac tctcctgagg aagaaattgc actgggacct   1020
gcttgctgga tgtgggatta tttaagacgt tgtaacggaa cagggttttt ccttcccttta  1080 tctgggggca ttgactcttg tgcaactgca atgattgtcc actctatgtg ccgtttagtg   1140
accgacgctg ctcaaaatgg aaatgagcaa gttatcaaag acgttcgtaa gataacacgt   1200
agcggcgatg attggattcc agacagtcca caggatctag cctcaaaaat atttcactcc   1260
tgtttcatgg gtacggaaaa ttcatccaag gagacaagaa acagagcaaa ggaccttcc    1320 aatgcaattg gatcttacca cgtggattta aagatggact cattggtatc cagtgtggtg   1380
tccttattcg aagtagccac tggcaaaaaa ccaatataca aaatatttgg gggatctcaa   1440
atcgagaact tggctttaca aaacatccag gcgcgtctaa gaatggttct ttcttatctt   1500
tttgcgcaac tgttgccgtg ggttcgtggt atcccaaact cgggtggatt gttagtactt   1560
ggtagcgcaa atgttgatga gtgcttacgt gggtatctaa caaaatatga ctgctcctcc   1620
gcagatatca accctattgg gggtatttca aaaactgact tgaaaagatt cattgcctac   1680
gcatcaaaac aatataacat gccaatcttg aatgactttt taaacgctac accaactgca   1740
gaattagaac ctatgactaa agattacgtt caatcggatg agatagatat ggggatgacg   1800
tatgaagaat tgggcgtgtt tggttaccta agaaaggttg aaaaatgtgg tccttattct   1860
atgttcttaa aacttcttca tcaatggtcc ccaaagttaa cacctcgtca aatatctgaa   1920
aaggtgaaaa gattttctctt cttctatgcc atcaacagac acaagcaaac tgttttaact  1980
cctagttatc atgctgaaca gtattcacca gaagacaaca gatttgactt acgtcctttc   2040
ttaatcaacc caagatttcc atgggcttca agaaaaattg atgaagttgt cgagcagtgt   2100
gaagcacata aaggctcaac gcttgacatt atgtctattg attag                   2145
```

<210> SEQ ID NO 10
<211> LENGTH: 714
<212> TYPE: PRT
<213> ORGANISM: Saccharomyces cerevisiae

<400> SEQUENCE: 10

```
Met Ser His Leu Ile Thr Leu Ala Thr Cys Asn Leu Asn Gln Trp Ala
1               5                   10                  15

Leu Asp Phe Glu Gly Asn Arg Asp Arg Ile Leu Gln Ser Ile Lys Ile
            20                  25                  30

Ala Lys Glu Arg Gly Ala Arg Leu Arg Val Gly Pro Glu Leu Glu Ile
        35                  40                  45

Thr Gly Tyr Gly Cys Leu Asp His Phe Leu Glu Asn Asp Val Cys Leu
    50                  55                  60

His Ser Trp Glu Met Tyr Ala Gln Ile Ile Lys Asn Lys Glu Thr His
65                  70                  75                  80
```

-continued

```
Gly Leu Ile Leu Asp Ile Gly Met Pro Val Leu His Lys Asn Val Arg
                 85                  90                  95
Tyr Asn Cys Arg Leu Leu Ser Leu Asp Gly Glu Ile Leu Phe Ile Arg
            100                 105                 110
Pro Lys Ile Trp Leu Ala Asn Asp Gly Asn Tyr Arg Glu Met Arg Phe
        115                 120                 125
Phe Thr Pro Trp Met Lys Pro Gly Val Val Glu Asp Phe Ile Leu Pro
    130                 135                 140
Pro Glu Ile Gln Lys Val Thr Gly Gln Arg Leu Val Pro Phe Gly Asp
145                 150                 155                 160
Ala Val Ile Asn Ser Leu Asp Thr Cys Ile Gly Thr Glu Thr Cys Glu
                165                 170                 175
Glu Leu Phe Thr Pro Gln Ser Pro His Ile Ala Met Ser Leu Asp Gly
            180                 185                 190
Val Glu Ile Met Thr Asn Ser Ser Gly Ser His His Glu Leu Arg Lys
        195                 200                 205
Leu Asn Lys Arg Leu Asp Leu Ile Leu Asn Ala Thr Lys Arg Cys Gly
    210                 215                 220
Gly Val Tyr Leu Tyr Ala Asn Gln Arg Gly Cys Asp Gly Asp Arg Leu
225                 230                 235                 240
Tyr Tyr Asp Gly Cys Ala Leu Ile Ala Ile Asn Gly Thr Ile Val Ala
                245                 250                 255
Gln Gly Ser Gln Phe Ser Leu Asp Asp Val Glu Val Val Thr Ala Thr
            260                 265                 270
Val Asp Leu Glu Glu Val Arg Ser Tyr Arg Ala Ala Val Met Ser Arg
        275                 280                 285
Gly Leu Gln Ala Ser Leu Ala Glu Ile Lys Phe Lys Arg Ile Asp Ile
    290                 295                 300
Pro Val Glu Leu Ala Leu Met Thr Ser Arg Phe Asp Pro Thr Val Cys
305                 310                 315                 320
Pro Thr Lys Val Arg Glu Pro Phe Tyr His Ser Pro Glu Glu Ile
                325                 330                 335
Ala Leu Gly Pro Ala Cys Trp Met Trp Asp Tyr Leu Arg Arg Cys Asn
            340                 345                 350
Gly Thr Gly Phe Phe Leu Pro Leu Ser Gly Ile Asp Ser Cys Ala
        355                 360                 365
Thr Ala Met Ile Val His Ser Met Cys Arg Leu Val Thr Asp Ala Ala
    370                 375                 380
Gln Asn Gly Asn Glu Gln Val Ile Lys Asp Val Arg Lys Ile Thr Arg
385                 390                 395                 400
Ser Gly Asp Asp Trp Ile Pro Asp Ser Pro Gln Asp Leu Ala Ser Lys
                405                 410                 415
Ile Phe His Ser Cys Phe Met Gly Thr Glu Asn Ser Ser Lys Glu Thr
            420                 425                 430
Arg Asn Arg Ala Lys Asp Leu Ser Asn Ala Ile Gly Ser Tyr His Val
        435                 440                 445
Asp Leu Lys Met Asp Ser Leu Val Ser Ser Val Ser Leu Phe Glu
    450                 455                 460
Val Ala Thr Gly Lys Lys Pro Ile Tyr Lys Ile Phe Gly Gly Ser Gln
465                 470                 475                 480
Ile Glu Asn Leu Ala Leu Gln Asn Ile Gln Ala Arg Leu Arg Met Val
                485                 490                 495
```

-continued

Leu Ser Tyr Leu Phe Ala Gln Leu Leu Pro Trp Val Arg Gly Ile Pro
            500                 505                 510

Asn Ser Gly Gly Leu Leu Val Leu Gly Ser Ala Asn Val Asp Glu Cys
            515                 520                 525

Leu Arg Gly Tyr Leu Thr Lys Tyr Asp Cys Ser Ser Ala Asp Ile Asn
            530                 535                 540

Pro Ile Gly Gly Ile Ser Lys Thr Asp Leu Lys Arg Phe Ile Ala Tyr
545                 550                 555                 560

Ala Ser Lys Gln Tyr Asn Met Pro Ile Leu Asn Asp Phe Leu Asn Ala
            565                 570                 575

Thr Pro Thr Ala Glu Leu Glu Pro Met Thr Lys Asp Tyr Val Gln Ser
            580                 585                 590

Asp Glu Ile Asp Met Gly Met Thr Tyr Glu Glu Leu Gly Val Phe Gly
            595                 600                 605

Tyr Leu Arg Lys Val Glu Lys Cys Gly Pro Tyr Ser Met Phe Leu Lys
            610                 615                 620

Leu Leu His Gln Trp Ser Pro Lys Leu Thr Pro Arg Gln Ile Ser Glu
625                 630                 635                 640

Lys Val Lys Arg Phe Phe Phe Tyr Ala Ile Asn Arg His Lys Gln
            645                 650                 655

Thr Val Leu Thr Pro Ser Tyr His Ala Glu Gln Tyr Ser Pro Glu Asp
            660                 665                 670

Asn Arg Phe Asp Leu Arg Pro Phe Leu Ile Asn Pro Arg Phe Pro Trp
            675                 680                 685

Ala Ser Arg Lys Ile Asp Glu Val Val Glu Gln Cys Glu Ala His Lys
            690                 695                 700

Gly Ser Thr Leu Asp Ile Met Ser Ile Asp
705                 710

<210> SEQ ID NO 11
<211> LENGTH: 597
<212> TYPE: DNA
<213> ORGANISM: Arabidopsis thaliana

<400> SEQUENCE: 11
atggcttcct catcaacgag aaagtacgag acacgaaagc gagatccaaa ctctaaaatc      60
gcagctcttc tcgttatcga catgcagaat cacttctcct ccatggccaa acccatcctc     120
aacaacgttc tcaccaccat cgacatctgc cgacgcgcct cagtcccgt attctttacg      180 cgtcacaacc acaaatcccc gaccgaccac ggcatgctcg gcgagtggtg taacggcgat     240
gtaatccttg acggaaccac cgattctgaa atcatccagg agatacaagg ccaagtaacc     300
ggaccagacg agatggtgga gaagaacacg tacagtgcgt taacaaaaac ccgcctccag     360
gaaaacctgg aaaagatcgg agtaaaggag gtgatcgtga tcggagtgat gacgaacttg     420
tgctgtgaga caacggcgcg tgaagcgttt attaagggtt tagggttttt tttctcgacg     480
gacgcgactg cgacgtttaa tgaggagctt cacgaggcta cgctaatgaa tctcgctttt     540
ggcttcgctt atctcgtcga ttgcgataaa ctccggcgaa gtctactcgg taactaa       597

<210> SEQ ID NO 12
<211> LENGTH: 198
<212> TYPE: PRT
<213> ORGANISM: Arabidopsis thaliana

<400> SEQUENCE: 12

Met Ala Ser Ser Ser Thr Arg Lys Tyr Glu Thr Arg Lys Arg Asp Pro

```
                1               5                  10                 15
Asn Ser Lys Ile Ala Ala Leu Leu Val Ile Asp Met Gln Asn His Phe
            20                  25                 30

Ser Ser Met Ala Lys Pro Ile Leu Asn Asn Val Leu Thr Thr Ile Asp
            35                  40                 45

Ile Cys Arg Arg Ala Ser Val Pro Val Phe Phe Thr Arg His Asn His
            50                  55                 60

Lys Ser Pro Thr Asp His Gly Met Leu Gly Glu Trp Cys Asn Gly Asp
65                      70                 75                    80

Val Ile Leu Asp Gly Thr Thr Asp Ser Glu Ile Ile Gln Glu Ile Gln
                85                  90                 95

Gly Gln Val Thr Gly Pro Asp Glu Met Val Glu Lys Asn Thr Tyr Ser
            100                 105                110

Ala Phe Asn Lys Thr Arg Leu Gln Glu Asn Leu Glu Lys Ile Gly Val
            115                 120                125

Lys Glu Val Ile Val Ile Gly Val Met Thr Asn Leu Cys Cys Glu Thr
            130                 135                140

Thr Ala Arg Glu Ala Phe Ile Lys Gly Phe Arg Val Phe Phe Ser Thr
145                     150                155                   160

Asp Ala Thr Ala Thr Phe Asn Glu Glu Leu His Glu Ala Thr Leu Met
                165                 170                175

Asn Leu Ala Phe Gly Phe Ala Tyr Leu Val Asp Cys Asp Lys Leu Arg
            180                 185                190

Arg Ser Leu Leu Gly Asn
            195

<210> SEQ ID NO 13
<211> LENGTH: 597
<212> TYPE: DNA
<213> ORGANISM: Arabidopsis thaliana

<400> SEQUENCE: 13
atggcttctt catcatcgag aacgtacgag acacgaaagc gagagccaaa tcctaaaatc      60
gcagctcttc tcgtcatcga tatgcagaat cacttctact ctatggctga accaatcctc     120
caaaacgctc tcaccaccat cgacatctgc cgacgcgctt caatccccgt attcttcacg     180
cgccacaacc acaaatcccc aaccgaccac ggcatgctcg gagagtggtg gaacggcgat     240
ctaatcctcg acggaaccac tgattccgaa atcatcccgg aaatcaatcg ccaggtcacc     300
ggaccagacg aaatcgtgga agagcacg tacagtgcgt taacaacac gcaccttcag      360 gagaagctgg acaagatcgg agtgaaggag gtgatcgtta tcggagtgat gacgaaccta     420
tgctgtgaga cgacggcgcg tgaagcgttt gtaaagggg ttagggtttt tttctcgacg      480
gacgcgactg cgacggttaa tgaagagctt cacgaggcta ctctaatgaa tctcgcgtat     540
ggctttgctt atctcgtcga ttgcgataga ctccggcgag gtctactcag tagttaa       597

<210> SEQ ID NO 14
<211> LENGTH: 198
<212> TYPE: PRT
<213> ORGANISM: Arabidopsis thaliana

<400> SEQUENCE: 14

Met Ala Ser Ser Ser Arg Thr Tyr Glu Thr Arg Lys Arg Glu Pro
1               5                  10                 15

Asn Pro Lys Ile Ala Ala Leu Leu Val Ile Asp Met Gln Asn His Phe
            20                  25                 30
```

Tyr Ser Met Ala Glu Pro Ile Leu Gln Asn Ala Leu Thr Thr Ile Asp
             35                  40                  45

Ile Cys Arg Arg Ala Ser Ile Pro Val Phe Phe Thr Arg His Asn His
 50                  55                  60

Lys Ser Pro Thr Asp His Gly Met Leu Gly Glu Trp Trp Asn Gly Asp
 65                  70                  75                  80

Leu Ile Leu Asp Gly Thr Thr Asp Ser Glu Ile Pro Glu Ile Asn
                 85                  90                  95

Arg Gln Val Thr Gly Pro Asp Glu Ile Val Glu Lys Ser Thr Tyr Ser
                100                 105                 110

Ala Phe Asn Asn Thr His Leu Gln Glu Lys Leu Asp Lys Ile Gly Val
            115                 120                 125

Lys Glu Val Ile Val Ile Gly Val Met Thr Asn Leu Cys Cys Glu Thr
            130                 135                 140

Thr Ala Arg Glu Ala Phe Val Lys Gly Phe Arg Val Phe Phe Ser Thr
145                 150                 155                 160

Asp Ala Thr Ala Thr Val Asn Glu Glu Leu His Glu Ala Thr Leu Met
                165                 170                 175

Asn Leu Ala Tyr Gly Phe Ala Tyr Leu Val Asp Cys Asp Arg Leu Arg
            180                 185                 190

Arg Gly Leu Leu Ser Ser
        195

<210> SEQ ID NO 15
<211> LENGTH: 591
<212> TYPE: DNA
<213> ORGANISM: Arabidopsis thaliana

<400> SEQUENCE: 15
atggccgaga gatggaggaa cacggctcta ctcgtcatcg acatgcagaa cgatttcata      60
gaggaaggtg ctgtgacgca agtgaaagga ggaaaatcta tagttcctaa tgttatcaga     120
gtcgtcgaac tcgcgaggca gcgtggtatt ctcgtaattt gggttgttcg agaacatgat     180
cgtcaaggaa gagatgttga attattcagg cgccataact acagttctga aaagtcggg      240 ccagttatta aaggcaccgt aggagcagaa ttggttgatg gattgatgat caacgaagaa     300
gatgactata agattgtgaa aactcgtttc agtgctttct ttagtaccaa tcttcattcc     360
ttcttgcaaa cttcaggggt taccaagtta gtgattgctg gtgtgcaaac gccgaactgt     420
atccggcaaa cggtgtttga tgcagtggcg ctggattatc ccaatgtgac tgttattaca     480
gatgccacag ctgctgcaac accagagatc catactgcga atattcttga catgaagaat     540
attggagtca agactcctac attacacgag tggtccgaag aacttgcttg a              591

<210> SEQ ID NO 16
<211> LENGTH: 196
<212> TYPE: PRT
<213> ORGANISM: Arabidopsis thaliana

<400> SEQUENCE: 16

Met Ala Glu Arg Trp Arg Asn Thr Ala Leu Leu Val Ile Asp Met Gln
 1                5                  10                  15

Asn Asp Phe Ile Glu Glu Gly Ala Val Thr Gln Val Lys Gly Gly Lys
                 20                  25                  30

Ser Ile Val Pro Asn Val Ile Arg Val Val Glu Leu Ala Arg Gln Arg
             35                  40                  45

```
Gly Ile Leu Val Ile Trp Val Val Arg Glu His Asp Arg Gln Gly Arg
 50                  55                  60

Asp Val Glu Leu Phe Arg Arg His Asn Tyr Ser Ser Glu Lys Val Gly
 65                  70                  75                  80

Pro Val Ile Lys Gly Thr Val Gly Ala Glu Leu Val Asp Gly Leu Met
                 85                  90                  95

Ile Asn Glu Glu Asp Asp Tyr Lys Ile Val Lys Thr Arg Phe Ser Ala
                100                 105                 110

Phe Phe Ser Thr Asn Leu His Ser Phe Leu Gln Thr Ser Gly Val Thr
            115                 120                 125

Lys Leu Val Ile Ala Gly Val Gln Thr Pro Asn Cys Ile Arg Gln Thr
130                 135                 140

Val Phe Asp Ala Val Ala Leu Asp Tyr Pro Asn Val Thr Val Ile Thr
145                 150                 155                 160

Asp Ala Thr Ala Ala Thr Pro Glu Ile His Thr Ala Asn Ile Leu
                165                 170                 175

Asp Met Lys Asn Ile Gly Val Lys Thr Pro Thr Leu His Glu Trp Ser
            180                 185                 190

Glu Glu Leu Ala
        195

<210> SEQ ID NO 17
<211> LENGTH: 1680
<212> TYPE: DNA
<213> ORGANISM: Arabidopsis thaliana

<400> SEQUENCE: 17
atggagaaga aagaaaatgg tctcgatgga aagcaatcgg gtcgggtcat taacggaccc      60
actaacccga tggtcacacc tctgctcaac gatctttacc aattcaccat ggcttatgct     120
tattggaaag ctggcaaaca atctgagcga tctgtgtttg atctgtatttt cgtaagaat    180 ccttttggtg gagaatacac tatctttgct ggtttagaag aatgcatcaa atttctcgct     240
aatttcaatt tgactgatga agagatcgat ttcgttcgtg attcgttacc tggatgtgag     300
gaagctttct gtgattatct tcgagggctt gattgttctg acattgaagt gtatgccatt     360
tcggaaggat cagttgtttt tcctaaagtt cctttactca gaatcgaagg tcctgttgct     420
gtggtgcaat tgttggaaac tccattcctc aatctcatca attacgcatc tttggttgct     480
acaaatgcag caagacatcg gtttgttgca ggaaaatcta agcttctgct tgagtttggt     540
gctagaagag ctcagggacc cgatggtgca ataagcgcat caaagtattg ctaccttgga     600
ggttttgatg caacaagtaa tgttgcagcg ggaaaactgt ttgggatacc cctccgtggt     660
actcattccc atgcttttgt tagctcattc atgagccttg atgaaattgt tgacaaagtg     720
cttcgaagtt ctgatgggaa aagcacttgt aaggatttta tatgtttggt ccaaacttgc     780
ctaacaaaga ttcagaattc atcttcatta caaggaattt tttccgagac aaatcaaagc     840
gagcttgcag cgttcatttc atatgcactg gcattcccaa actcctttct cgctcttgta     900
gacacttatg atgtgatgaa gagtggtatt ccaaacttct gtgctgttgc tctagcactt     960
aatgaattgg gatacaaagc agtaggcatt agactggatt caggtgactt agcctatctt    1020
tctactgagg tcaggaaatt cttttgtgcc atagagagag acctcaaagt tcctgatttc    1080
gggaagatga tcgtcactgc tagtaacgat ctaaacgaag agacagtcga tgctctaaat    1140
aaacagggtc atgaagtaga tgcatttgga attggaaacca acttagtgac ttgctatgcg    1200
caagctgcgt taggttgtgt tttcaaactt gtggaaataa acaatcagcc tcggatcaaa    1260
```

```
ctttctgaag atgttactaa ggtatcgatt ccatgtaaaa agcgtactta cagattgttc   1320 ggaaagagg gttaccctct tgttgatata atgactggag agaacgaacc acctccaaag    1380
gtcggtgaaa ggttactttg ccgtcatcca ttcaatgaat caaaaagggc ttatgtggtt   1440
ccacaacgcg ttgaagagct tctgaaatgt tattggcgtg gcaatgcaga tgaagctagg   1500
gaagagctag agccattgaa agagctaaga aatcgttgca tcaaacagct cgaaaatatg   1560
cgacccgatc atatgagaag attaaaccct actccttata aggttagtgt cagcgccaag   1620
ttgtatgact tcatccactt cctctggctc aacgaagctc ctgtcggtga actgcattga   1680
```

<210> SEQ ID NO 18
<211> LENGTH: 559
<212> TYPE: PRT
<213> ORGANISM: Arabidopsis thaliana

<400> SEQUENCE: 18

```
Met Glu Lys Lys Glu Asn Gly Leu Asp Gly Lys Gln Ser Gly Arg Val
1               5                   10                  15

Ile Asn Gly Pro Thr Asn Pro Met Val Thr Pro Leu Leu Asn Asp Leu
            20                  25                  30

Tyr Gln Phe Thr Met Ala Tyr Ala Tyr Trp Lys Ala Gly Lys Gln Ser
        35                  40                  45

Glu Arg Ser Val Phe Asp Leu Tyr Phe Arg Lys Asn Pro Phe Gly Gly
    50                  55                  60

Glu Tyr Thr Ile Phe Ala Gly Leu Glu Glu Cys Ile Lys Phe Leu Ala
65                  70                  75                  80

Asn Phe Asn Leu Thr Asp Glu Glu Ile Asp Phe Val Arg Asp Ser Leu
                85                  90                  95

Pro Gly Cys Glu Glu Ala Phe Cys Asp Tyr Leu Arg Gly Leu Asp Cys
            100                 105                 110

Ser Asp Ile Glu Val Tyr Ala Ile Ser Glu Gly Ser Val Val Phe Pro
        115                 120                 125

Lys Val Pro Leu Leu Arg Ile Glu Gly Pro Val Ala Val Val Gln Leu
    130                 135                 140

Leu Glu Thr Pro Phe Leu Asn Leu Ile Asn Tyr Ala Ser Leu Val Ala
145                 150                 155                 160

Thr Asn Ala Ala Arg His Arg Phe Val Ala Gly Lys Ser Lys Leu Leu
                165                 170                 175

Leu Glu Phe Gly Ala Arg Arg Ala Gln Gly Pro Asp Gly Ala Ile Ser
            180                 185                 190

Ala Ser Lys Tyr Cys Tyr Leu Gly Gly Phe Asp Ala Thr Ser Asn Val
        195                 200                 205

Ala Ala Gly Lys Leu Phe Gly Ile Pro Leu Arg Gly Thr His Ser His
    210                 215                 220

Ala Phe Val Ser Ser Phe Met Ser Leu Asp Glu Ile Val Asp Lys Val
225                 230                 235                 240

Leu Arg Ser Ser Asp Gly Lys Ser Thr Cys Lys Asp Phe Ile Cys Leu
                245                 250                 255

Val Gln Thr Cys Leu Thr Lys Ile Gln Asn Ser Ser Ser Leu Gln Gly
            260                 265                 270

Ile Phe Ser Glu Thr Asn Gln Ser Glu Leu Ala Ala Phe Ile Ser Tyr
        275                 280                 285

Ala Leu Ala Phe Pro Asn Ser Phe Leu Ala Leu Val Asp Thr Tyr Asp
    290                 295                 300
```

Val Met Lys Ser Gly Ile Pro Asn Phe Cys Ala Val Ala Leu Ala Leu
305                 310                 315                 320

Asn Glu Leu Gly Tyr Lys Ala Val Gly Ile Arg Leu Asp Ser Gly Asp
                325                 330                 335

Leu Ala Tyr Leu Ser Thr Glu Val Arg Lys Phe Phe Cys Ala Ile Glu
                340                 345                 350

Arg Asp Leu Lys Val Pro Asp Phe Gly Lys Met Ile Val Thr Ala Ser
                355                 360                 365

Asn Asp Leu Asn Glu Glu Thr Val Asp Ala Leu Asn Lys Gln Gly His
                370                 375                 380

Glu Val Asp Ala Phe Gly Ile Gly Thr Asn Leu Val Thr Cys Tyr Ala
385                 390                 395                 400

Gln Ala Ala Leu Gly Cys Val Phe Lys Leu Val Glu Ile Asn Asn Gln
                405                 410                 415

Pro Arg Ile Lys Leu Ser Glu Asp Val Thr Lys Val Ser Ile Pro Cys
                420                 425                 430

Lys Lys Arg Thr Tyr Arg Leu Phe Gly Lys Glu Gly Tyr Pro Leu Val
                435                 440                 445

Asp Ile Met Thr Gly Glu Asn Glu Pro Pro Lys Val Gly Glu Arg
450                 455                 460

Leu Leu Cys Arg His Pro Phe Asn Glu Ser Lys Arg Ala Tyr Val Val
465                 470                 475                 480

Pro Gln Arg Val Glu Glu Leu Leu Lys Cys Tyr Trp Arg Gly Asn Ala
                485                 490                 495

Asp Glu Ala Arg Glu Glu Leu Glu Pro Leu Lys Glu Leu Arg Asn Arg
                500                 505                 510

Cys Ile Lys Gln Leu Glu Asn Met Arg Pro Asp His Met Arg Arg Leu
                515                 520                 525

Asn Pro Thr Pro Tyr Lys Val Ser Val Ser Ala Lys Leu Tyr Asp Phe
                530                 535                 540

Ile His Phe Leu Trp Leu Asn Glu Ala Pro Val Gly Glu Leu His
545                 550                 555

<210> SEQ ID NO 19
<211> LENGTH: 1674
<212> TYPE: DNA
<213> ORGANISM: Arabidopsis thaliana

<400> SEQUENCE: 19
atggagccga agagaacgg ctcagaattg ggtcagaaga tcattgacgg accaacgaat      60
ccaatggtca cacctttact caatgatctt tatcaattca ccatggctta tgcttattgg     120
aaagctggca acacaacga cgatccgtt ttcgatctgt attttcgtaa gaacccattt       180
ggtggtgagt acactgtgtt tgctggatta gaagagtgtg ttaagttctt agccaatttc     240
aaattgactg atgaagaaat cgatttcgtt caagagtgtt tgcctggatc tgaggaagct     300
ttttgtgatt atcttagagg gcttgattgt tctgatgttg aagtttatgc aattccggaa     360
ggatcagttg ttttttccta agtacctctc atgagagttg aaggacctgt tggtgttgtt     420
caattgttgg aaactccatt cctcaatctt gtcaattttg catctttggt agctactaac     480
gcagctaggc atcgctttgt tgccggaaaa tctaagagtc tactcgagtt tggtgctcga     540
agggctcagg gtccgatgg tgcaataagc gcatcaaaat attgctacct tggaggtttt     600
gatgcaacaa gtaatgtagc agctggaaaa cttttttggga ttcctcttcg tggaacacac     660

-continued

```
tctcatgctt atgttagctc attcatgagt actgatgaga ttgttgacaa agtacttcgt    720
agtgctgatg ggaaaaccac gtgcgaggat tttgttagtc atgttcagac atggttaaaa    780
aagattcagt attcaccatc tctaagtggc attttctctg agacaaatca aagcgagcta    840
gcagctttca cctcatatgc actggcattc cccaaaactt ttcttgccct cgtagataca    900
tacgatgtga tgaagagtgg aatccctaac ttctgtgcag ttgctttagc actcaatgac    960
tttggatata aagcattagg tattagactg gattcaggtg atttagctta tctatctaga   1020
gaggccagaa atttcttctg cacggtagag agagaactaa aagtgcctgg ttttgggaag   1080
atggtcgtca ctgctagtaa tgatctaaat gaagagacga ttgacgcttt aaataaacag   1140
ggacatgagg tggatgcttt tggcatcggg acctacttgg tcacttgcta ttcacaagcg   1200
gccttaggtt gcgttttcaa acttgtggag ataaacaatc agcctcggat taaactttct   1260
gaagatgtta caaaggtatc aataccgtgt aaaaagcgaa gttacagatt atacggcaaa   1320
gaaggttacc ctctggtaga tataatgact ggagagaacg aaccacctcc aaaggttggt   1380
gagcgtttac tttgtcgtca cccattcaac gaatccaaaa agcatatgt agtgccacaa   1440
cgtgtcgaag agctcctcaa atgttattgg cgtggaagtg cagatgaagc aagagaagta   1500
ttaccgcctt tgaaagagat aagagaccgt tgcatcaaac agctcgaaaa catgcgacct   1560
gatcatatga ggagattaaa cccaactcct tataaggtta gtgtaagcgc aaagctgtac   1620
gatttcatcc acttcttatg gctaaacgaa gcacctgttg gtgaattgca gtga         1674
```

<210> SEQ ID NO 20
<211> LENGTH: 557
<212> TYPE: PRT
<213> ORGANISM: Arabidopsis thaliana

<400> SEQUENCE: 20

```
Met Glu Pro Lys Glu Asn Gly Ser Glu Leu Gly Gln Lys Ile Ile Asp
1               5                   10                  15

Gly Pro Thr Asn Pro Met Val Thr Pro Leu Leu Asn Asp Leu Tyr Gln
            20                  25                  30

Phe Thr Met Ala Tyr Ala Tyr Trp Lys Ala Gly Lys His Asn Glu Arg
        35                  40                  45

Ser Val Phe Asp Leu Tyr Phe Arg Lys Asn Pro Phe Gly Gly Glu Tyr
    50                  55                  60

Thr Val Phe Ala Gly Leu Glu Glu Cys Val Lys Phe Leu Ala Asn Phe
65                  70                  75                  80

Lys Leu Thr Asp Glu Glu Ile Asp Phe Val Gln Glu Cys Leu Pro Gly
                85                  90                  95

Ser Glu Glu Ala Phe Cys Asp Tyr Leu Arg Gly Leu Asp Cys Ser Asp
            100                 105                 110

Val Glu Val Tyr Ala Ile Pro Glu Gly Ser Val Val Phe Pro Lys Val
        115                 120                 125

Pro Leu Met Arg Val Glu Gly Pro Val Gly Val Gln Leu Leu Glu
    130                 135                 140

Thr Pro Phe Leu Asn Leu Val Asn Phe Ala Ser Leu Val Ala Thr Asn
145                 150                 155                 160

Ala Ala Arg His Arg Phe Val Ala Gly Lys Ser Lys Ser Leu Leu Glu
                165                 170                 175

Phe Gly Ala Arg Arg Ala Gln Gly Pro Asp Gly Ala Ile Ser Ala Ser
            180                 185                 190

Lys Tyr Cys Tyr Leu Gly Gly Phe Asp Ala Thr Ser Asn Val Ala Ala
```

```
                195                 200                 205
Gly Lys Leu Phe Gly Ile Pro Leu Arg Gly Thr His Ser His Ala Tyr
            210                 215                 220

Val Ser Ser Phe Met Ser Thr Asp Glu Ile Val Asp Lys Val Leu Arg
225                 230                 235                 240

Ser Ala Asp Gly Lys Thr Thr Cys Glu Asp Phe Val Ser His Val Gln
            245                 250                 255

Thr Trp Leu Lys Lys Ile Gln Tyr Ser Pro Ser Leu Ser Gly Ile Phe
            260                 265                 270

Ser Glu Thr Asn Gln Ser Glu Leu Ala Ala Phe Thr Ser Tyr Ala Leu
            275                 280                 285

Ala Phe Pro Lys Thr Phe Leu Ala Leu Val Asp Thr Tyr Asp Val Met
            290                 295                 300

Lys Ser Gly Ile Pro Asn Phe Cys Ala Val Ala Leu Ala Leu Asn Asp
305                 310                 315                 320

Phe Gly Tyr Lys Ala Leu Gly Ile Arg Leu Asp Ser Gly Asp Leu Ala
            325                 330                 335

Tyr Leu Ser Arg Glu Ala Arg Asn Phe Phe Cys Thr Val Glu Arg Glu
            340                 345                 350

Leu Lys Val Pro Gly Phe Gly Lys Met Val Val Thr Ala Ser Asn Asp
            355                 360                 365

Leu Asn Glu Glu Thr Ile Asp Ala Leu Asn Lys Gln Gly His Glu Val
            370                 375                 380

Asp Ala Phe Gly Ile Gly Thr Tyr Leu Val Thr Cys Tyr Ser Gln Ala
385                 390                 395                 400

Ala Leu Gly Cys Val Phe Lys Leu Val Glu Ile Asn Asn Gln Pro Arg
            405                 410                 415

Ile Lys Leu Ser Glu Asp Val Thr Lys Val Ser Ile Pro Cys Lys Lys
            420                 425                 430

Arg Ser Tyr Arg Leu Tyr Gly Lys Glu Gly Tyr Pro Leu Val Asp Ile
            435                 440                 445

Met Thr Gly Glu Asn Glu Pro Pro Lys Val Gly Glu Arg Leu Leu
450                 455                 460

Cys Arg His Pro Phe Asn Glu Ser Lys Arg Ala Tyr Val Val Pro Gln
465                 470                 475                 480

Arg Val Glu Glu Leu Leu Lys Cys Tyr Trp Arg Gly Ser Ala Asp Glu
            485                 490                 495

Ala Arg Glu Val Leu Pro Pro Leu Lys Glu Ile Arg Asp Arg Cys Ile
            500                 505                 510

Lys Gln Leu Glu Asn Met Arg Pro Asp His Met Arg Arg Leu Asn Pro
            515                 520                 525

Thr Pro Tyr Lys Val Ser Val Ser Ala Lys Leu Tyr Asp Phe Ile His
            530                 535                 540

Phe Leu Trp Leu Asn Glu Ala Pro Val Gly Glu Leu Gln
545                 550                 555

<210> SEQ ID NO 21
<211> LENGTH: 717
<212> TYPE: DNA
<213> ORGANISM: Arabidopsis thaliana

<400> SEQUENCE: 21
atggatgtcc cgttaccagt cgagaaatta tcttatggat caaacactga ggacaaaact      60
tgtgtagtgc ttgtggcaac tgggagtttc aatcctccta ctttcatgca tttacgcatg     120
```

-continued

```
tttgagctgg cgagagatga attacgctca aaaggatttc atgttcttgg aggatatatg    180
tctcctgtta atgatgcata taagaagaag ggccttttat ctgcagaaca tcgtttagag    240
atgtgtaatg tatcatgtca agctctgac tttgtaatgg ttgatccgtg ggaggcatct     300
caaagcaact accaacgaac tttgacggtt ttatcaaggg tcaagacttt cttaacaaca    360
aatcgacatg tacccgagga atctctcaaa gtcatgctac tatgtggctc ggatttactg    420
ctatctttct gcactcccgg tgtttggatc cctgaacagt taagaactat ttgcaaagat    480
tatggcattg tgtgcatccg tagagaagga caagatgttg aaaatatgat ctctggtgac    540
gaaatcttaa acgaaaactg tgctaacgtc aaaatcgttg acaatactgt tcctaatcaa    600
atcagttcga gtagattaag gcaatgcatt tcgcgagggt tatcggttaa atacttgact    660
gaagatggag taatagatta tatcagacaa catcaactat acactgagct cacatga      717
```

<210> SEQ ID NO 22
<211> LENGTH: 238
<212> TYPE: PRT
<213> ORGANISM: Arabidopsis thaliana

<400> SEQUENCE: 22

```
Met Asp Val Pro Leu Pro Val Glu Lys Leu Ser Tyr Gly Ser Asn Thr
1               5                   10                  15

Glu Asp Lys Thr Cys Val Val Leu Val Ala Thr Gly Ser Phe Asn Pro
            20                  25                  30

Pro Thr Phe Met His Leu Arg Met Phe Glu Leu Ala Arg Asp Glu Leu
        35                  40                  45

Arg Ser Lys Gly Phe His Val Leu Gly Gly Tyr Met Ser Pro Val Asn
    50                  55                  60

Asp Ala Tyr Lys Lys Lys Gly Leu Leu Ser Ala Glu His Arg Leu Glu
65                  70                  75                  80

Met Cys Asn Val Ser Cys Gln Ser Ser Asp Phe Val Met Val Asp Pro
                85                  90                  95

Trp Glu Ala Ser Gln Ser Asn Tyr Gln Arg Thr Leu Thr Val Leu Ser
            100                 105                 110

Arg Val Lys Thr Phe Leu Thr Thr Asn Arg His Val Pro Glu Glu Ser
        115                 120                 125

Leu Lys Val Met Leu Leu Cys Gly Ser Asp Leu Leu Leu Ser Phe Cys
    130                 135                 140

Thr Pro Gly Val Trp Ile Pro Glu Gln Leu Arg Thr Ile Cys Lys Asp
145                 150                 155                 160

Tyr Gly Ile Val Cys Ile Arg Arg Glu Gly Gln Asp Val Glu Asn Met
                165                 170                 175

Ile Ser Gly Asp Glu Ile Leu Asn Glu Asn Cys Ala Asn Val Lys Ile
            180                 185                 190

Val Asp Asn Thr Val Pro Asn Gln Ile Ser Ser Arg Leu Arg Gln
        195                 200                 205

Cys Ile Ser Arg Gly Leu Ser Val Lys Tyr Leu Thr Glu Asp Gly Val
    210                 215                 220

Ile Asp Tyr Ile Arg Gln His Gln Leu Tyr Thr Glu Leu Thr
225                 230                 235
```

<210> SEQ ID NO 23
<211> LENGTH: 2178
<212> TYPE: DNA
<213> ORGANISM: Arabidopsis thaliana

<400> SEQUENCE: 23

```
atgaggctgt tgaaggttgc tacgtgtaac ttgaaccaat gggccatgga tttcgagagc      60
aacatgaaga acatcaaggc ttcgatcgct gaggcaaagg ctgctggtgc tgttatcagg     120
cttggacccg agctcgaggt cactggctat ggttgcgagg atcacttctt ggaactcgac     180
actgtcactc atgcgtggga gtgtttgaag gaattgctgc ttggtgattg gacggatgat     240
attttgtgca gcataggaat gcctgtgatt aaggagcag agcgttataa ctgccaggtt      300
ctctgtatga acagaagaat catcatgatt cgaccgaaaa tgtggctcgc aaacgatgga     360
aactataggg agctacggtg gttcacagct tggaagcaga gagaagagct agaggaattt     420
cagctcccca ttgaaatttc agaggctttg agcagaaat cagtcccttt tggttatggt      480
tacatccagt ttatcgacac ggctgttgca gctgaagtct gtgaggaact gtttagtcca     540
cttcctcctc atgccgagct cgcattgaat ggtgttgaag tatttatgaa tgcaagtggg     600
agtcatcacc aacttaggaa actagatatt cgtctgaatg cttttatggg ggctactcat     660
gctcgtggtg gggtgtatat gtacagtaat caacaaggat gcgatggtag ccgcttatac     720
tacgatggat gtgcatgtat tgttgtaaac gggaatgttg ttgctcaagg ctcacaattc     780
tcgttgagag acgttgaggt catcatttca caagtggatc ttgatgcggt tgctagcctt     840
cgtggatcta taagtagctt tcaggaacaa gcaagctgca aggttaaagt atcttcagta     900
gctgtgccct gtagacttac acagtccttc aacctgaaaa tgacactaag cagtccgaag     960
aagatcattt accactctcc acaagaagaa atagcctttg gtcccgcttg ctggatgtgg    1020
gactatttga gaagaagtgg cgcttcagga tttttgcttc ctctttctgg cggagcagac    1080
agctcctccg tggcagctat tgttggctgc atgtgccaac ttgttgttaa agagattgca    1140
aagggagatg agcaagtaaa agctgatgcg aaccgaattg ggaattatgc taatgggcag    1200
tttcctactg atagcaaaga gtttgccaaa cgaatatttt acactgtctt tatgggttct    1260
gaaaacagtt ctgaggagac aaaaaggcgt tcaaagcagc tggcagacga gattggtgct    1320
tggcatcttg atgtttgcat agatggtgtt gtctctgcag ttttatcatt atttcaaaca    1380
gttacaggca agcgaccaag gtataaggtt gatggaggat caaatgctga aaccttggg     1440
ttgcagaaca ttcaagcccg gatgagaatg gtgttagcat ttatgttagc gtctctcttg    1500
ccttgggttc atagcaaacc aggcttttac cttgttctag gcagctccaa cgttgatgaa    1560
ggacttcgtg gttacctgac aaagtatgat tgcagctcag cagacataaa tcctatagga    1620
agtatcagta aaatggattt gaggttgttc ttaaaatggg ctgcaacgaa tctcggatat    1680
ccatccttgg cagagataga agctgctcca ccaacagctg agcttgagcc cattcgttct    1740
gactattctc agctcgatga agtcgacatg gaatgacat atgaagagct ttcagtctat     1800
ggaaggatga ggaagatatt ccgttgtgga ccagtatcta tgttcaagaa tctatgttac    1860
aagtggggaa caaagctaag cccagcagaa gtagctgaga agtgaagta tttcttcaaa     1920
tattattcga tcaatcgaca caaaatgact gtcctcacac cgtcttatca cgctgagagt    1980
tactccccag aggacaacag attcgatctg aggcagtttc tgtacaacag caagtggcca    2040
taccagttta agaagattga cgagattgtt gacagcttaa atggtgactc agttgctttc    2100
ccggaagaag aagcaaactc caacaaagaa attggagttg tagcagcaaa ctccggagac    2160
ccaagtgcgg gtctctga                                                  2178
```

<210> SEQ ID NO 24

<211> LENGTH: 725
<212> TYPE: PRT
<213> ORGANISM: Arabidopsis thaliana

<400> SEQUENCE: 24

```
Met Arg Leu Leu Lys Val Ala Thr Cys Asn Leu Asn Gln Trp Ala Met
1               5                   10                  15

Asp Phe Glu Ser Asn Met Lys Asn Ile Lys Ala Ser Ile Ala Glu Ala
            20                  25                  30

Lys Ala Ala Gly Ala Val Ile Arg Leu Gly Pro Glu Leu Glu Val Thr
        35                  40                  45

Gly Tyr Gly Cys Glu Asp His Phe Leu Glu Leu Asp Thr Val Thr His
    50                  55                  60

Ala Trp Glu Cys Leu Lys Glu Leu Leu Gly Asp Trp Thr Asp Asp
65                  70                  75                  80

Ile Leu Cys Ser Ile Gly Met Pro Val Ile Lys Gly Ala Glu Arg Tyr
                85                  90                  95

Asn Cys Gln Val Leu Cys Met Asn Arg Arg Ile Ile Met Ile Arg Pro
            100                 105                 110

Lys Met Trp Leu Ala Asn Asp Gly Asn Tyr Arg Glu Leu Arg Trp Phe
        115                 120                 125

Thr Ala Trp Lys Gln Arg Glu Glu Leu Glu Glu Phe Gln Leu Pro Ile
    130                 135                 140

Glu Ile Ser Glu Ala Leu Glu Gln Lys Ser Val Pro Phe Gly Tyr Gly
145                 150                 155                 160

Tyr Ile Gln Phe Ile Asp Thr Ala Val Ala Ala Glu Val Cys Glu Glu
                165                 170                 175

Leu Phe Ser Pro Leu Pro Pro His Ala Glu Leu Ala Leu Asn Gly Val
            180                 185                 190

Glu Val Phe Met Asn Ala Ser Gly Ser His His Gln Leu Arg Lys Leu
        195                 200                 205

Asp Ile Arg Leu Asn Ala Phe Met Gly Ala Thr His Ala Arg Gly Gly
    210                 215                 220

Val Tyr Met Tyr Ser Asn Gln Gln Gly Cys Asp Gly Ser Arg Leu Tyr
225                 230                 235                 240

Tyr Asp Gly Cys Ala Cys Ile Val Val Asn Gly Asn Val Val Ala Gln
                245                 250                 255

Gly Ser Gln Phe Ser Leu Arg Asp Val Glu Val Ile Ile Ser Gln Val
            260                 265                 270

Asp Leu Asp Ala Val Ala Ser Leu Arg Gly Ser Ile Ser Ser Phe Gln
    275                 280                 285

Glu Gln Ala Ser Cys Lys Val Lys Val Ser Ser Val Ala Val Pro Cys
290                 295                 300

Arg Leu Thr Gln Ser Phe Asn Leu Lys Met Thr Leu Ser Ser Pro Lys
305                 310                 315                 320

Lys Ile Ile Tyr His Ser Pro Gln Glu Glu Ile Ala Phe Gly Pro Ala
                325                 330                 335

Cys Trp Met Trp Asp Tyr Leu Arg Arg Ser Gly Ala Ser Gly Phe Leu
            340                 345                 350

Leu Pro Leu Ser Gly Gly Ala Asp Ser Ser Ser Val Ala Ala Ile Val
        355                 360                 365

Gly Cys Met Cys Gln Leu Val Val Lys Glu Ile Ala Lys Gly Asp Glu
    370                 375                 380

Gln Val Lys Ala Asp Ala Asn Arg Ile Gly Asn Tyr Ala Asn Gly Gln
```

```
                385                 390                 395                 400

Phe Pro Thr Asp Ser Lys Glu Phe Ala Lys Arg Ile Phe Tyr Thr Val
                        405                 410                 415

Phe Met Gly Ser Glu Asn Ser Ser Glu Glu Thr Lys Arg Arg Ser Lys
                        420                 425                 430

Gln Leu Ala Asp Glu Ile Gly Ala Trp His Leu Asp Val Cys Ile Asp
                        435                 440                 445

Gly Val Val Ser Ala Val Leu Ser Leu Phe Gln Thr Val Thr Gly Lys
                        450                 455                 460

Arg Pro Arg Tyr Lys Val Asp Gly Gly Ser Asn Ala Glu Asn Leu Gly
        465                 470                 475                 480

Leu Gln Asn Ile Gln Ala Arg Met Arg Met Val Leu Ala Phe Met Leu
                        485                 490                 495

Ala Ser Leu Leu Pro Trp Val His Ser Lys Pro Gly Phe Tyr Leu Val
                        500                 505                 510

Leu Gly Ser Ser Asn Val Asp Glu Gly Leu Arg Gly Tyr Leu Thr Lys
                        515                 520                 525

Tyr Asp Cys Ser Ser Ala Asp Ile Asn Pro Ile Gly Ser Ile Ser Lys
                        530                 535                 540

Met Asp Leu Arg Leu Phe Leu Lys Trp Ala Ala Thr Asn Leu Gly Tyr
        545                 550                 555                 560

Pro Ser Leu Ala Glu Ile Glu Ala Ala Pro Thr Ala Glu Leu Glu
                        565                 570                 575

Pro Ile Arg Ser Asp Tyr Ser Gln Leu Asp Glu Val Asp Met Gly Met
                        580                 585                 590

Thr Tyr Glu Glu Leu Ser Val Tyr Gly Arg Met Arg Lys Ile Phe Arg
                        595                 600                 605

Cys Gly Pro Val Ser Met Phe Lys Asn Leu Cys Tyr Lys Trp Gly Thr
                        610                 615                 620

Lys Leu Ser Pro Ala Glu Val Ala Glu Lys Val Lys Tyr Phe Phe Lys
        625                 630                 635                 640

Tyr Tyr Ser Ile Asn Arg His Lys Met Thr Val Leu Thr Pro Ser Tyr
                        645                 650                 655

His Ala Glu Ser Tyr Ser Pro Glu Asp Asn Arg Phe Asp Leu Arg Gln
                        660                 665                 670

Phe Leu Tyr Asn Ser Lys Trp Pro Tyr Gln Phe Lys Lys Ile Asp Glu
                        675                 680                 685

Ile Val Asp Ser Leu Asn Gly Asp Ser Val Ala Phe Pro Glu Glu Glu
                        690                 695                 700

Ala Asn Ser Asn Lys Glu Ile Gly Val Val Ala Ala Asn Ser Gly Asp
        705                 710                 715                 720

Pro Ser Ala Gly Leu
                        725

<210> SEQ ID NO 25
<211> LENGTH: 11811
<212> TYPE: DNA
<213> ORGANISM: Artificial
<220> FEATURE:
<223> OTHER INFORMATION: pTVE467

<400> SEQUENCE: 25
agattcgaag ctcggtcccg tgggtgttct gtcgtctcgt tgtacaacga aatccattcc      60
cattccgcgc tcaagatggc ttcccctcgg cagttcatca gggctaaatc aatctagccg     120
```

```
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggatttta gtactggatt ttggttttag gaattagaaa ttttattgat agaagtattt    360
tacaaataca aatacatact aagggtttct tatatgctca acacatgagc gaaaccctat    420 aggaaccccta attcccttat ctgggaacta ctcacacatt attatggaga aaatagagag    480
agatagattt gtagagagag actggtgatt tcagcgtgtc caagcttgct agcttattta    540
tccacgacat tgatgttgtg ggccttcaac tcttccttaa ccttattgat gacttcggga    600
tcatcgctga tgggtcttgt gtaatccagc aggacagtgg tcttataacc tagttctgca    660
gcggaaatgg cggtggcttt gacacaatac tccaaagcta caccgacaat gtaaacctcg    720
tctgtatgat gcttttctaa gtacttgttc atgtcggtct tatggaagtt ccagatgtcg    780
tggaaggcgg agtagtattc acggtcagtc aagaaaccct tgtcgacaat cttaatatgc    840
ttagtgacca cttggtccat tatttggtca accaattgac taccccaggt gttttcaca    900 cagtgtacgg gccacaaaat accctcttgc gtggaatcat cgcctggcct tggagagtgg    960
taggtgtatg ttgaataggg ttctttatct ttatggttct ttgcgaacga aatatgtctg   1020
gaagggtgcc aatctctggt gaccacaatc ctgtgccagt ctctatcagc atcttgcatc   1080
aaatccgaga taggattgat taattcctca ccttttggaa cagtcaagga acctaaaggt   1140
gaaataaaat cattttgcat atcaacaaca attaaagtct ccatggtttt ggtttaataa   1200
gaagagaaaa gagttctttt gttatggctg aagtaataga gaaatgagct cgagtcctct   1260
ccaaatgaaa tgaacttcct tatatagagg aagggtcttg cgaaggatag tgggattgtg   1320
cgtcatccct tacgtcagtg gagatatcac atcaatccac ttgctttgaa gacgtggttg   1380
gaacgtcttc ttttccacg atgctcctcg tgggtggggg tccatctttg ggaccactgt   1440
cggcagaggc atcttgaacg atagcctttc ctttatcgca atgatggcat ttgtaggtgc   1500
caccttcctt ttctactgtc cttttgatga agtgacagat agctgggcaa tggaatccga   1560
ggaggtttcc cgatattacc ctttgttgaa aagtctcaat agccctttgg tcttctgaga   1620
ctgtatcttt gatattcttg gagtagacga gagtgtcgtg ctccaccatg ttgacgaaga   1680
ttttcttctt gtcattgagt cgtaaaagac tctgtatgaa ctgttcgcca gtcttcacgg   1740
cgagttctgt tagatcctcg atctgaattt ttgactccat gtatggtgca tatggcgcgc   1800
catatgcccg ggccctgtac agcggccgcg ttaacgcgta tactctagag cgatcgcccg   1860
ggccggccat ttaaatgaat tcgagctcgg tacccaaacg cggccgcaag ctataacttc   1920
gtatagcata cattatacga agttattcga ctctagagga tcccaattcc catgcatgga   1980
gtcaaagatt caaatagagg acacttctcg aactcggccg tcgaactcgg ccgtcgagta   2040
catggtcgat aagaaaaggc aatttgtaga tgttaattcc catcttgaaa gaaatatagt   2100
ttaaatattt attgataaaa taacaagtca ggtattatag tccaagcaaa aacataaatt   2160
tattgatgca agtttaaatt cagaaatatt tcaataactg attatatcag ctggtacatt   2220
gccgtagatg aaagactgag tgcgatatta tgtgtaatac ataaattgat gatatagcta   2280
gcttagctca tcgggggatc ctagacgcgt gagatcagat ctcggtgacg ggcaggaccg   2340
gacggggcgg taccggcagg ctgaagtcca gctgccagaa acccacgtca tgccagttcc   2400
cgtgcttgaa gccggccgcc cgcagcatgc cgcgggggc atatccgagc gcctcgtgca   2460 tgccgcacgct cgggtcgttg ggcagcccga tgacagcgac cacgctcttg aagccctgtg   2520
```

```
cctccaggga cttcagcagg tgggtgtaga gcgtggagcc cagtcccgtc cgctggtggc    2580
ggggggagac gtacacggtc gactcggccg tccagtcgta ggcgttgcgt gccttccagg    2640
ggcccgcgta ggcgatgccg gcgacctcgc cgtccacctc ggcgacgagc cagggatagc    2700
gctcccgcag acggacgagg tcgtccgtcc actcctgcgg ttcctgcggc tcggtacgga    2760
agttgaccgt gcttgtctcg atgtagtggt tgacgatggt gcagaccgcc ggcatgtccg    2820
cctcggtggc acggcggatg tcggccgggc gtcgttctgg gtccattgtt cttctttact    2880
ctttgtgtga ctgaggtttg gtctagtgct ttggtcatct atatataatg ataacaacaa    2940
tgagaacaag ctttggagtg atcggagggt ctaggataca tgagattcaa gtggactagg    3000
atctacaccg ttggattttg agtgtggata tgtgtgaggt taattttact tggtaacggc    3060
cacaaaggcc taaggagagg tgttgagacc cttatcggct tgaaccgctg gaataatgcc    3120
acgtggaaga taattccatg aatcttatcg ttatctatga gtgaaattgt gtgatggtgg    3180
agtggtgctt gctcatttta cttgcctggt ggacttggcc ctttccttat ggggaattta    3240
tattttactt actatagagc tttcatacct tttttttacc ttggatttag ttaatatata    3300
atggtatgat tcatgaataa aaatgggaaa tttttgaatt tgtactgcta aatgcataag    3360
attaggtgaa actgtggaat atatatttt ttcatttaaa agcaaaattt gccttttact    3420
agaattataa atatagaaaa atatataaca ttcaaataaa aatgaaaata gaactttca    3480 aaaaacagaa ctatgtttaa tgtgtaaaga ttagtcgcac atcaagtcat ctgttacaat    3540
atgttacaac aagtcataag cccaacaaag ttagcacgtc taaataaact aaagagtcca    3600
cgaaaatatt acaaatcata agcccaacaa agttattgat caaaaaaaaa aaacgcccaa    3660
caaagctaaa caaagtccaa aaaaaacttc tcaagtctcc atcttccttt atgaacattg    3720
aaaactatac acaaaacaag tcagataaat ctctttctgg gcctgtcttc ccaacctcct    3780
acatcacttc cctatcggat tgaatgtttt acttgtacct tttccgttgc aatgatattg    3840
atagtatgtt tgtgaaaact aatagggtta acaatcgaag tcatggaata tggatttggt    3900
ccaagatttt ccgagagctt tctagtagaa agcccatcac cagaaattta ctagtaaaat    3960
aaatcaccaa ttaggtttct tattatgtgc caaattcaat ataattatag aggatatttc    4020
aaatgaaaac gtatgaatgt tattagtaaa tggtcaggta agacattaaa aaaatcctac    4080
gtcagatatt caactttaaa aattcgatca gtgtggaatt gtacaaaaat ttgggatcta    4140
ctatatatat ataatgcttt acaacacttg gatttttttt tggaggctgg aatttttaat    4200
ctacatattt gttttggcca tgcaccaact cattgtttag tgtaatactt tgattttgtc    4260
aaatatatgt gttcgtgtat atttgtataa gaatttcttt gaccatatac acacacacat    4320
atatatatat atatatatat tatatatcat gcacttttaa ttgaaaaaat aatatatata    4380
tatatagtgc atttttttcta acaaccatat atgttgcgat tgatctgcaa aaatactgct    4440
agagtaatga aaaatataat ctattgctga aattatctca gatgttaaga tttttcttaaa    4500 gtaaattctt tcaaattta gctaaaagtc ttgtaataac taaagaataa tacacaatct    4560
cgaccacgga aaaaaacac ataataaatt tgaatttcga ccgcggtacc cggaattggg    4620
ttataattac ctcaggtcga ggaattaatt cggtacgtac ctaataactt cgtatagcat    4680
acattatacg aagttatatg gatctcgagg cattacggca ttacggcact cgcgagggtc    4740
ccaattcgag catggagcca tttacaattg aatatatcct gccgccgctg ccgctttgca    4800
cccggtggag cttgcatgtt ggtttctacg cagaactgag ccggttaggc agataatttc    4860
```

```
cattgagaac tgagccatgt gcaccttccc cccaacacgg tgagcgacgg ggcaacggag    4920
tgatccacat gggactttta acatcatcc gtcggatggc gttgcgagag aagcagtcga     4980
tccgtgagat cagccgacgc accgggcagg cgcgcaacac gatcgcaaag tatttgaacg    5040
caggtacaat cgagccgacg ttcacggtac cggaacgacc aagcaagcta gcttagtaaa    5100
gccctcgcta gattttaatg cggatgttgc gattacttcg ccaactattg cgataacaag   5160
aaaaagccag cctttcatga tatatctccc aatttgtgta gggcttatta tgcacgctta   5220
aaaataataa aagcagactt gacctgatag tttggctgtg agcaattatg tgcttagtgc    5280
atctaacgct tgagttaagc cgcgccgcga agcggcgtcg gcttaacga attgttagac     5340 attatttgcc gactaccttg gtgatctcgc cttcacgta gtggacaaat tcttccaact    5400
gatctgcgcg cgaggccaag cgatcttctt cttgtccaag ataagcctgt ctagcttcaa    5460
gtatgacggg ctgatactgg gccggcaggc gctccattgc ccagtcggca gcgacatcct    5520
tcggcgcgat tttgccggtt actgcgctgt accaaatgcg ggacaacgta agcactacat    5580
ttcgctcatc gccagcccag tcgggcggcg agttccatag cgttaaggtt tcatttagcg    5640
cctcaaatag atcctgttca ggaaccggat caaagagttc ctccgccgct ggacctacca    5700
aggcaacgct atgttctctt gcttttgtca gcaagatagc cagatcaatg tcgatcgtgg    5760
ctggctcgaa gatacctgca agaatgtcat tgcgctgcca ttctccaaat tgcagttcgc    5820
gcttagctgg ataacgccac ggaatgatgt cgtcgtgcac aacaatggtg acttctacag    5880
cgcggagaat ctcgctctct ccaggggaag ccgaagtttc caaaaggtcg ttgatcaaag    5940
ctcgccgcgt tgtttcatca agccttacgg tcaccgtaac cagcaaatca atatcactgt    6000
gtggcttcag gccgccatcc actgcggagc cgtacaaatg tacggccagc aacgtcggtt    6060
cgagatggcg ctcgatgacg ccaactacct ctgatagttg agtcgatact tcggcgatca    6120
ccgcttccct catgatgttt aactttgttt tagggcgact gccctgctgc gtaacatcgt    6180
tgctgctcca taacatcaaa catcgaccca cggcgtaacg cgcttgctgc ttggatgccc    6240
gaggcataga ctgtaccca aaaaacagt cataacaagc catgaaaacc gccactgcgc      6300
cgttaccacc gctgcgttcg gtcaaggttc tggaccagtt gcgtgagcgc atacgctact    6360
tgcattacag cttacgaacc gaacaggctt atgtccactg ggttcgtgcc ttcatccgtt    6420
tccacggtgt gcgtcacccg gcaaccttgg gcagcagcga agtcgaggca tttctgtcct    6480
ggctggcgaa cgagcgcaag gtttcggtct ccacgcatcg tcaggcattg gcggccttgc    6540
tgttcttcta cggcaagtgc tgtgcacgga tctgccctgg cttcaggaga tcggaagacc    6600
tcggccgtcc gggcgcttgc cggtggtgct gaccccggat gaagtctcta gagctctaga   6660
gggttcgcat cctcggtttt ctggaaggcg agcatcgttt gttcgcccag cttctgtatg    6720
gaacgggcat gcggatcagt gagggtttgc aactgcgggt caaggatctg gatttcgatc    6780
acggcacgat catcgtgcgg gagggcaagg gctccaagga tcgggccttg atgttacccg    6840
agagcttggc acccagcctg cgcgagcagg gatcgatcca cccctccgc tgctatagtg     6900 cagtcggctt ctgacgttca gtgcagccgt cttctgaaaa cgacatgtcg cacaagtcct    6960
aagttacgcg acaggctgcc gccctgccct tttcctggcg ttttcttgtc gcgtgtttta    7020
gtcgcataaa gtagaatact tgcgactaga accggagaca ttacgccatg aacaagagcg    7080
ccgccgctgg cctgctgggc tatgcccgcg tcagcaccga cgaccaggac ttgaccaacc    7140
aacgggccga actgcacgcg gccggctgca ccaagctgtt ttccgagaag atcaccggca    7200
ccaggcgcga ccgcccggag ctggccagga tgcttgacca cctacgccct ggcgacgttg    7260
```

```
tgacagtgac caggctagac cgcctggccc gcagcacccg cgacctactg gacattgccg      7320
agcgcatcca ggaggccggc gcgggcctgc gtagcctggc agagccgtgg gccgacacca      7380
ccacgccggc cggccgcatg gtgttgaccg tgttcgccgg cattgccgag ttcgagcgtt      7440
ccctaatcat cgaccgcacc cggagcgggc gcgaggccgc caaggcccga ggcgtgaagt      7500
ttggcccccg ccctaccctc accccggcac agatcgcgca cgcccgcgag ctgatcgacc      7560
aggaaggccg caccgtgaaa gaggcggctg cactgcttgg cgtgcatcgc tcgaccctgt      7620
accgcgcact tgagcgcagc gaggaagtga cgcccaccga ggccaggcgg cgcggtgcct      7680
tccgtgagga cgcattgacc gaggccgacg ccctggcggc cgccgagaat gaacgccaag      7740
aggaacaagc atgaaaccgc accaggacgg ccaggacgaa ccgttttttca ttaccgaaga      7800 gatcgaggcg gagatgatcg cggccgggta cgtgttcgag ccgcccgcgc acgtctcaac      7860
cgtgcggctg catgaaatcc tggccggttt gtctgatgcc aagctggcgg cctggccggc      7920
cagcttggcc gctgaagaaa ccgagcgccg ccgtctaaaa aggtgatgtg tatttgagta      7980
aaacagcttg cgtcatgcgg tcgctgcgta tatgatgcga tgagtaaata acaaatacg       8040 caaggggaac gcatgaaggt tatcgctgta cttaaccaga aaggcgggtc aggcaagacg      8100
accatcgcaa cccatctagc ccgcgccctg caactcgccg gggccgatgt tctgttagtc      8160
gattccgatc cccagggcag tgcccgcgat tgggcggccg tgcgggaaga tcaaccgcta      8220
accgttgtcg gcatcgaccg cccgacgatt gaccgcgacg tgaaggccat cggccggcgc      8280
gacttcgtag tgatcgacgg agcgcccag gcggcggact tggctgtgtc cgcgatcaag      8340
gcagccgact tcgtgctgat tccggtgcag ccaagccctt acgacatatg gccaccgcc       8400 gacctggtgg agctggttaa gcagcgcatt gaggtcacgg atggaaggct acaagcggcc      8460
tttgtcgtgt cgcgggcgat caaaggcacg cgcatcggcg gtgaggttgc cgaggcgctg      8520
gccgggtacg agctgcccat tcttgagtcc cgtatcacgc agcgcgtgag ctacccaggc      8580
actgccgccg ccggcacaac cgttcttgaa tcagaacccg agggcgacgc tgcccgcgag      8640
gtccaggcgc tggccgctga aattaaatca aaactcattt gagttaatga ggtaaagaga      8700
aaatgagcaa aagcacaaac acgctaagtg ccggccgtcc gagcgcacgc agcagcaagg      8760
ctgcaacgtt ggccagcctg gcagacacgc cagccatgaa gcgggtcaac tttcagttgc      8820
cggcggagga tcacaccaag ctgaagatgt acgcggtacg ccaaggcaag accattaccg      8880
agctgctatc tgaatacatc gcgcagctac cagagtaaat gagcaaatga ataaatgagt      8940
agatgaattt tagcggctaa aggaggcggc atggaaaatc aagaacaacc aggcaccgac      9000
gccgtggaat gccccatgtg tggaggaacg ggcggttggc caggcgtaag cggctgggtt      9060
gtctgccggc cctgcaatgg cactggaacc cccaagcccg aggaatcggc gtgacggtcg      9120
caaaccatcc ggcccggtac aaatcggcgc ggcgctgggt gatgacctgg tgagaagtt       9180 gaaggccgcg caggccgccc agcggcaacg catcgaggca gaagcacgcc ccggtgaatc      9240
gtggcaagcg gccgctgatc gaatccgcaa agaatcccgg caaccgccgg cagccggtgc      9300
gccgtcgatt aggaagccgc ccaagggcga cgagcaacca gatttttcg ttccgatgct       9360 ctatgacgtg gcacccgcg atagtcgcag catcatggac gtggccgttt ccgtctgtc       9420 gaagcgtgac cgacgagctg gcgaggtgat ccgctacgag cttccagacg gcacgtaga       9480 ggtttccgca gggccggccg gcatggccag tgtgtgggat tacgacctgg tactgatggc      9540
ggtttcccat ctaaccgaat ccatgaaccg ataccgggaa gggaagggag acaagcccgg      9600
```

```
ccgcgtgttc cgtccacacg ttgcggacgt actcaagttc tgccggcgag ccgatggcgg      9660
aaagcagaaa gacgacctgg tagaaacctg cattcggtta acaccacgc acgttgccat       9720 gcagcgtacg aagaaggcca agaacggccg cctggtgacg gtatccgagg gtgaagcctt      9780
gattagccgc tacaagatcg taaagagcga aaccgggcgg ccggagtaca tcgagatcga      9840
gctagctgat tggatgtacc gcgagatcac agaaggcaag aacccggacg tgctgacggt      9900
tcaccccgat tactttttga tcgatcccgg catcggccgt tttctctacc gcctggcacg      9960
ccgcgccgca ggcaaggcag aagccagatg gttgttcaag acgatctacg aacgcagtgg     10020
cagcgccgga gagttcaaga agttctgttt caccgtgcgc aagctgatcg ggtcaaatga     10080
cctgccggag tacgatttga aggaggaggc ggggcaggct ggcccgatcc tagtcatgcg     10140
ctaccgcaac ctgatcgagg gcgaagcatc cgccggttcc taatgtacgg agcagatgct     10200
agggcaaatt gccctagcag gggaaaaagg tcgaaaaggt ctctttcctg tggatagcac     10260
gtacattggg aacccaaagc cgtacattgg gaaccggaac ccgtacattg gaacccaaa      10320 gccgtacatt gggaaccggt cacacatgta agtgactgat ataaagaga aaaaaggcga     10380 tttttccgcc taaaactctt taaaacttat taaaactctt aaaacccgcc tggcctgtgc     10440
ataactgtct ggccagcgca cagccgaaga gctgcaaaaa gcgcctaccc ttcggtcgct     10500
gcgctcccta cgccccgccg cttcgcgtcg gcctatcgcg gccgctggcc gctcaaaaat     10560
ggctggccta cggccaggca atctaccagg gcgcggacaa gccgcgccgt cgccactcga     10620
ccgccggcgc ccacatcaag gcaccctgcc tcgcgcgttt cggtgatgac ggtgaaaacc     10680
tctgacacat gcagctcccg gagacggtca cagcttgtct gtaagcggat gccgggagca     10740
gacaagcccg tcagggcgcg tcagcggtg ttggcgggtg tcgggcgca gccatgaccc       10800 agtcacgtag cgatagcgga gtgtatactg gcttaactat gcggcatcag agcagattgt     10860
actgagagtg caccatatgc ggtgtgaaat accgcacaga tgcgtaagga gaaaataccg     10920
catcaggcgc tcttccgctt cctcgctcac tgactcgctg cgctcggtcg ttcggctgcg     10980
gcgagcggta tcagctcact caaaggcggt aatacggtta ccacagaat cagggggataa      11040 cgcaggaaag aacatgtgag caaaaggcca gcaaaaggcc aggaaccgta aaaaggccgc     11100
gttgctggcg ttttcccata ggctccgccc cctgacgag catcacaaaa atcgacgctc      11160
aagtcagagg tggcgaaacc cgacaggact ataaagatac caggcgtttc ccccctggaag    11220 ctccctcgtg cgctctcctg ttccgaccct gccgcttacc ggatacctgt ccgcctttct    11280
cccttcggga agcgtggcgc tttctcatag ctcacgctgt aggtatctca gttcggtgta    11340
ggtcgttcgc tccaagctgg gctgtgtgca cgaaccccc gttcagcccg accgctgcgc      11400
cttatccggt aactatcgtc ttgagtccaa cccggtaaga cacgacttat cgccactggc    11460
agcagccact ggtaacagga ttagcagagc gaggtatgta ggcggtgcta cagagttctt    11520
gaagtggtgg cctaactacg gctacactag aaggacagta tttggtatct gcgctctgct    11580
gaagccagtt accttcggaa aaagagttgg tagctcttga tccggcaaac aaaccaccgc    11640
tggtagcggt ggtttttttg tttgcaagca gcagattacg cgcagaaaaa aaggatctca    11700
agaagatccg gaaaacgcaa gcgcaaagag aaagcaggta gcttgcagtg gcttacatg     11760 gcgatagcta gactgggcgg ttttatggac agcaagcgaa ccggaattgc c             11811
```

<210> SEQ ID NO 26
<211> LENGTH: 11829
<212> TYPE: DNA
<213> ORGANISM: Artificial
<220> FEATURE:
<223> OTHER INFORMATION: pTVE468

<400> SEQUENCE: 26

```
agattcgaag ctcggtcccg tgggtgttct gtcgtctcgt tgtacaacga aatccattcc      60
cattccgcgc tcaagatggc ttcccctcgg cagttcatca gggctaaatc aatctagccg     120
acttgtccgg tgaaatgggc tgcactccaa cagaaacaat caaacaaaca tacacagcga     180
cttattcaca cgcgacaaat tacaacggta tatatcctgc cagtactcgg ccgtcgaccg     240
cggtaccccg gaattaagct tgcatgcctg caggcaattg gccgctgtac catgcatgat     300
ctggatttta gtactggatt ttggttttag gaattagaaa ttttattgat agaagtattt     360
tacaaataca aatacatact aagggtttct tatatgctca acacatgagc gaaaccctat     420
aggaaccta attcccttat ctgggaacta ctcacacatt attatggaga aaatagagag     480
agatagattt gtagagagag actggtgatt tcagcgtgtc caagcttgct agcttattta     540
tccacgacat tgatgttgtg ggccttcaac tcttccttaa ccttattgat gacttcggga     600
tcatcgctga tgggtcttgt gtaatccagc aggacagtgg tcttataacc tagttctgca     660
gcggaaatgg cggtggcttt gacacaatac tccaaagcta caccgacaat gtaaacctcg     720
tctgtatgat gcttttctaa gtacttgttc atgtcggtct tatggaagtt ccagatgtcg     780
tggaaggcgg agtagtattc acggtcagtc aagaaaccct tgtcgacaat cttaatatgc     840
ttagtgacca cttggtccat tatttggtca accaattgac tacccaggt gtttttcaca      900
cagtgtacgg gccacaaaat accctcttgc gtggaatcat cgcctggcct tggagagtgg     960
taggtgtatg ttgaataggg ttctttatct ttatggttct ttgcgaacga aatatgtctg    1020
gaagggtgcc aatctctggt gaccacaatc ctgtgccagt ctctatcagc atcttgcatc    1080
aaatccgaga taggattgat taattcctca ccttttggaa cagtcaagga acctaaaggt    1140
gaaataaaat cattttgcat atcaacaacc ttgcgcttct tcttgggaat taagtctcc     1200
atggttttgg tttaataaga agagaaaaga gttcttttgt tatggctgaa gtaatagaga    1260
aatgagctcg agtcctctcc aaatgaaatg aacttcctta tatagaggaa gggtcttgcg    1320
aaggatagtg ggattgtgcg tcatcccta cgtcagtgga gatatcacat caatccactt     1380
gctttgaaga cgtggttgga acgtcttctt ttccacgat gctcctcgtg ggtgggggtc      1440
catctttggg accactgtcg gcagaggcat cttgaacgat agcctttcct ttatcgcaat    1500
gatggcattt gtaggtgcca ccttcctttt ctactgtcct tttgatgaag tgacagatag    1560
ctgggcaatg gaatccgagg aggtttcccg atattaccct ttgttgaaaa gtctcaatag    1620
cccttggtc ttctgagact gtatctttga tattcttgga gtagacgaga gtgtcgtgct      1680
ccaccatgtt gacgaagatt ttcttcttgt cattgagtcg taaaagactc tgtatgaact    1740
gttcgccagt cttcacggcg agttctgtta gatcctcgat ctgaattttt gactccatgt    1800
atggtgcata tggcgcgcca tatgcccggg ccctgtacag cggccgcgtt aacgcgtata    1860
ctctagagcg atcgcccggg ccggccattt aaatgaattc gagctcggta cccaaacgcg    1920
gccgcaagct ataacttcgt atagcataca ttatacgaag ttattcgact ctagaggatc    1980
ccaattccca tgcatggagt caagattcaa atagaggac acttctcgaa ctcggccgtc      2040
gaactcggcc gtcgagtaca tggtcgataa gaaaaggcaa tttgtagatg ttaattccca    2100
tcttgaaaga aatatagttt aaatatttat tgataaaata acaagtcagg tattatagtc    2160
caagcaaaaa cataaattta ttgatgcaag tttaaattca gaaatatttc aataactgat    2220
```

```
tatatcagct ggtacattgc cgtagatgaa agactgagtg cgatattatg tgtaatacat    2280
aaattgatga tatagctagc ttagctcatc gggggatcct agacgcgtga gatcagatct    2340
cggtgacggg caggaccgga cggggcggta ccggcaggct gaagtccagc tgccagaaac    2400
ccacgtcatg ccagttcccg tgcttgaagc cggccgcccg cagcatgccg cgggggggcat   2460 atccgagcgc ctcgtgcatg cgcacgctcg ggtcgttggg cagcccgatg acagcgacca    2520
cgctcttgaa gccctgtgcc tccagggact tcagcaggtg ggtgtagagc gtggagccca    2580
gtcccgtccg ctggtggcgg ggggagacgt cacggtcga ctcggccgtc cagtcgtagg     2640
cgttgcgtgc cttccagggg cccgcgtagg cgatgccggc gacctcgccg tccacctcgg    2700
cgacgagcca gggatagcgc tcccgcagac ggacgaggtc gtccgtccac tcctgcggtt    2760
cctgcggctc ggtacggaag ttgaccgtgc ttgtctcgat gtagtggttg acgatggtgc    2820
agaccgccgg catgtccgcc tcggtggcac ggcggatgtc ggccgggcgt cgttctgggt    2880
ccattgttct tctttactct ttgtgtgact gaggtttggt ctagtgcttt ggtcatctat    2940
atataatgat aacaacaatg agaacaagct ttggagtgat cggagggtct aggatacatg    3000
agattcaagt ggactaggat ctacaccgtt ggattttgag tgtggatatg tgtgaggtta    3060 atttacttg gtaacggcca caaaggccta aggagaggtg ttgagaccct tatcggcttg     3120
aaccgctgga ataatgccac gtggaagata attccatgaa tcttatcgtt atctatgagt    3180
gaaattgtgt gatggtggag tggtgcttgc tcattttact tgcctggtgg acttggccct    3240
ttccttatgg ggaattttata ttttacttac tatagagctt tcataccttt ttttttacctt 3300 ggatttagtt aatatataat ggtatgattc atgaataaaa atgggaaatt tttgaatttg    3360
tactgctaaa tgcataagat taggtgaaac tgtggaatat atatttttt catttaaaag     3420 caaaatttgc cttttactag aattataaat atagaaaat atataacatt caaataaaaa     3480
tgaaaataag aactttcaaa aaacagaact atgtttaatg tgtaaagatt agtcgcacat    3540
caagtcatct gttacaatat gttacaacaa gtcataagcc caacaaagtt agcacgtcta    3600
aataaactaa agagtccacg aaaatattac aaatcataag cccaacaaag ttattgatca    3660
aaaaaaaaaa acgcccaaca aagctaaaca aagtccaaaa aaaacttctc aagtctccat    3720
cttcctttat gaacattgaa aactatacac aaaacaagtc agataaatct ctttctgggc    3780
ctgtcttccc aacctcctac atcacttccc tatcggattg aatgttttac ttgtaccttt    3840
tccgttgcaa tgatattgat agtatgtttg tgaaaactaa tagggttaac aatcgaagtc    3900
atggaatatg gatttggtcc aagattttcc gagagctttc tagtagaaag cccatcacca    3960
gaaatttact agtaaaataa atcaccaatt aggtttctta ttatgtgcca aattcaatat    4020
aattatagag gatatttcaa atgaaaacgt atgaatgtta ttagtaaatg gtcaggtaag    4080
acattaaaaa aatcctacgt cagatattca actttaaaaa ttcgatcagt gtggaattgt    4140
acaaaaattt gggatctact atatatatat aatgcttac aacacttgga ttttttttg      4200 gaggctggaa ttttaatct acatatttgt tttggccatg caccaactca ttgtttagtg     4260
taatactttg attttgtcaa atatatgtgt tcgtgtatat ttgtataaga atttctttga    4320
ccatatacac acacacatat atatatatat atatatatta tatatcatgc acttttaatt   4380
gaaaaaataa tatatatata tatagtgcat ttttctaac aaccatatat gttgcgattg     4440
atctgcaaaa atactgctag agtaatgaaa aatataatct attgctgaaa ttatctcaga    4500
tgttaagatt ttcttaaagt aaattcttc aaatttagc taaagtctt gtaataacta       4560 aagaataata cacaatctcg accacggaaa aaaaacacat aataaatttg aatttcgacc    4620
```

```
gcggtacccg gaattgggtt ataattacct caggtcgagg aattaattcg gtacgtacct    4680
aataacttcg tatagcatac attatacgaa gttatatgga tctcgaggca ttacggcatt    4740
acggcactcg cgagggtccc aattcgagca tggagccatt tacaattgaa tatatcctgc    4800
cgccgctgcc gctttgcacc cggtggagct tgcatgttgg tttctacgca gaactgagcc    4860
ggttaggcag ataatttcca ttgagaactg agccatgtgc accttccccc caacacggtg    4920
agcgacgggg caacggagtg atccacatgg gacttttaaa catcatccgt cggatggcgt    4980
tgcgagagaa gcagtcgatc cgtgagatca gccgacgcac cgggcaggcg cgcaacacga    5040
tcgcaaagta tttgaacgca ggtacaatcg agccgacgtt cacggtaccg gaacgaccaa    5100
gcaagctagc ttagtaaagc cctcgctaga ttttaatgcg gatgttgcga ttacttcgcc    5160
aactattgcg ataacaagaa aaagccagcc tttcatgata tatctcccaa tttgtgtagg    5220
gcttattatg cacgcttaaa aataataaaa gcagacttga cctgatagtt tggctgtgag    5280
caattatgtg cttagtgcat ctaacgcttg agttaagccg cgccgcgaag cggcgtcggc    5340
ttgaacgaat tgttagacat tatttgccga ctaccttggt gatctcgcct ttcacgtagt    5400
ggacaaattc ttccaactga tctgcgcgcg aggccaagcg atcttcttct tgtccaagat    5460
aagcctgtct agcttcaagt atgacgggct gatactgggc cggcaggcgc tccattgccc    5520
agtcggcagc gacatccttc ggcgcgattt tgccggttac tgcgctgtac caaatgcggg    5580
acaacgtaag cactacattt cgctcatcgc cagcccagtc gggcggcgag ttccatagcg    5640
ttaaggtttc atttagcgcc tcaaatagat cctgttcagg aaccggatca agagttcct    5700 ccgccgctgg acctaccaag gcaacgctat gttctcttgc ttttgtcagc aagatagcca    5760
gatcaatgtc gatcgtggct ggctcgaaga tacctgcaag aatgtcattg cgctgccatt    5820
ctccaaattg cagttcgcgc ttagctggat aacgccacgg aatgatgtcg tcgtgcacaa    5880
caatggtgac ttctacagcg cggagaatct cgctctctcc aggggaagcc gaagtttcca    5940
aaaggtcgtt gatcaaagct cgccgcgttg tttcatcaag ccttacggtc accgtaacca    6000
gcaaatcaat atcactgtgt ggcttcaggc cgccatccac tgcggagccg tacaaatgta    6060
cggccagcaa cgtcggttcg agatggcgct cgatgacgcc aactacctct gatagttgag    6120
tcgatacttc ggcgatcacc gcttccctca tgatgtttaa ctttgttta gggcgactgc    6180 cctgctgcgt aacatcgttg ctgctccata acatcaaaca tcgacccacg gcgtaacgcg    6240
cttgctgctt ggatgcccga ggcatagact gtacccaaa aaaacagtca taacaagcca    6300
tgaaaaccgc cactgcgccg ttaccaccgc tgcgttcggt caaggttctg gaccagttgc    6360
gtgagcgcat acgctacttg cattacagct tacgaaccga acaggcttat gtccactggg    6420
ttcgtgcctt catccgtttc cacggtgtgc gtcacccggc aaccttgggc agcagcgaag    6480
tcgaggcatt tctgtcctgg ctggcgaacg agccgcaaggt ttcggtctcc acgcatcgtc    6540
aggcattggc ggccttgctg ttcttctacg gcaagtgctg tgcacggatc tgccctggct    6600
tcaggagatc ggaagacctc ggccgtccgg gcgcttgccg gtggtgctga ccccggatga    6660
agtctctaga gctctagagg gttcgcatcc tcggttttct ggaaggcgag catcgtttgt    6720
tcgcccagct tctgtatgga acgggcatgc ggatcagtga gggtttgcaa ctgcgggtca    6780
aggatctgga tttcgatcac ggcacgatca tcgtgcggga gggcaagggc tccaaggatc    6840
gggccttgat gttacccgag agcttggcac ccagcctgcg cgagcaggga tcgatccaac    6900
ccctccgctg ctatagtgca gtcggcttct gacgttcagt gcagccgtct tctgaaaacg    6960
```

```
acatgtcgca caagtcctaa gttacgcgac aggctgccgc cctgccctt tcctggcgtt    7020 ttcttgtcgc gtgttttagt cgcataaagt agaatacttg cgactagaac cggagacatt    7080
acgccatgaa caagagcgcc gccgctggcc tgctgggcta tgcccgcgtc agcaccgacg    7140
accaggactt gaccaaccaa cgggccgaac tgcacgcggc cggctgcacc aagctgtttt    7200
ccgagaagat caccggcacc aggcgcgacc gccgggagct ggccaggatg cttgaccacc    7260
tacgccctgg cgacgttgtg acagtgacca ggctagaccg cctggcccgc agcacccgcg    7320
acctactgga cattgccgag cgcatccagg aggccggcgc gggcctgcgt agcctggcag    7380
agccgtgggc cgacaccacc acgccggccg ccgcatggt gttgaccgtg ttcgccggca    7440
ttgccgagtt cgagcgttcc ctaatcatcg accgcacccg gagcgggcgc gaggccgcca    7500
aggcccgagg cgtgaagttt ggccccgcc ctaccctcac cccggcacag atcgcgcacg    7560
cccgcgagct gatcgaccag gaaggccgca ccgtgaaaga ggcggctgca ctgcttggcg    7620
tgcatcgctc gaccctgtac cgcgcacttg agcgcagcga ggaagtgacg cccaccgagg    7680
ccaggcggcg cggtgccttc cgtgaggacg cattgaccga ggccgacgcc ctggcggccg    7740
ccgagaatga acgccaagag gaacaagcat gaaaccgcac caggacggcc aggacgaacc    7800 gttttcatt accgaagaga tcgaggcgga gatgatcgcg gccgggtacg tgttcgagcc    7860
gcccgcgcac gtctcaaccg tgcggctgca tgaaatcctg gccggtttgt ctgatgccaa    7920
gctggcggcc tggccggcca gcttggccgc tgaagaaacc gagcgccgcc gtctaaaaag    7980
gtgatgtgta tttgagtaaa acagcttgcg tcatgcggtc gctgcgtata tgatgcgatg    8040
agtaaataaa caaatacgca aggggaacgc atgaaggtta tcgctgtact taaccagaaa    8100
ggcgggtcag gcaagacgac catcgcaacc catctagccc gcgccctgca actcgccggg    8160
gccgatgttc tgttagtcga ttccgatccc cagggcagtg cccgcgattg gcggccgtg    8220 cgggaagatc aaccgctaac cgttgtcggc atcgaccgcc cgacgattga ccgcgacgtg    8280
aaggccatcg gccggcgcga cttcgtagtg atcgacggag cgccccaggc ggcggacttg    8340
gctgtgtccg cgatcaaggc agccgacttc gtgctgattc cggtgcagcc aagcccttac    8400
gacatatggg ccaccgccga cctggtggag ctggttaagc agcgcattga ggtcacggat    8460
ggaaggctac aagcggcctt tgtcgtgtcg cgggcgatca aaggcacgcg catcggcggt    8520
gaggttgccg aggcgctggc cgggtacgag ctgcccattc ttgagtcccg tatcacgcag    8580
cgcgtgagct acccaggcac tgccgccgcc ggcacaaccg ttcttgaatc agaacccgag    8640
ggcgacgctg cccgcgaggt ccaggcgctg gccgctgaaa ttaaatcaaa actcatttga    8700
gttaatgagg taaagagaaa atgagcaaaa gcacaaacac gctaagtgcc ggccgtccga    8760
gcgcacgcag cagcaaggct gcaacgttgg ccagcctggc agacacgcca gccatgaagc    8820
gggtcaactt tcagttgccg gcggaggatc acaccaagct gaagatgtac gcggtacgcc    8880
aaggcaagac cattaccgag ctgctatctg aatacatcgc gcagctacca gagtaaatga    8940
gcaaatgaat aaatgagtag atgaatttta gcggctaaag gaggcggcat ggaaaatcaa    9000
gaacaaccag gcaccgacgc cgtggaatgc cccatgtgtg gaggaacggg cggttggcca    9060
ggcgtaagcg gctgggttgt ctgccggccc tgcaatggca ctggaacccc caagcccgag    9120
gaatcggcgt gacggtcgca aaccatccgg cccggtacaa atcggcgcgg cgctgggtga    9180
tgacctggtg gagaagttga aggccgcgca ggccgcccag cggcaacgca tcgaggcaga    9240
agcacgcccc ggtgaatcgt ggcaagcggc cgctgatcga atccgcaaag aatcccggca    9300
accgccggca gccggtgcgc cgtcgattag gaagccgccc aagggcgacg agcaaccaga    9360
```

```
tttttttcgtt ccgatgctct atgacgtggg cacccgcgat agtcgcagca tcatggacgt   9420
ggccgttttc cgtctgtcga agcgtgaccg acgagctggc gaggtgatcc gctacgagct   9480
tccagacggg cacgtagagg tttccgcagg gccggccggc atggccagtg tgtgggatta   9540
cgacctggta ctgatggcgg tttcccatct aaccgaatcc atgaaccgat accgggaagg   9600
gaagggagac aagcccggcc gcgtgttccg tccacacgtt gcggacgtac tcaagttctg   9660
ccggcgagcc gatggcggaa agcagaaaga cgacctggta gaaacctgca ttcggttaaa   9720
caccacgcac gttgccatgc agcgtacgaa gaaggccaag aacggccgcc tggtgacggt   9780
atccgagggt gaagccttga ttagccgcta caagatcgta aagagcgaaa ccgggcggcc   9840
ggagtacatc gagatcgagc tagctgattg gatgtaccgc gagatcacag aaggcaagaa   9900
cccggacgtg ctgacggttc accccgatta cttttttgatc gatcccggca tcggccgttt   9960
tctctaccgc ctggcacgcc gcgccgcagg caaggcagaa gccagatggt tgttcaagac  10020
gatctacgaa cgcagtggca gcgccggaga gttcaagaag ttctgtttca ccgtgcgcaa  10080
gctgatcggg tcaaatgacc tgccggagta cgatttgaag gaggaggcgg ggcaggctgg  10140
cccgatccta gtcatgcgct accgcaacct gatcgagggc gaagcatccg ccggttccta  10200
atgtacggag cagatgctag ggcaaattgc cctagcaggg gaaaaaggtc gaaaaggtct  10260
ctttcctgtg gatagcacgt acattgggaa cccaaagccg tacattggga accggaaccc  10320
gtacattggg aacccaaagc cgtacattgg gaaccggtca cacatgtaag tgactgatat  10380
aaaagagaaa aaaggcgatt tttccgccta aaactcttta aaacttatta aaactcttaa  10440
aacccgcctg gcctgtgcat aactgtctgg ccagcgcaca gccgaagagc tgcaaaaagc  10500
gcctacccctt cggtcgctgc gctccctacg ccccgccgct tcgcgtcggc ctatcgcggc  10560
cgctggccgc tcaaaaatgg ctggcctacg gccaggcaat ctaccagggc gcggacaagc  10620
cgcgccgtcg ccactcgacc gccggcgccc acatcaaggc accctgcctc gcgcgtttcg  10680
gtgatgacgg tgaaaacctc tgacacatgc agctcccgga gacggtcaca gcttgtctgt  10740
aagcggatgc cggggagcaga caagcccgtc agggcgcgtc agcgggtgtt ggcgggtgtc  10800
ggggcgcagc catgacccag tcacgtagcg atagcggagt gtatactggc ttaactatgc  10860
ggcatcagag cagattgtac tgagagtgca ccatatgcgg tgtgaaatac cgcacagatg  10920
cgtaaggaga aaataccgca tcaggcgctc ttccgcttcc tcgctcactg actcgctgcg  10980
ctcggtcgtt cggctgcggc gagcggtatc agctcactca aaggcggtaa tacggttatc  11040
cacagaatca ggggataacg caggaaagaa catgtgagca aaaggccagc aaaaggccag  11100
gaaccgtaaa aaggccgcgt tgctggcgtt tttccatagg ctccgccccc ctgacgagca  11160
tcacaaaaat cgacgctcaa gtcagaggtg gcgaaacccg acaggactat aaagatacca  11220
ggcgttttcc cctggaagct ccctcgtgcg ctctcctgtt ccgaccctgc cgcttaccgg  11280
atacctgtcc gcctttctcc cttcgggaag cgtggcgctt tctcatagct cacgctgtag  11340
gtatctcagt tcggtgtagg tcgttcgctc caagctgggc tgtgtgcacg aaccccccgt  11400
tcagcccgac cgctgcgcct tatccggtaa ctatcgtctt gagtccaacc cggtaagaca  11460
cgacttatcg ccactggcag cagccactgg taacaggatt agcagagcga ggtatgtagg  11520
cggtgctaca gagttcttga agtggtggcc taactacggc tacactagaa ggacagtatt  11580
tggtatctgc gctctgctga agccagttac cttcggaaaa agagttggta gctcttgatc  11640
cggcaaacaa accaccgctg gtagcggtgg tttttttgtt tgcaagcagc agattacgcg  11700
```

-continued

```
cagaaaaaaa ggatctcaag aagatccgga aaacgcaagc gcaaagagaa agcaggtagc   11760
ttgcagtggg cttacatggc gatagctaga ctgggcggtt tatggacag caagcgaacc    11820
ggaattgcc                                                          11829

<210> SEQ ID NO 27
<211> LENGTH: 12393
<212> TYPE: DNA
<213> ORGANISM: Artificial
<220> FEATURE:
<223> OTHER INFORMATION: pTVE469

<400> SEQUENCE: 27
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggattta gtactggatt ttggttttag gaattagaaa ttttattgat agaagtattt     360
tacaaataca aatacatact aagggtttct tatatgctca acacatgagc gaaaccctat    420
aggaaccta attcccttat ctgggaacta ctcacacatt attatggaga aaatagagag     480
agatagattt gtagagagag actggtgatt tcagcgtgtc caagcttgct agcttatgct    540
atagggaggc ataattgatg cttggcttga ataacagcat cacgatcacc agtatttttc    600
atgatatcgt cactaatctt cactgcttta gttccttcag cggaaaaaag cttaataaca    660
atattcatag gtttgctcac ttcactggga ttggaaactt tttggaagtc gctggtaaga    720
tttgtgccga tgccaaatgc agacttaatg ccacatttct cgcagtattt gtacagttcg    780
atacatctgt caacatttaa agcatcgcta tgaacaatta cttttgtgga aggatcgaca    840
cctattgatt tatagtgctt tacgactttt tcaatgtatt cctcagcaca accgctatct    900
tgacgaacac catggaaaac attggctaaa tcgtcggcag aattggctgt aaaagatttg    960
agaaacacat cagtagagaa tgtatccgtt aaggctatta aaagactagt accaaaagtt   1020
tggacccact ttaaggaagc aatacgattt gcttgtttat aattttgagt aatagctgca   1080
atgcccatat accactcgtg agcaaccgta ccagagacat ttagattata tttggcggcg   1140
aagtaaacat tagatgtacc aaggaaactt ccagggccct aaaatcctc ttgtgctttc    1200
atgagacctt ggagaacaat ttcctgggtg tgaggatcac gacgacgacg agtgccaaag   1260
tcagtaaagg cacatccggc tcggatgaga cgcttaccct tctcgtaagc ttttcaaac    1320
tgaccctcag gtgaccagtc cttatcgaca aatttaaaat aagattctga gacgagagca   1380
agcagtggaa tttcataaaa aatggtattc ttccagaggc cgtgaataaa gattgagaga   1440
tccttagttt cagaatcata attaagggaa attgaatttt caggatcaaa ttcgaactca   1500
tgcatgaatt cataaaatga ttcctttaaa taaggacagt tcttgcgaag ccattgctct   1560
tcttcaggaa gtaaatgtaa attccgtaag cctcttattt gttcccgtaa ccagttataa   1620
gcctcctgat ttaatgccat ttttgggac cggtttgtat acttatatga tacttgagca    1680
tccggataat gctctaaaac ggcttgaagc atggtgagtt tgtaaagatc cgtatcgagg   1740
atagagacaa cagccggttc acccatggtt ttggtttaat aagaagagaa aagagttctt   1800
ttgttatggc tgaagtaata gagaaatgag ctcgagtcct ctccaaatga atgaacttc    1860
cttatataga ggaagggtct tgcgaaggat agtgggattg tgcgtcatcc cttacgtcag   1920
```

```
tggagatatc acatcaatcc acttgctttg aagacgtggt tggaacgtct tcttttccca    1980
cgatgctcct cgtgggtggg ggtccatctt tgggaccact gtcggcagag gcatcttgaa    2040
cgatagcctt tcctttatcg caatgatggc atttgtaggt gccaccttcc ttttctactg    2100
tcctttgat gaagtgacag atagctgggc aatggaatcc gaggaggttt cccgatatta     2160
ccctttgttg aaaagtctca atagccctt ggtcttctga gactgtatct ttgatattct     2220
tggagtagac gagagtgtcg tgctccacca tgttgacgaa gattttcttc ttgtcattga    2280
gtcgtaaaag actctgtatg aactgttcgc cagtcttcac ggcgagttct gttagatcct    2340
cgatctgaat ttttgactcc atgtatggtg catatggcgc gccatatgcc cgggccctgt    2400
acagcggccg cgttaacgcg tatactctag agcgatcgcc cgggccggcc atttaaatga    2460
attcgagctc ggtacccaaa cgcggccgca agctataact tcgtatagca tacattatac    2520
gaagttattc gactctagag gatcccaatt cccatgcatg gagtcaaaga ttcaaataga    2580
ggacacttct cgaactcggc cgtcgaactc ggccgtcgag tacatggtcg ataagaaaag    2640
gcaatttgta gatgttaatt cccatcttga aagaaatata gtttaaatat ttattgataa    2700
aataacaagt caggtattat agtccaagca aaaacataaa tttattgatg caagtttaaa    2760
ttcagaaata tttcaataac tgattatatc agctggtaca ttgccgtaga tgaaagactg    2820
agtgcgatat tatgtgtaat acataaattg atgatatagc tagcttagct catcggggga    2880
tcctagacgc gtgagatcag atctcggtga cgggcaggac cggacggggc ggtaccggca    2940
ggctgaagtc cagctgccag aaacccacgt catgccagtt cccgtgcttg aagccggccg    3000
cccgcagcat gccgcggggg gcatatccga gcgcctcgtg catgcgcacg ctcgggtcgt    3060
tgggcagccc gatgacagcg accacgctct gaagccctg tgcctccagg acttcagca     3120
ggtgggtgta gagcgtggag cccagtcccg tccgctggtg gcgggggag acgtacacgg     3180
tcgactcggc cgtccagtcg taggcgttgc gtgccttcca ggggcccgcg taggcgatgc    3240
cggcgacctc gccgtccacc tcggcgacga gccagggata gcgctcccgc agacggacga    3300
ggtcgtccgt ccactcctgc ggttcctgcg gctcggtacg gaagttgacc gtgcttgtct    3360
cgatgtagtg gttgacgatg gtgcagaccg ccggcatgtc cgcctcggtg gcacggcgga    3420
tgtcggccgg gcgtcgttct gggtccattg ttcttcttta ctctttgtgt gactgaggtt    3480
tggtctagtg ctttggtcat ctatatataa tgataacaac aatgagaaca gctttggag    3540
tgatcggagg gtctaggata catgagattc aagtggacta ggatctacac cgttggattt    3600
tgagtgtgga tatgtgtgag gttaatttta cttggtaacg gccacaaagg cctaaggaga    3660
ggtgttgaga cccttatcgg cttgaaccgc tggaataatg ccacgtggaa gataattcca    3720
tgaatcttat cgttatctat gagtgaaatt gtgtgatggt ggagtggtgc ttgctcattt    3780
tacttgcctg gtggacttgg cccttttcctt atggggaatt tatattttac ttactataga    3840
gctttcatac ctttttttta ccttggattt agttaatata taatggtatg attcatgaat    3900
aaaaatggga aattttgaa tttgtactgc taaatgcata agattaggtg aaactgtgga    3960
atatatattt ttttcattta aaagcaaaat ttgccttta ctagaattat aaatatagaa     4020
aaatatataa cattcaaata aaatgaaaa taagaacttt caaaaaacag aactatgttt     4080
aatgtgtaaa gattagtcgc acatcaagtc atctgttaca atatgttaca acaagtcata    4140
agcccaacaa agttagcacg tctaaataaa ctaaagagtc cacgaaaata ttacaaatca    4200
taagcccaac aaagttattg atcaaaaaaa aaaaacgccc aacaaagcta acaaagtcc    4260
```

```
aaaaaaaact tctcaagtct ccatcttcct ttatgaacat tgaaaactat acacaaaaca    4320
agtcagataa atctctttct gggcctgtct tcccaacctc ctacatcact tccctatcgg    4380
attgaatgtt ttacttgtac cttttccgtt gcaatgatat tgatagtatg tttgtgaaaa    4440
ctaatagggt taacaatcga agtcatggaa tatggatttg gtccaagatt ttccgagagc    4500
tttctagtag aaagcccatc accagaaatt tactagtaaa ataaatcacc aattaggttt    4560
cttattatgt gccaaattca atataattat agaggatatt tcaaatgaaa acgtatgaat    4620
gttattagta aatggtcagg taagacatta aaaaaatcct acgtcagata ttcaacttta    4680
aaaattcgat cagtgtggaa ttgtacaaaa atttgggatc tactatatat ataatgct     4740 ttacaacact tggattttt tttggaggct ggaattttta atctacatat ttgttttggc     4800
catgcaccaa ctcattgttt agtgtaatac tttgattttg tcaaatatat gtgttcgtgt    4860
atatttgtat aagaatttct ttgaccatat acacacacac atatatatat atatatatat    4920
attatatatc atgcactttt aattgaaaaa ataatatata tatatatagt gcattttttc    4980
taacaaccat atatgttgcg attgatctgc aaaaatactg ctagagtaat gaaaaatata    5040
atctattgct gaaattatct cagatgttaa gattttctta agtaaattc tttcaaattt     5100 tagctaaaag tcttgtaata actaaagaat aatacacaat ctcgaccacg gaaaaaaaac    5160
acataataaa tttgaatttc gaccgcggta cccggaattg ggttataatt acctcaggtc    5220
gaggaattaa ttcggtacgt acctaataac ttcgtatagc atacattata cgaagttata    5280
tggatctcga ggcattacgg cattacggca ctcgcgaggg tcccaattcg agcatggagc    5340
catttacaat tgaatatatc ctgccgccgc tgccgctttg cacccggtgg agcttgcatg    5400
ttggtttcta cgcagaactg agccggttag gcagataatt tccattgaga actgagccat    5460
gtgcaccttc cccccaacac ggtgagcgac ggggcaacgg agtgatccac atgggacttt    5520
taaacatcat ccgtcggatg gcgttgcgag agaagcagtc gatccgtgag atcagccgac    5580
gcaccgggca ggcgcgcaac acgatcgcaa agtatttgaa cgcaggtaca atcgagccga    5640
cgttcacggt accggaacga ccaagcaagc tagcttagta aagccctcgc tagattttaa    5700
tgcggatgtt gcgattactt cgccaactat tgcgataaca agaaaaagcc agcctttcat    5760
gatatatctc ccaatttgtg tagggcttat tatgcacgct taaaaataat aaaagcagac    5820
ttgacctgat agtttggctg tgagcaatta tgtgcttagt gcatctaacg cttgagttaa    5880
gccgcgccgc gaagcggcgt cggcttgaac gaattgttag acattatttg ccgactacct    5940
tggtgatctc gccttttcacg tagtggacaa attcttccaa ctgatctgcg cgcgaggcca    6000
agcgatcttc ttcttgtcca agataagcct gtctagcttc aagtatgacg ggctgatact    6060
gggccggcag gcgctccatt gcccagtcgg cagcgacatc cttcggcgcg attttgccgg    6120
ttactgcgct gtaccaaatg cgggacaacg taagcactac atttcgctca tcgccagccc    6180
agtcgggcgg cgagttccat agcgttaagg tttcatttag cgcctcaaat agatcctgtt    6240
caggaaccgg atcaaagagt tcctccgccg ctggacctac caaggcaacg ctatgttctc    6300
ttgcttttgt cagcaagata gccagatcaa tgtcgatcgt ggctggctcg aagatacctg    6360
caagaatgtc attgcgctgc cattctccaa attgcagttc gcgcttagct ggataacgcc    6420
acggaatgat gtcgtcgtgc acaacaatgg tgacttctac agcgcggaga atctcgctct    6480
ctccagggga agccgaagtt ccaaaaggt cgttgatcaa agctcgccgc gttgtttcat     6540
caagccttac ggtcaccgta accagcaaat caatatcact gtgtggcttc aggccgccat    6600
ccactgcgga gccgtacaaa tgtacggcca gcaacgtcgg ttcgagatgg cgctcgatga    6660
```

```
cgccaactac ctctgatagt tgagtcgata cttcggcgat caccgcttcc ctcatgatgt   6720
ttaactttgt tttagggcga ctgccctgct gcgtaacatc gttgctgctc cataacatca   6780
aacatcgacc cacggcgtaa cgcgcttgct gcttggatgc ccgaggcata gactgtaccc   6840
caaaaaaaca gtcataacaa gccatgaaaa ccgccactgc gccgttacca ccgctgcgtt   6900
cggtcaaggt tctggaccag ttgcgtgagc gcatacgcta cttgcattac agcttacgaa   6960
ccgaacaggc ttatgtccac tgggttcgtg ccttcatccg tttccacggt gtgcgtcacc   7020
cggcaacctt gggcagcagc gaagtcgagg catttctgtc ctggctggcg aacgagcgca   7080
aggtttcggt ctccacgcat cgtcaggcat ggcggcctt gctgttcttc tacggcaagt   7140
gctgtgcacg gatctgccct ggcttcagga gatcggaaga cctcggccgt ccgggcgctt   7200
gccggtggtg ctgaccccgg atgaagtctc tagagctcta gagggttcgc atcctcggtt   7260
ttctggaagg cgagcatcgt ttgttcgccc agcttctgta tggaacgggc atgcggatca   7320
gtgagggttt gcaactgcgg gtcaaggatc tggatttcga tcacggcacg atcatcgtgc   7380
gggagggcaa gggctccaag gatcgggcct tgatgttacc cgagagcttg cacccagcc   7440
tgcgcgagca gggatcgatc caacccctcc gctgctatag tgcagtcggc ttctgacgtt   7500
cagtgcagcc gtcttctgaa aacgacatgt cgcacaagtc ctaagttacg cgacaggctg   7560
ccgccctgcc cttttcctgg cgttttcttg tcgcgtgttt tagtcgcata agtagaata   7620
cttgcgacta gaaccggaga cattacgcca tgaacaagag cgccgccgct ggcctgctgg   7680
gctatgcccg cgtcagcacc gacgaccagg acttgaccaa ccaacgggcc gaactgcacg   7740
cggccggctg caccaagctg ttttccgaga agatcaccgg caccaggcgc gaccgcccgg   7800
agctggccag gatgcttgac cacctacgcc ctggcgacgt tgtgacagtg accaggctag   7860
accgcctggc ccgcagcacc cgcgacctac tggacattgc cgagcgcatc caggaggccg   7920
gcgcgggcct gcgtagcctg gcagagccgt gggccgacac caccacgccg gccggccgca   7980
tggtgttgac cgtgttcgcc ggcattgccg agttcgagcg ttccctaatc atcgaccgca   8040
cccggagcgg gcgcgaggcc gccaaggccc gaggcgtgaa gtttggcccc cgccctaccc   8100
tcaccccggc acagatcgcg cacgcccgcg agctgatcga ccaggaaggc cgcaccgtga   8160
aagaggcggc tgcactgctt ggcgtgcatc gctcgaccct gtaccgcgca cttgagcgca   8220
gcgaggaagt gacgcccacc gaggccaggc ggcgcggtgc cttccgtgag gacgcattga   8280
ccgaggccga cgccctggcg gccgccgaga atgaacgcca agaggaacaa gcatgaaacc   8340
gcaccaggac ggccaggacg aaccgttttt cattaccgaa gagatcgagg cggagatgat   8400
cgcggccggg tacgtgttcg agccgccccg cacgtctca accgtgcggc tgcatgaaat   8460
cctggccggt ttgtctgatg ccaagctggc ggcctggccg gccagcttgg ccgctgaaga   8520
aaccgagcgc cgccgtctaa aaggtgatg tgtatttgag taaacagct tgcgtcatgc   8580
ggtcgctgcg tatatgatgc gatgagtaaa taaacaaata cgcaaggga acgcatgaag   8640
gttatcgctg tacttaacca gaaaggcggg tcaggcaaga cgaccatcgc aacccatcta   8700
gcccgcgccc tgcaactcgc cggggccgat gttctgttag tcgattccga tcccagggc   8760
agtgcccgcg attgggcggc cgtgcggaa gatcaaccgc taaccgttgt cggcatcgac   8820
cgcccgacga ttgaccgcga cgtgaaggcc atcggccggc gcgacttcgt agtgatcgac   8880
ggagcgcccc aggcggcgga cttgctgtg tccgcgatca aggcagccga cttcgtgctg   8940
attccggtgc agccaagccc ttacgacata tgggccaccg ccgacctggt ggagctggtt   9000
```

```
aagcagcgca ttgaggtcac ggatggaagg ctacaagcgg cctttgtcgt gtcgcgggcg    9060
atcaaaggca cgcgcatcgg cggtgaggtt gccgaggcgc tggccgggta cgagctgccc    9120
attcttgagt cccgtatcac gcagcgcgtg agctacccag gcactgccgc cgccggcaca    9180
accgttcttg aatcagaacc cgagggcgac gctgcccgcg aggtccaggc gctggccgct    9240
gaaattaaat caaaactcat ttgagttaat gaggtaaaga gaaaatgagc aaaagcacaa    9300
acacgctaag tgccggccgt ccgagcgcac gcagcagcaa ggctgcaacg ttggccagcc    9360
tggcagacac gccagccatg aagcgggtca actttcagtt gccggcggag gatcacacca    9420
agctgaagat gtacgcggta cgccaaggca agaccattac cgagctgcta tctgaataca    9480
tcgcgcagct accagagtaa atgagcaaat gaataaatga gtagatgaat tttagcggct    9540
aaaggaggcg gcatggaaaa tcaagaacaa ccaggcaccg acgccgtgga atgcccatg     9600 tgtggaggaa cgggcggttg gccaggcgta agcggctggg ttgtctgccg gccctgcaat    9660
ggcactggaa cccccaagcc cgaggaatcg gcgtgacggt cgcaaaccat ccggcccggt    9720
acaaatcggc gcggcgctgg gtgatgacct ggtggagaag ttgaaggccg cgcaggccgc    9780
ccagcggcaa cgcatcgagg cagaagcacg ccccggtgaa tcgtggcaag cggccgctga    9840
tcgaatccgc aaagaatccc ggcaaccgcc ggcagccggt gcgccgtcga ttaggaagcc    9900
gcccaagggc gacgagcaac cagatttttt cgttccgatg ctctatgacg tgggcacccg    9960
cgatagtcgc agcatcatgg acgtggccgt tttccgtctg tcgaagcgtg accgacgagc    10020
tggcgaggtg atccgctacg agcttccaga cgggcacgta gaggtttccg cagggccggc    10080
cggcatggcc agtgtgtggg attacgacct ggtactgatg gcggtttccc atctaaccga    10140
atccatgaac cgataccggg aagggaaggg agacaagccc ggccgcgtgt tccgtccaca    10200
cgttgcggac gtactcaagt tctgccggcg agccgatggc ggaaagcaga aagacgacct    10260
ggtagaaacc tgcattcggt taaacaccac gcacgttgcc atgcagcgta cgaagaaggc    10320
caagaacggc cgcctggtga cggtatccga gggtgaagcc ttgattagcc gctacaagat    10380
cgtaaagagc gaaaccgggc ggccggagta catcgagatc gagctagctg attggatgta    10440
ccgcgagatc acagaaggca agaacccgga cgtgctgacg gttcaccccg attactttt     10500 gatcgatccc ggcatcggcc gttttctcta ccgcctggca cgccgcgccg caggcaaggc    10560
agaagccaga tggttgttca agacgatcta cgaacgcagt ggcagcgccg gagagttcaa    10620
gaagttctgt ttcaccgtgc gcaagctgat cgggtcaaat gacctgccgg agtacgattt    10680
gaaggaggag gcggggcagg ctggcccgat cctagtcatg cgctaccgca acctgatcga    10740
gggcgaagca tccgccggtt cctaatgtac ggagcagatg ctagggcaaa ttgccctagc    10800
aggggaaaaa ggtcgaaaag gtctctttcc tgtggatagc acgtacattg ggaacccaaa    10860
gccgtacatt gggaaccgga acccgtacat tgggaaccca agccgtaca ttgggaaccg     10920 gtcacacatg taagtgactg atataaaaga gaaaaaggc gatttttccg cctaaaactc      10980
tttaaaactt attaaaactc ttaaaacccg cctggcctgt gcataactgt ctggccagcg    11040
cacagccgaa gagctgcaaa aagcgcctac ccttcggtcg ctgcgctccc tacgccccgc    11100
cgcttcgcgt cggcctatcg cggccgctgg ccgctcaaaa atggctggcc tacggccagg    11160
caatctacca gggcgcggac aagccgcgcc gtcgccactc gaccgccggc gcccacatca    11220
aggcaccctg cctcgcgcgt ttcggtgatg acggtgaaaa cctctgacac atgcagctcc    11280
cggagacggt cacagcttgt ctgtaagcgg atgccgggag cagacaagcc cgtcagggcg    11340
cgtcagcggg tgttggcggg tgtcggggcg cagccatgac ccagtcacgt agcgatagcg    11400
```

```
gagtgtatac tggcttaact atgcggcatc agagcagatt gtactgagag tgcaccatat    11460
gcggtgtgaa ataccgcaca gatgcgtaag gagaaaatac cgcatcaggc gctcttccgc    11520
ttcctcgctc actgactcgc tgcgctcggt cgttcggctg cggcgagcgg tatcagctca    11580
ctcaaaggcg gtaatacggt tatccacaga atcaggggat aacgcaggaa agaacatgtg    11640
agcaaaaggc cagcaaaagg ccaggaaccg taaaaaggcc gcgttgctgg cgttttttcca   11700 taggctccgc cccctgacg agcatcacaa aaatcgacgc tcaagtcaga ggtggcgaaa     11760
cccgacagga ctataaagat accaggcgtt tcccctgga agctccctcg tgcgctctcc     11820
tgttccgacc ctgccgctta ccggatacct gtccgccttt ctcccttcgg aagcgtggc     11880 gctttctcat agctcacgct gtaggtatct cagttcggtg taggtcgttc gctccaagct    11940
gggctgtgtg cacgaacccc ccgttcagcc cgaccgctgc gccttatccg gtaactatcg    12000
tcttgagtcc aacccggtaa gacacgactt atcgccactg gcagcagcca ctggtaacag    12060
gattagcaga gcgaggtatg taggcggtgc tacagagttc ttgaagtggt ggcctaacta    12120
cggctacact agaaggacag tatttggtat ctgcgctctg ctgaagccag ttaccttcgg    12180
aaaaagagtt ggtagctctt gatccggcaa acaaaccacc gctggtagcg gtggttttttt   12240 tgtttgcaag cagcagatta cgcgcagaaa aaaaggatct caagaagatc cggaaaacgc    12300
aagcgcaaag agaaagcagg tagcttgcag tgggcttaca tggcgatagc tagactgggc    12360
ggttttatgg acagcaagcg aaccggaatt gcc                                12393

<210> SEQ ID NO 28
<211> LENGTH: 12414
<212> TYPE: DNA
<213> ORGANISM: Artificial
<220> FEATURE:
<223> OTHER INFORMATION: pTVE 470

<400> SEQUENCE: 28
agattcgaag ctcggtcccg tgggtgttct gtcgtctcgt tgtacaacga atccattcc       60 cattccgcgc tcaagatggc ttcccctcgg cagttcatca gggctaaatc aatctagccg     120
acttgtccgg tgaaatgggc tgcactccaa cagaaacaat caaacaaaca tacacagcga     180
cttattcaca cgcgacaaat tacaacggta tatatcctgc cagtactcgg ccgtcgaccg     240
cggtaccccg gaattaagct tgcatgcctg caggcaattg gccgctgtac catgcatgat     300
ctggatttta gtactggatt ttggttttag gaattagaaa ttttattgat agaagtattt     360
tacaaataca aatacatact aagggttttct tatatgctca acacatgagc gaaaccctat    420 aggaaccctca attcccttat ctgggaacta ctcacacatt attatggaga aaatagagag    480
agatagattt gtagagagag actggtgatt tcagcgtgtc caagcttgct agcttatgct    540
atagggaggc ataattgatg cttggcttga ataacagcat cacgatcacc agtatttttc     600
atgatatcgt cactaatctt cactgcttta gttccttcag cggaaaaaag cttaataaca     660
atattcatag gtttgctcac ttcactggga ttggaaactt tttggaagtc gctggtaaga    720
tttgtgccga tgccaaatgc agacttaatg ccacatttct cgcagtattt gtacagttcg    780
atacatctgt caacatttaa agcatcgcta tgaacaatta cttttgtgga aggatcgaca    840
cctattgatt tatagtgctt tacgactttt tcaatgtatt cctcagcaca accgctatct    900
tgacgaacac catggaaaac attggctaaa tcgtcggcag aattggctgt aaagatttg    960 agaaacacat cagtagagaa tgtatccgtt aaggctatta aagactagt accaaaagtt   1020
```

```
tggacccact ttaaggaagc aatacgattt gcttgtttat aattttgagt aatagctgca    1080
atgcccatat accactcgtg agcaaccgta ccagagacat ttagattata tttggcggcg    1140
aagtaaacat tagatgtacc aaggaaactt ccagggccct taaaatcctc ttgtgctttc    1200
atgagacctt ggagaacaat tcctgggtg tgaggatcac gacgacgacg agtgccaaag    1260
tcagtaaagg cacatccggc tcggatgaga cgcttaccct tctcgtaagc tttttcaaac    1320
tgaccctcag gtgaccagtc cttatcgaca aatttaaaat aagattctga gacgagagca    1380
agcagtggaa tttcataaaa aatggtattc ttccagaggc cgtgaataaa gattgagaga    1440
tccttagttt cagaatcata attaagggaa attgaatttt caggatcaaa ttcgaactca    1500
tgcatgaatt cataaaatga ttcctttaaa taaggacagt tcttgcgaag ccattgctct    1560
tcttcaggaa gtaaatgtaa attccgtaag cctcttattt gttcccgtaa ccagttataa    1620
gcctcctgat ttaatgccat ttttggggac cggtttgtat acttatatga tacttgagca    1680
tccggataat gctctaaaac ggcttgaagc atggtgagtt tgtaaagatc cgtatcgagg    1740
atagagacaa cagcaaccct gcgcttcttc ttgggcggtt cacccatggt tttggtttaa    1800
taagaagaga aaagagttct tttgttatgg ctgaagtaat agagaaatga gctcgagtcc    1860
tctccaaatg aaatgaactt ccttatatag aggaagggtc ttgcgaagga tagtgggatt    1920
gtgcgtcatc ccttacgtca gtggagatat cacatcaatc cacttgcttt gaagacgtgg    1980
ttggaacgtc ttcttttcc acgatgctcc tcgtgggtgg gggtccatct ttgggaccac    2040
tgtcggcaga ggcatcttga acgatagcct ttcctttatc gcaatgatgg catttgtagg    2100
tgccaccttc cttttctact gtccttttga tgaagtgaca gatagctggg caatggaatc    2160
cgaggaggtt tccgatatt acctttgtt gaaaagtctc aatagccctt tggtcttctg    2220
agactgtatc tttgatattc ttggagtaga cgagagtgtc gtgctccacc atgttgacga    2280
agattttctt cttgtcattg agtcgtaaaa gactctgtat gaactgttcg ccagtcttca    2340
cggcgagttc tgttagatcc tcgatctgaa ttttgactc catgtatggt gcatatggcg    2400
cgccatatgc ccgggccctg tacagcggcc gcgttaacgc gtatactcta gagcgatcgc    2460
ccgggccggc catttaaatg aattcgagct cggtacccaa acgcggccgc aagctataac    2520
ttcgtatagc atacattata cgaagttatt cgactctaga ggatcccaat tcccatgcat    2580
ggagtcaaag attcaaatag aggacacttc tcgaactcgg ccgtcgaact cggccgtcga    2640
gtacatggtc gataagaaaa ggcaatttgt agatgttaat tcccatcttg aaagaaatat    2700
agtttaaata tttattgata aaataacaag tcaggtatta tagtccaagc aaaaacataa    2760
atttattgat gcaagtttaa attcagaaat atttcaataa ctgattatat cagctggtac    2820
attgccgtag atgaaagact gagtgcgata ttatgtgtaa tacataaatt gatgatatag    2880
ctagcttagc tcatcggggg atcctagacg cgtgagatca gatctcggtg acgggcagga    2940
ccggacgggg cggtaccggc aggctgaagt ccagctgcca gaaacccacg tcatgccagt    3000
tcccgtgctt gaagccggcc gcccgcagca tgccgcgggg gcatatccg agcgcctcgt    3060 gcatgcgcac gctcgggtcg ttgggcagcc cgatgacagc gaccacgctc ttgaagccct    3120
gtgcctccag ggacttcagc aggtgggtgt agagcgtgga gcccagtccc gtccgctggt    3180
ggcgggggga gacgtacacg gtcgactcgg ccgtccagtc gtaggcgttg cgtgccttcc    3240
aggggcccgc gtaggcgatg ccggcgacct cgccgtccac ctcggcgacg agccagggat    3300
agcgctcccg cagacggacg aggtcgtccg tccactcctg cggttcctgc ggctcggtac    3360
ggaagttgac cgtgcttgtc tcgatgtagt ggttgacgat ggtgcagacc gccggcatgt    3420
```

```
ccgcctcggt ggcacggcgg atgtcggccg ggcgtcgttc tgggtccatt gttcttcttt    3480
actctttgtg tgactgaggt ttggtctagt gctttggtca tctatatata atgataacaa    3540
caatgagaac aagctttgga gtgatcggag ggtctaggat acatgagatt caagtggact    3600
aggatctaca ccgttggatt ttgagtgtgg atatgtgtga ggttaatttt acttggtaac    3660
ggccacaaag gcctaaggag aggtgttgag acccttatcg gcttgaaccg ctggaataat    3720
gccacgtgga agataattcc atgaatctta tcgttatcta tgagtgaaat tgtgtgatgg    3780
tggagtggtg cttgctcatt ttacttgcct ggtggacttg gccctttcct tatggggaat    3840
ttatatttta cttactatag agctttcata cctttttttt accttggatt tagttaatat    3900
ataatggtat gattcatgaa taaaaatggg aaatttttga atttgtactg ctaaatgcat    3960
aagattaggt gaaactgtgg aatatatatt tttttcattt aaaagcaaaa tttgcctttt    4020
actagaatta taaatataga aaaatatata acattcaaat aaaaatgaaa ataagaactt    4080
tcaaaaaaca gaactatgtt taatgtgtaa agattagtcg cacatcaagt catctgttac    4140
aatatgttac aacaagtcat aagcccaaca aagttagcac gtctaaataa actaaagagt    4200
ccacgaaaat attacaaatc ataagcccaa caaagttatt gatcaaaaaa aaaaaacgcc    4260
caacaaagct aaacaaagtc caaaaaaaac ttctcaagtc tccatcttcc tttatgaaca    4320
ttgaaaacta tacacaaaac aagtcagata atctctttc tgggcctgtc ttcccaacct    4380
cctacatcac ttccctatcg gattgaatgt tttacttgta ccttttccgt tgcaatgata    4440
ttgatagtat gtttgtgaaa actaataggg ttaacaatcg aagtcatgga atatggattt    4500
ggtccaagat tttccgagag ctttctagta gaaagcccat caccagaaat ttactagtaa    4560
aataaatcac caattaggtt tcttattatg tgccaaattc aatataatta tagaggatat    4620
ttcaaatgaa aacgtatgaa tgttattagt aaatggtcag gtaagacatt aaaaaaatcc    4680
tacgtcagat attcaacttt aaaaattcga tcagtgtgga attgtacaaa aatttgggat    4740
ctactatata tatataatgc tttcaacac ttggattttt ttttggaggc tggaattttt    4800
aatctacata tttgttttgg ccatgcacca actcattgtt tagtgtaata ctttgatttt    4860
gtcaaatata tgtgttcgtg tatatttgta taagaatttc tttgaccata tacacacaca    4920
catatatata tatatatata tattatatat catgcacttt taattgaaaa ataatatat    4980
atatatatag tgcatttttt ctaacaacca tatatgttgc gattgatctg caaaaatact    5040
gctagagtaa tgaaaaatat aatctattgc tgaaattatc tcagatgtta agattttctt    5100
aaagtaaatt ctttcaaatt ttagctaaaa gtcttgtaat aactaaagaa taatacacaa    5160
tctcgaccac ggaaaaaaaa cacataataa atttgaattt cgaccgcggt acccggaatt    5220
gggttataat tacctcaggt cgaggaatta attcggtacg tacctaataa cttcgtatag    5280
catacattat acgaagttat atggatctcg aggcattacg gcattacggc actcgcgagg    5340
gtcccaattc gagcatggag ccatttacaa ttgaatatat cctgccgccg ctgccgcttt    5400
gcacccggtg gagcttgcat gttggttcct acgcagaact gagccggtta ggcagataat    5460
ttccattgag aactgagcca tgtgcacctt cccccaaca cggtgagcga cggggcaacg    5520
gagtgatcca catgggactt ttaaacatca tccgtcggat ggcgttgcga gagaagcagt    5580
cgatccgtga gatcagccga cgcaccgggc aggcgcgcaa cacgatcgca aagtatttga    5640
acgcaggtac aatcgagccg acgttcacgg taccggaacg accaagcaag ctagcttagt    5700
aaagccctcg ctagatttta atgcggatgt tgcgattact tcgccaacta ttgcgataac    5760
```

```
aagaaaaagc cagcctttca tgatatatct cccaatttgt gtagggctta ttatgcacgc   5820
ttaaaaataa taaaagcaga cttgacctga tagtttggct gtgagcaatt atgtgcttag   5880
tgcatctaac gcttgagtta agccgcgccg cgaagcggcg tcggcttgaa cgaattgtta   5940
gacattattt gccgactacc ttggtgatct cgcctttcac gtagtggaca aattcttcca   6000
actgatctgc gcgcgaggcc aagcgatctt cttcttgtcc aagataagcc tgtctagctt   6060
caagtatgac gggctgatac tgggccggca ggcgctccat tgcccagtcg gcagcgacat   6120
ccttcggcgc gattttgccg gttactgcgc tgtaccaaat gcgggacaac gtaagcacta   6180
catttcgctc atcgccagcc cagtcgggcg gcgagttcca tagcgttaag gtttcattta   6240
gcgcctcaaa tagatcctgt tcaggaaccg gatcaaagag ttcctccgcc gctggaccta   6300
ccaaggcaac gctatgttct cttgcttttg tcagcaagat agccagatca atgtcgatcg   6360
tggctggctc gaagatacct gcaagaatgt cattgcgctg ccattctcca aattgcagtt   6420
cgcgcttagc tggataacgc cacggaatga tgtcgtcgtg cacaacaatg gtgacttcta   6480
cagcgcggag aatctcgctc tctccagggg aagccgaagt ttccaaaagg tcgttgatca   6540
aagctcgccg cgttgtttca tcaagcctta cggtcaccgt aaccagcaaa tcaatatcac   6600
tgtgtggctt caggccgcca tccactgcgg agccgtacaa atgtacggcc agcaacgtcg   6660
gttcgagatg gcgctcgatg acgccaacta cctctgatag ttgagtcgat acttcggcga   6720
tcaccgcttc cctcatgatg tttaactttg ttttagggcg actgccctgc tgcgtaacat   6780
cgttgctgct ccataacatc aaacatcgac ccacggcgta acgcgcttgc tgcttggatg   6840
cccgaggcat agactgtacc ccaaaaaaac agtcataaca agccatgaaa accgccactg   6900
cgccgttacc accgctgcgt tcggtcaagg ttctggacca gttgcgtgag cgcatacgct   6960
acttgcatta cagcttacga accgaacagg cttatgtcca ctgggttcgt gccttcatcc   7020
gtttccacgg tgtgcgtcac ccggcaacct tgggcagcag cgaagtcgag gcatttctgt   7080
cctggctggc gaacgagcgc aaggtttcgg tctccacgca tcgtcaggca ttggcggcct   7140
tgctgttctt ctacggcaag tgctgtgcac ggatctgccc tggcttcagg agatcggaag   7200
acctcggccg tccgggcgct tgccggtggt gctgaccccg gatgaagtct ctagagctct   7260
agagggttcg catcctcggt tttctggaag gcgagcatcg tttgttcgcc cagcttctgt   7320
atggaacggg catgcggatc agtgagggtt tgcaactgcg ggtcaaggat ctggatttcg   7380
atcacggcac gatcatcgtg cgggagggca agggctccaa ggatcgggcc ttgatgttac   7440
ccgagagctt ggcacccagc ctgcgcgagc agggatcgat ccaaccctc cgctgctata    7500
gtgcagtcgg cttctgacgt tcagtgcagc cgtcttctga aaacgacatg tcgcacaagt   7560
cctaagttac gcgacaggct gccgccctgc ccttttcctg gcgttttctt gtcgcgtgtt   7620
ttagtcgcat aaagtagaat acttgcgact agaaccggag acattacgcc atgaacaaga   7680
gcgccgccgc tggcctgctg ggctatgccc gcgtcagcac cgacgaccag gacttgacca   7740
accaacgggc cgaactgcac gcggccggct gcaccaagct gttttccgag aagatcaccg   7800
gcaccaggcg cgaccgcccg gagctggcca ggatgcttga ccacctacgc cctggcgacg   7860
ttgtgacagt gaccaggcta gaccgcctgg cccgcagcac ccgcgaccta ctggacattg   7920
ccgagcgcat ccaggaggcc ggcgcgggcc tgcgtagcct ggcagagccg tgggccgaca   7980
ccaccacgcc ggccggccgc atggtgttga ccgtgttcgc cggcattgcc gagttcgagc   8040
gttccctaat catcgaccgc acccggagcg ggcgcgaggc cgccaaggcc cgaggcgtga   8100
agtttggccc ccgccctacc ctcacccccgg cacagatcgc gcacgcccgc gagctgatcg   8160
```

```
accaggaagg ccgcaccgtg aaagaggcgg ctgcactgct tggcgtgcat cgctcgaccc    8220
tgtaccgcgc acttgagcgc agcgaggaag tgacgcccac cgaggccagg cggcgcggtg    8280
ccttccgtga ggacgcattg accgaggccg acgccctggc ggccgccgag aatgaacgcc    8340
aagaggaaca agcatgaaac cgcaccagga cggccaggac gaaccgtttt tcattaccga    8400
agagatcgag gcgagatga tcgcggccgg gtacgtgttc gagccgcccg cgcacgtctc     8460
aaccgtgcgg ctgcatgaaa tcctggccgg tttgtctgat gccaagctgg cggcctggcc    8520
ggccagcttg gccgctgaag aaaccgagcg ccgccgtcta aaaaggtgat gtgtatttga    8580
gtaaaacagc ttgcgtcatg cggtcgctgc gtatatgatg cgatgagtaa ataaacaaat    8640
acgcaagggg aacgcatgaa ggttatcgct gtacttaacc agaaaggcgg gtcaggcaag    8700
acgaccatcg caacccatct agcccgcgcc ctgcaactcg ccggggccga tgttctgtta    8760
gtcgattccg atccccaggg cagtgccgcg gattgggcgg ccgtgcggga agatcaaccg    8820
ctaaccgttg tcggcatcga ccgcccgacg attgaccgcg acgtgaaggc catcggccgg    8880
cgcgacttcg tagtgatcga cggagcgccc caggcggcgg acttggctgt gtccgcgatc    8940
aaggcagccg acttcgtgct gattccggtg cagccaagcc cttacgacat atgggccacc    9000
gccgacctgg tggagctggt taagcagcgc attgaggtca cggatggaag gctacaagcg    9060
gcctttgtcg tgtcgcgggc gatcaaaggc acgcgcatcg gcgtgaggt tgccgaggcg     9120 ctggccgggt acgagctgcc cattcttgag tcccgtatca cgcagcgcgt gagctaccca    9180
ggcactgccg ccgccggcac aaccgttctt gaatcagaac ccgagggcga cgctgcccgc    9240
gaggtccagg cgctggccgc tgaaattaaa tcaaaactca tttgagttaa tgaggtaaag    9300
agaaaatgag caaaagcaca aacacgctaa gtgccggccg tccgagcgca cgcagcagca    9360
aggctgcaac gttggccagc ctggcagaca cgccagccat gaagcgggtc aactttcagt    9420
tgccggcgga ggatcacacc aagctgaaga tgtacgcggt acgccaaggc aagaccatta    9480
ccgagctgct atctgaatac atcgcgcagc taccagagta atgagcaaa tgaataaatg    9540 agtagatgaa ttttagcggc taaggaggc ggcatggaaa atcaagaaca accaggcacc    9600
gacgccgtgg aatgccccat gtgtggagga cgggcggtt ggccaggcgt aagcggctgg     9660
gttgtctgcc ggccctgcaa tggcactgga acccccaagc ccgaggaatc ggcgtgacgg    9720
tcgcaaacca tccggcccgg tacaaatcgg cgcggcgctg ggtgatgacc tggtggagaa    9780
gttgaaggcc gcgcaggccg cccagcggca acgcatcgag gcagaagcac gccccggtga    9840
atcgtggcaa gcggccgctg atcgaatccg caaagaatcc cggcaaccgc cggcagccgg    9900
tgcgccgtcg attaggaagc cgcccaaggg cgacgagcaa ccagattttt tcgttccgat    9960
gctctatgac gtgggcaccc gcgatagtcg cagcatcatg gacgtggccg ttttccgtct   10020
gtcgaagcgt gaccgacgag ctggcgaggt gatccgctac gagcttccag acgggcacgt   10080
agaggtttcc gcagggccgg ccggcatggc cagtgtgtgg gattacgacc tggtactgat   10140 ggcggttttcc catctaaccg aatccatgaa ccgataccgg gaagggaagg gagacaagcc   10200
cggccgcgtg ttccgtccac acgttgcgga cgtactcaag ttctgccggc gagccgatgg   10260
cggaaagcag aaagacgacc tggtagaaac ctgcattcgg ttaaacacca cgcacgttgc   10320
catgcagcgt acgaagaagg ccaagaacgg ccgcctggtg acggtatccg agggtgaagc   10380
cttgattagc cgctacaaga tcgtaaagag cgaaaccggg cggccggagt acatcgagat   10440
cgagctagct gattggatgt accgcgagat cacagaaggc aagaacccgg acgtgctgac   10500
```

-continued

```
ggttcacccc gattactttt tgatcgatcc cggcatcggc cgttttctct accgcctggc   10560
acgccgcgcc gcaggcaagg cagaagccag atggttgttc aagacgatct acgaacgcag   10620
tggcagcgcc ggagagttca agaagttctg tttcaccgtg cgcaagctga tcgggtcaaa   10680
tgacctgccg gagtacgatt tgaaggagga ggcggggcag gctggcccga tcctagtcat   10740
gcgctaccgc aacctgatcg agggcgaagc atccgccggt tcctaatgta cggagcagat   10800
gctagggcaa attgccctag cagggaaaa aggtcgaaaa ggtctctttc ctgtggatag   10860
cacgtacatt gggaacccaa agccgtacat tgggaaccgg aacccgtaca ttgggaaccc   10920
aaagccgtac attgggaacc ggtcacacat gtaagtgact gatataaaag agaaaaaagg   10980 cgattttcc gcctaaaact ctttaaaact tattaaaact cttaaaaccc gcctggcctg   11040
tgcataactg tctggccagc gcacagccga agagctgcaa aaagcgccta cccttcggtc   11100
gctgcgctcc ctacgccccg ccgcttcgcg tcggcctatc gcggccgctg ccgctcaaa   11160 aatggctggc ctacgccag gcaatctacc agggcgcgga caagccgcgc cgtcgccact   11220
cgaccgccgg cgcccacatc aaggcaccct gcctcgcgcg tttcggtgat gacggtgaaa   11280
acctctgaca catgcagctc ccggagacgt tcacagcttg tctgtaagcg gatgccggga   11340
gcagacaagc ccgtcagggc gcgtcagcgg gtgttggcgg gtgtcggggc gcagccatga   11400
cccagtcacg tagcgatagc ggagtgtata ctggcttaac tatgcggcat cagagcagat   11460
tgtactgaga gtgcaccata tgcggtgtga ataccgcac agatgcgtaa ggagaaaata   11520
ccgcatcagg cgctcttccg cttcctcgct cactgactcg ctgcgctcgg tcgttcggct   11580
gcggcgagcg gtatcagctc actcaaaggc ggtaatacgg ttatccacag aatcagggga   11640
taacgcagga aagaacatgt gagcaaaagg ccagcaaaag gccaggaacc gtaaaaaggc   11700
cgcgttgctg gcgtttttcc ataggctccg ccccctgac gagcatcaca aaaatcgacg   11760
ctcaagtcag aggtggcgaa acccgacagg actataaaga taccaggcgt ttccccctgg   11820
aagctccctc gtgcgctctc ctgttccgac cctgccgctt accggatacc tgtccgcctt   11880
tctcccttcg ggaagcgtgg cgctttctca tagctcacgc tgtaggtatc tcagttcggt   11940
gtaggtcgtt cgctccaagc tgggctgtgt gcacgaaccc cccgttcagc ccgaccgctg   12000
cgccttatcc ggtaactatc gtcttgagtc caacccggta agacacgact tatcgccact   12060
ggcagcagcc actggtaaca ggattagcag agcgaggtat gtaggcggtg ctacagagtt   12120
cttgaagtgg tggcctaact acggctacac tagaaggaca gtatttggta tctgcgctct   12180
gctgaagcca gttaccttcg gaaaaagagt ggtagctctt gatccggca acaaaccac   12240 cgctggtagc ggtggttttt tgtttgcaa gcagcagatt acgcgcagaa aaaaggatc   12300 tcaagaagat ccgaaaacg caagcgcaaa gagaaagcag gtagcttgca gtgggcttac   12360
atggcgatag ctagactggg cggttttatg gacagcaagc gaaccggaat tgcc         12414
```

<210> SEQ ID NO 29
<211> LENGTH: 12366
<212> TYPE: DNA
<213> ORGANISM: Artificial
<220> FEATURE:
<223> OTHER INFORMATION: pTVE496

<400> SEQUENCE: 29

```
agattcgaag ctcggtcccg tgggtgttct gtcgtctcgt tgtacaacga aatccattcc      60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
```

```
cttattcaca cgcgacaaat tacaacggta tatatcctgc cagtactcgg ccgtcgaccg      240
cggtaccccg gaattaagct tgcatgcctg caggcaattg gccgctgtac catgcatgat      300
ctggatttta gtactggatt ttggttttag gaattagaaa ttttattgat agaagtattt      360
tacaaataca aatacatact aagggtttct tatatgctca acacatgagc gaaaccctat      420 aggaaccota attcccttat ctgggaacta ctcacacatt attatggaga aaatagagag      480
agatagattt gtagagagag actggtgatt tcagcgtgtc caagcttgct agctcattct      540
ttgtttccaa gaacttgctt aacaggttcg gtttggtcca catatagtct atgttcttgg      600
atatacctga tgaccgaatt aggtaacaaa tattgtacag acatggcgcg tctgataaat      660
agacgaactt tcgtggaaga aatatcatta tagatgagtt gcttgatgat aagaatattc      720
cttctatgtt catacataat atcatgggat aacaaaaaag accttacatc agaaccagta      780
cgttcgacaa tcaaacaacc gtaattaccg agaatgtgat gtaaatcggc gtccgcccaa      840
acgtttggtt cacccattga ctctattagg tcaccaccag ccagcaacat tattttcaca      900 ccaattttt ctccagtaac agtagctaca ccacctctct taatattgat ttcgtgattg       960
aaatgatcca agaccttggc agttcttgtg tatgaaggtt gcaatgactc ccatgcatcc     1020
accatcaacc aagatgaggt tctttcgcag gccaattcac acatacgtac tctatggtag     1080
gatggggcca agccttgctt tgatagtta tcactaacag gggagtaata tccacctatg      1140
acttcaaacc ttgtttgttc agagattgca tctaaagcca tttcaaacat tcttagatgc     1200
aagtaggtga ttggtgaaaa agacccacat gctactatta ctaacggcag tttatttgga     1260
tccagtaatt ttttcgataa tctgtgtgag gggaattcgt agtcttccaa ggttcttgct     1320
tgacgaacga ttccatgtgg aacttcttct aaatcagcaa tctgatattt ctgaacacct     1380
ctagtttctg attctgtggt tgaatctgaa ccgtatctct ccttggatct aaaatccgcg     1440
tcatcatctt cggaagacac ttctgcggaa agtggttgaa agtcgtcttg gttcaatgga     1500
atatgctgat gttttttatc attgccttct ttacgactgt gatgatggtg atgatgatgc     1560
ttaggatgct ttttcttcct cttaatatta aaggtgcat ctatagagga attcgcatcg      1620
gctaagacgt atggaataat tggaatagat ttgggaattt tagattccgg gtcgggtgga     1680
ggaatcaatt cctcgtctgc agatggcggt ttgaaatccg gagctcttgt gggatccatg     1740
gttttggttt aataagaaga gaaagagtt cttttgttat ggctgaagta atagagaaat      1800
gagctcgagt cctctccaaa tgaaatgaac ttccttatat agaggaaggg tcttgcgaag     1860
gatagtggga ttgtgcgtca tcccttacgt cagtggagat atcacatcaa tccacttgct     1920
ttgaagacgt ggttggaacg tcttcttttt ccacgatgct cctcgtgggt ggggtccat      1980 ctttgggacc actgtcggca gaggcatctt gaacgatagc cttccttta tcgcaatgat      2040 ggcatttgta ggtgccacct tcctttttcta ctgtcctttt gatgaagtga cagatagctg     2100
ggcaatggaa tccgaggagg tttcccgata ttaccctttg ttgaaaagtc tcaatagccc     2160
tttggtcttc tgagactgta tctttgatat tcttggagta gacgagagtg tcgtgctcca     2220
ccatgttgac gaagattttc ttcttgtcat tgagtcgtaa aagactctgt atgaactgtt     2280
cgccagtctt cacggcgagt tctgttagat cctcgatctg aatttttgac tccatgtatg     2340
gtgcatatgg cgcgccatat gcccgggccc tgtacagcgg ccgcgttaac gcgtatactc     2400
tagagcgatc gcccgggccg gccatttaaa tgaattcgag ctcggtaccc aaacgcggcc     2460
gcaagctata acttcgtata gcatacatta tacgaagtta ttcgactcta gaggatccca     2520
```

```
attcccatgc atggagtcaa agattcaaat agaggacact tctcgaactc ggccgtcgaa    2580
ctcggccgtc gagtacatgg tcgataagaa aaggcaattt gtagatgtta attcccatct    2640
tgaaagaaat atagtttaaa tatttattga taaaataaca agtcaggtat tatagtccaa    2700
gcaaaaacat aaatttattg atgcaagttt aaattcagaa atatttcaat aactgattat    2760
atcagctggt acattgccgt agatgaaaga ctgagtgcga tattatgtgt aatacataaa    2820
ttgatgatat agctagctta gctcatcggg ggatcctaga cgcgtgagat cagatctcgg    2880
tgacgggcag gaccggacgg ggcggtaccg gcaggctgaa gtccagctgc cagaaaccca    2940
cgtcatgcca gttcccgtgc ttgaagccgg ccgcccgcag catgccgcgg ggggcatatc    3000
cgagcgcctc gtgcatgcgc acgctcgggt cgttgggcag cccgatgaca gcgaccacgc    3060
tcttgaagcc ctgtgcctcc agggacttca gcagtgggt gtagagcgtg gagcccagtc    3120
ccgtccgctg gtggcggggg gagacgtaca cggtcgactc ggccgtccag tcgtaggcgt    3180
tgcgtgcctt ccaggggccc gcgtaggcga tgccggcgac ctcgccgtcc acctcggcga    3240
cgagccaggg atagcgctcc cgcagacgga cgaggtcgtc cgtccactcc tgcggttcct    3300
gcggctcggt acgaagttg accgtgcttg tctcgatgta gtggttgacg atggtgcaga    3360
ccgccggcat gtccgcctcg gtggcacggc ggatgtcggc cgggcgtcgt tctgggtcca    3420
ttgttcttct ttactctttg tgtgactgag gtttggtcta gtgctttggt catctatata    3480
taatgataac aacaatgaga acaagctttg gagtgatcgg agggtctagg atacatgaga    3540
ttcaagtgga ctaggatcta caccgttgga ttttgagtgt ggatatgtgt gaggttaatt    3600
ttacttggta acggccacaa aggcctaagg agaggtgttg agacccttat cggcttgaac    3660
cgctggaata atgccacgtg gaagataatt ccatgaatct tatcgttatc tatgagtgaa    3720
attgtgtgat ggtggagtgg tgcttgctca ttttacttgc ctggtggact tggccctttc    3780
cttatgggga atttatattt tacttactat agagctttca tacctttttt ttaccttgga    3840
tttagttaat atataatggt atgattcatg aataaaaatg ggaaatttt gaatttgtac     3900 tgctaaatgc ataagattag gtgaaactgt ggaatatata tttttttcat ttaaaagcaa    3960
aatttgcctt ttactagaat tataaatata gaaaatata taacattcaa ataaaaatga     4020
aaataagaac tttcaaaaaa cagaactatg tttaatgtgt aaagattagt cgcacatcaa    4080
gtcatctgtt acaatatgtt acaacaagtc ataagcccaa caaagttagc acgtctaaat    4140
aaactaaaga gtccacgaaa atattacaaa tcataagccc aacaaagtta ttgatcaaaa    4200
aaaaaaaacg cccaacaaag ctaaacaaag tccaaaaaaa acttctcaag tctccatctt    4260
cctttatgaa cattgaaaac tatacacaaa acaagtcaga taaatctctt tctgggcctg    4320
tcttcccaac ctcctacatc acttccctat cggattgaat gttttacttg tacctttttc    4380
gttgcaatga tattgatagt atgtttgtga aaactaatag ggttaacaat cgaagtcatg    4440
gaatatggat ttggtccaag atttttccgag agctttctag tagaaagccc atcaccagaa    4500
atttactagt aaaataaatc accaattagg tttcttatta tgtgccaaat tcaatataat    4560
tatagaggat atttcaaatg aaaacgtatg aatgttatta gtaaatggtc aggtaagaca    4620
ttaaaaaaat cctacgtcag atattcaact ttaaaaattc gatcagtgtg gaattgtaca    4680
aaaatttggg atctactata tatatataat gctttacaac acttggattt ttttttggag    4740
gctggaattt ttaatctaca tatttgtttt ggccatgcac caactcattg tttagtgtaa    4800
tactttgatt ttgtcaaata tatgtgttcg tgtatatttg tataagaatt tctttgacca    4860
tatacacaca cacatatata tatatatata tatattatat atcatgcact tttaattgaa    4920
```

```
aaaataatat atatatatat agtgcatttt ttctaacaac catatatgtt gcgattgatc    4980
tgcaaaaata ctgctagagt aatgaaaaat ataatctatt gctgaaatta tctcagatgt    5040
taagattttc ttaaagtaaa ttctttcaaa ttttagctaa aagtcttgta ataactaaag    5100
aataatacac aatctcgacc acggaaaaaa aacacataat aaatttgaat ttcgaccgcg    5160
gtacccggaa ttgggttata attacctcag gtcgaggaat taattcggta cgtacctaat    5220
aacttcgtat agcatacatt atacgaagtt atatggatct cgaggcatta cggcattacg    5280
gcactcgcga gggtcccaat tcgagcatgg agccatttac aattgaatat atcctgccgc    5340
cgctgccgct ttgcacccgg tggagcttgc atgttggttt ctacgcagaa ctgagccggt    5400
taggcagata atttccattg agaactgagc catgtgcacc ttcccccccaa cacggtgagc    5460 gacgggggcaa cggagtgatc cacatgggac ttttaaacat catccgtcgg atggcgttgc    5520
gagagaagca gtcgatccgt gagatcagcc gacgcaccgg gcaggcgcgc aacacgatcg    5580
caaagtattt gaacgcaggt acaatcgagc cgacgttcac ggtaccggaa cgaccaagca    5640
agctagctta gtaaagccct cgctagattt taatgcggat gttgcgatta cttcgccaac    5700
tattgcgata acaagaaaaa gccagccttt catgatatat ctcccaattt gtgtagggct    5760
tattatgcac gcttaaaaat aataaaagca gacttgacct gatagtttgg ctgtgagcaa    5820
ttatgtgctt agtgcatcta acgcttgagt taagccgcgc cgcgaagcgg cgtcggcttg    5880
aacgaattgt tagacattat ttgccgacta ccttggtgat ctcgcctttc acgtagtgga    5940
caaattcttc caactgatct gcgcgcgagg ccaagcgatc ttcttcttgt ccaagataag    6000
cctgtctagc ttcaagtatg acgggctgat actgggccgg caggcgctcc attgcccagt    6060
cggcagcgac atccttcggc gcgattttgc cggttactgc gctgtaccaa atgcgggaca    6120
acgtaagcac tacatttcgc tcatcgccag cccagtcggg cggcgagttc catagcgtta    6180
aggtttcatt tagcgcctca aatagatcct gttcaggaac cggatcaaag agttcctccg    6240
ccgctggacc taccaaggca acgctatgtt ctcttgcttt tgtcagcaag atagccagat    6300
caatgtcgat cgtggctggc tcgaagatac ctgcaagaat gtcattgcgc tgccattctc    6360
caaattgcag ttcgcgctta gctggataac gccacggaat gatgtcgtcg tgcacaacaa    6420
tggtgacttc tacagcgcgg agaatctcgc tctctccagg ggaagccgaa gtttccaaaa    6480
ggtcgttgat caaagctcgc cgcgttgttt catcaagcct tacggtcacc gtaaccagca    6540
aatcaatatc actgtgtggc ttcaggccgc catccactgc ggagccgtac aaatgtacgg    6600
ccagcaacgt cggttcgaga tggcgctcga tgacgccaac tacctctgat agttgagtcg    6660
atacttcggc gatcaccgct cccctcatga tgtttaactt tgttttaggg cgactgccct    6720
gctgcgtaac atcgttgctg ctccataaca tcaaacatcg acccacggcg taacgcgctt    6780
gctgcttgga tgcccgaggc atagactgta ccccaaaaaa acagtcataa caagccatga    6840
aaaccgccac tgcgccgtta ccaccgctgc gttcggtcaa ggttctggac cagttgcgtg    6900
agcgcatacg ctacttgcat tacagcttac gaaccgaaca ggcttatgtc cactgggttc    6960
gtgccttcat ccgtttccac ggtgtgcgtc acccggcaac cttgggcagc agcgaagtcg    7020
aggcatttct gtcctggctg gcgaacgagc gcaaggtttc ggtctccacg catcgtcagg    7080
cattggcggc cttgctgttc ttctacggca agtgctgtgc acggatctgc cctggcttca    7140
ggagatcgga agacctcggc cgtcggggcg cttgccggtg gtgctgaccc cggatgaagt    7200
ctctagagct ctagagggtt cgcatcctcg gttttctgga aggcgagcat cgtttgttcg    7260
```

```
cccagcttct gtatggaacg ggcatgcgga tcagtgaggg tttgcaactg cgggtcaagg   7320
atctggattt cgatcacggc acgatcatcg tgcgggaggg caagggctcc aaggatcggg   7380
ccttgatgtt acccgagagc ttggcaccca gcctgcgcga gcaggatcg atccaacccc    7440 tccgctgcta tagtgcagtc ggcttctgac gttcagtgca gccgtcttct gaaaacgaca   7500
tgtcgcacaa gtcctaagtt acgcgacagg ctgccgccct gccttttcc tggcgttttc    7560 ttgtcgcgtg ttttagtcgc ataaagtaga atacttgcga ctagaaccgg agacattacg   7620
ccatgaacaa gagcgccgcc gctggcctgc tgggctatgc ccgcgtcagc accgacgacc   7680
aggacttgac caaccaacgg gccgaactgc acgcggccgg ctgcaccaag ctgttttccg   7740
agaagatcac cggcaccagg cgcgaccgcc cggagctggc caggatgctt gaccacctac   7800
gccctggcga cgttgtgaca gtgaccaggc tagaccgcct ggcccgcagc acccgcgacc   7860
tactggacat tgccgagcgc atccaggagg ccggcgcggg cctgcgtagc ctggcagagc   7920
cgtgggccga caccaccacg ccggccgcc gcatggtgtt accgtgttc gccggcattg     7980 ccgagttcga gcgttcccta atcatcgacc gcacccggag cgggcgcgag gccgccaagg   8040
cccgaggcgt gaagtttggc ccccgcccta ccctcacccc ggcacagatc gcgcacgccc   8100
gcgagctgat cgaccaggaa ggccgcaccg tgaaagaggc ggctgcactg cttggcgtgc   8160
atcgctcgac cctgtaccgc gcacttgagc gcagcgagga agtgacgccc accgaggcca   8220
ggcggcgcgg tgccttccgt gaggacgcat tgaccgaggc cgacgccctg cggccgccg    8280 agaatgaacg ccaagaggaa caagcatgaa accgcaccag gacggccagg acgaaccgtt   8340
tttcattacc gaagagatcg aggcggagat gatcgcggcc gggtacgtgt tcgagccgcc   8400
cgcgcacgtc tcaaccgtgc ggctgcatga atcctggcc ggtttgtctg atgccaagct    8460
ggcggcctgg ccggccagct tggccgctga agaaaccgag cgccgccgtc taaaaaggtg   8520
atgtgtattt gagtaaaaca gcttgcgtca tgcggtcgct gcgtatatga tgcgatgagt   8580
aaataaacaa atacgcaagg ggaacgcatg aaggttatcg ctgtacttaa ccagaaaggc   8640
gggtcaggca agacgaccat cgcaacccat ctagcccgcg ccctgcaact cgccggggcc   8700
gatgttctgt tagtcgattc cgatccccag ggcagtgccc gcgattgggc ggccgtgcgg   8760
gaagatcaac cgctaaccgt tgtcggcatc gaccgcccga cgattgaccg cgacgtgaag   8820
gccatcggcc ggcgcgactt cgtagtgatc gacgagcgc cccaggcggc ggacttggct    8880
gtgtccgcga tcaaggcagc cgacttcgtg ctgattccgg tgcagccaag cccttacgac   8940
atatgggcca ccgccgacct ggtggagctg gttaagcagc gcattgaggt cacgcatgga   9000
aggctacaag cggcctttgt cgtgtcgcgg gcgatcaaag gcacgcgcat cggcggtgag   9060
gttgccgagg cgctggccgg gtacgagctg cccattcttg agtcccgtat cacgcagcgc   9120
gtgagctacc caggcactgc cgccgccggc acaaccgttc ttgaatcaga acccgagggc   9180
gacgctgccg cgaggtcca ggcgctggcc gctgaaatta atcaaaact catttgagtt     9240 aatgaggtaa agagaaaatg agcaaaagca caaacacgct aagtgccggc cgtccgagcg   9300
cacgcagcag caaggctgca acgttggcca gcctggcaga cacgccagcc atgaagcggg   9360
tcaactttca gttgccggcg gaggatcaca ccaagctgaa gatgtacgcg gtacgccaag   9420
gcaagaccat taccgagctg ctatctgaat acatcgcgca gctaccagag taaatgagca   9480
aatgaataaa tgagtagatg aattttagcg gctaaaggag gcggcatgga aaatcaagaa   9540
caaccaggca ccgacgccgt ggaatgcccc atgtgtggag gaacgggcgg ttggccaggc   9600
gtaagcggct gggttgtctg ccggccctgc aatggcactg gaacccccaa gcccgaggaa   9660
```

```
tcggcgtgac ggtcgcaaac catccggccc ggtacaaatc ggcgcggcgc tgggtgatga   9720
cctggtggag aagttgaagg ccgcgcaggc cgcccagcgg caacgcatcg aggcagaagc   9780
acgccccggt gaatcgtggc aagcggccgc tgatcgaatc cgcaaagaat cccggcaacc   9840
gccggcagcc ggtgcgccgt cgattaggaa gccgcccaag ggcgacgagc aaccagattt   9900
tttcgttccg atgctctatg acgtgggcac ccgcgatagt cgcagcatca tggacgtggc   9960
cgttttccgt ctgtcgaagc gtgaccgacg agctggcgag gtgatccgct acgagcttcc  10020
agacgggcac gtagaggttt ccgcaggggcc ggccggcatg gccagtgtgt gggattacga  10080
cctggtactg atggcggttt cccatctaac cgaatccatg aaccgatacc gggaagggaa  10140
gggagacaag cccggccgcg tgttccgtcc acacgttgcg gacgtactca agttctgccg  10200
gcgagccgat ggcggaaagc agaaagacga cctggtagaa acctgcattc ggttaaacac  10260
cacgcacgtt gccatgcagc gtacgaagaa ggccaagaac ggccgcctgg tgacggtatc  10320
cgagggtgaa gccttgatta gccgctacaa gatcgtaaag agcgaaaccg ggcggccgga  10380
gtacatcgag atcgagctag ctgattggat gtaccgcgag atcacagaag caagaaccc   10440
ggacgtgctg acggttcacc ccgattactt tttgatcgat cccggcatcg gccgttttct  10500
ctaccgcctg gcacgccgcg ccgcaggcaa ggcagaagcc agatggttgt tcaagacgat  10560
ctacgaacgc agtggcagcg ccggagagtt caagaagttc tgtttcaccg tgcgcaagct  10620
gatcgggtca aatgacctgc cggagtacga tttgaaggag gaggcggggc aggctggccc  10680
gatcctagtc atgcgctacc gcaacctgat cgagggcgag gcatccgccg gttcctaatg  10740
tacggagcag atgctagggc aaattgccct agcaggggaa aaaggtcgaa aaggtctctt  10800
tcctgtggat agcacgtaca ttgggaaccc aaagccgtac attgggaacc ggaacccgta  10860
cattgggaac ccaaagccgt acattgggaa ccggtcacac atgtaagtga ctgatataaa  10920
agagaaaaaa ggcgattttt ccgcctaaaa ctctttaaaa cttattaaaa ctcttaaaac  10980
ccgcctggcc tgtgcataac tgtctggcca gcgcacagcc gaagagctgc aaaaagcgcc  11040
tacccttcgg tcgctgcgct ccctacgccc cgccgcttcg cgtcggccta tcgcggccgc  11100
tggccgctca aaaatggctg gcctacggcc aggcaatcta ccagggcgcg gacaagccgc  11160
gccgtcgcca ctcgaccgcc ggcgcccaca tcaaggcacc ctgcctcgcg cgtttcggtg  11220
atgacggtga aaacctctga cacatgcagc tcccggagac ggtcacagct tgtctgtaag  11280
cggatgccgg gagcagacaa gcccgtcagg gcgcgtcagc gggtgttggc gggtgtcggg  11340
gcgcagccat gacccagtca cgtagcgata gcggagtgta tactggctta actatgcggc  11400
atcagagcag attgtactga gagtgcacca tatgcggtgt gaaataccgc acagatgcgt  11460
aaggagaaaa taccgcatca ggcgctcttc cgcttcctcg ctcactgact cgctgcgctc  11520
ggtcgttcgg ctgcggcgag cggtatcagc tcactcaaag gcggtaatac ggttatccac  11580
agaatcaggg gataacgcag gaaagaacat gtgagcaaaa ggccagcaaa aggccaggaa  11640
ccgtaaaaag gccgcgttgc tggcgttttt ccataggctc cgcccccctg acgagcatca  11700
caaaaatcga cgctcaagtc agaggtggcg aaacccgaca ggactataaa gataccaggc  11760
gtttccccct ggaagctccc tcgtgcgctc tcctgttccg accctgccgc ttaccggata  11820
cctgtccgcc tttctccctt cgggaagcgt ggcgctttct catagctcac gctgtaggta  11880
tctcagttcg gtgtaggtcg ttcgctccaa gctgggctgt gtgcacgaac cccccgttca  11940
gcccgaccgc tgcgccttat ccggtaacta tcgtcttgag tccaacccgg taagacacga  12000
```

-continued

| | |
|---|---|
| cttatcgcca ctggcagcag ccactggtaa caggattagc agagcgaggt atgtaggcgg | 12060 |
| tgctacagag ttcttgaagt ggtggcctaa ctacggctac actagaagga cagtatttgg | 12120 |
| tatctgcgct ctgctgaagc cagttacctt cggaaaaaga gttggtagct cttgatccgg | 12180 |
| caaacaaacc accgctggta gcggtggttt ttttgtttgc aagcagcaga ttacgcgcag | 12240 |
| aaaaaaagga tctcaagaag atccggaaaa cgcaagcgca aagagaaagc aggtagcttg | 12300 |
| cagtgggctt acatggcgat agctagactg ggcggtttta tggacagcaa gcgaaccgga | 12360 |
| attgcc | 12366 |

<210> SEQ ID NO 30
<211> LENGTH: 12384
<212> TYPE: DNA
<213> ORGANISM: Artificial
<220> FEATURE:
<223> OTHER INFORMATION: pTVE497

<400> SEQUENCE: 30

| | |
|---|---|
| agattcgaag ctcggtcccg tgggtgttct gtcgtctcgt tgtacaacga aatccattcc | 60 |
| cattccgcgc tcaagatggc ttcccctcgg cagttcatca gggctaaatc aatctagccg | 120 |
| acttgtccgg tgaaatgggc tgcactccaa cagaaacaat caaacaaaca tacacagcga | 180 |
| cttattcaca cgcgacaaat tacaacggta tatatcctgc cagtactcgg ccgtcgaccg | 240 |
| cggtacccg gaattaagct tgcatgcctg caggcaattg gccgctgtac catgcatgat | 300 |
| ctggatttta gtactggatt ttggttttag gaattagaaa ttttattgat agaagtattt | 360 |
| tacaaataca aatacatact aagggtttct tatatgctca acacatgagc gaaaccctat | 420 |
| aggaacccta attcccttat ctgggaacta ctcacacatt attatggaga aaatagagag | 480 |
| agatagattt gtagagagag actggtgatt tcagcgtgtc caagcttgct agctcattct | 540 |
| ttgtttccaa gaacttgctt aacaggttcg gtttggtcca catatagtct atgttcttgg | 600 |
| atatacctga tgaccgaatt aggtaacaaa tattgtacag acatggcgcg tctgataaat | 660 |
| agacgaactt tcgtggaaga aatatcatta tagatgagtt gcttgatgat aagaatattc | 720 |
| cttctatgtt catacataat atcatgggat aacaaaaaag accttacatc agaaccagta | 780 |
| cgttcgacaa tcaaacaacc gtaattaccg agaatgtgat gtaaatcggc gtccgcccaa | 840 |
| acgtttggtt cacccattga ctctattagg tcaccaccag ccagcaacat tattttcaca | 900 |
| ccaattttt ctccagtaac agtagctaca ccacctctct taatattgat ttcgtgattg | 960 |
| aaatgatcca agaccttggc agttcttgtg tatgaaggtt gcaatgactc ccatgcatcc | 1020 |
| accatcaacc aagatgaggt tctttcgcag gccaattcac acatacgtac tctatggtag | 1080 |
| gatggggcca agccttgctt tgatagttat tcactaacag gggagtaata tccacctatg | 1140 |
| acttcaaacc ttgtttgttc agagattgca tctaaagcca tttcaaacat tcttagatgc | 1200 |
| aagtaggtga ttggtgaaaa agacccacat gctactatta ctaacggcag tttatttgga | 1260 |
| tccagtaatt ttttcgataa tctgtgtgag gggaattcgt agtcttccaa ggttcttgct | 1320 |
| tgacgaacga ttccatgtgg aacttcttct aaatcagcaa tctgatattt ctgaacacct | 1380 |
| ctagtttctg attctgtggt tgaatctgaa ccgtatctct ccttggatct aaaatccgcg | 1440 |
| tcatcatctt cggaagacac ttctgcggaa agtggttgaa agtcgtcttg gttcaatgga | 1500 |
| atatgctgat gttttttatc attgccttct ttacgactgt gatgatggtg atgatgatgc | 1560 |
| ttaggatgct ttttcttcct cttaatatta aaggtgcat ctatagagga attcgcatcg | 1620 |
| gctaagacgt atgaataat tggaatagat ttgggaattt tagattccgg gtcgggtgga | 1680 |

```
ggaatcaatt cctcgtctgc agatggcggt ttgaaatccg agctcttgt aaccttgcgc    1740 ttcttcttgg gatccatggt tttggtttaa taagaagaga aaagagttct tttgttatgg    1800
ctgaagtaat agagaaatga gctcgagtcc tctccaaatg aaatgaactt ccttatatag    1860
aggaagggtc ttgcgaagga tagtgggatt gtgcgtcatc ccttacgtca gtggagatat    1920
cacatcaatc cacttgcttt gaagacgtgg ttggaacgtc ttcttttcc acgatgctcc     1980 tcgtgggtgg gggtccatct ttgggaccac tgtcggcaga ggcatcttga acgatagcct    2040
ttcctttatc gcaatgatgg catttgtagg tgccacctc ctttctact gtccttttga     2100 tgaagtgaca gatagctggg caatggaatc cgaggaggtt tcccgatatt accctttgtt    2160
gaaaagtctc aatagccctt tggtcttctg agactgtatc tttgatattc ttggagtaga    2220
cgagagtgtc gtgctccacc atgttgacga agattttctt cttgtcattg agtcgtaaaa    2280
gactctgtat gaactgttcg ccagtcttca cggcgagttc tgttagatcc tcgatctgaa    2340 ttttgactc catgtatggt gcatatggcg cgccatatgc ccgggccctg tacagcggcc     2400
gcgttaacgc gtatactcta gagcgatcgc ccgggccggc catttaaatg aattcgagct    2460
cggtacccaa acgcggccgc aagctataac ttcgtatagc atacattata cgaagttatt    2520
cgactctaga ggatcccaat tcccatgcat ggagtcaaag attcaaatag aggacacttc    2580
tcgaactcgg ccgtcgaact cggccgtcga gtacatggtc gataagaaaa gcaatttgt     2640 agatgttaat tcccatcttg aaagaaatat agtttaaata tttattgata aaataacaag    2700
tcaggtatta tagtccaagc aaaaacataa atttattgat gcaagtttaa attcagaaat    2760
atttcaataa ctgattatat cagctggtac attgccgtag atgaaagact gagtgcgata    2820
ttatgtgtaa tacataaatt gatgatatag ctagcttagc tcatcggggg atcctagacg    2880
cgtgagatca gatctcggtg acgggcagga ccggacgggg cggtaccggc aggctgaagt    2940
ccagctgcca gaaacccacg tcatgccagt tcccgtgctt gaagccggcc gcccgcagca    3000
tgccgcgggg ggcatatccg agcgcctcgt gcatgcgcac gctcgggtcg ttgggcagcc    3060
cgatgacagc gaccacgctc ttgaagccct gtgcctccag ggacttcagc aggtgggtgt    3120
agagcgtgga gcccagtccc gtccgctggt ggcggggga gacgtacacg gtcgactcgg    3180
ccgtccagtc gtaggcgttg cgtgccttcc aggggcccgc gtaggcgatg ccggcgacct    3240
cgccgtccac ctcggcgacg agccagggat agcgctcccg cagacggacg aggtcgtccg    3300
tccactcctg cggttcctgc ggctcggtac ggaagttgac cgtgcttgtc tcgatgtagt    3360
ggttgacgat ggtgcagacc gccggcatgt ccgcctcggt ggcacggcgg atgtcggccg    3420
ggcgtcgttc tgggtccatt gttcttcttt actctttgtg tgactgaggt ttggtctagt    3480
gctttggtca tctatatata atgataacaa caatgagaac aagctttgga gtgatcggag    3540
ggtctaggat acatgagatt caagtggact aggatctaca ccgttggatt ttgagtgtgg    3600
atatgtgtga ggttaatttt acttggtaac ggccacaaag gcctaaggag aggtgttgag    3660
acccttatcg gcttgaaccg ctggaataat gccacgtgga agataattcc atgaatctta    3720
tcgttatcta tgagtgaaat tgtgtgatgg tggagtggtg cttgctcatt ttacttgcct    3780
ggtggacttg gcccttttcct tatggggaat ttatatttta cttactatag gctttcata    3840 cctttttttt accttggatt tagttaatat ataatggtat gattcatgaa taaaaatggg    3900
aaatttttga atttgtactg ctaaatgcat aagattaggt gaaactgtgg aatatatatt    3960
tttttcattt aaaagcaaaa tttgcctttt actagaatta taaatataga aaatatata    4020
```

```
acattcaaat aaaaatgaaa ataagaactt tcaaaaaaca gaactatgtt taatgtgtaa    4080
agattagtcg cacatcaagt catctgttac aatatgttac aacaagtcat aagcccaaca    4140
aagttagcac gtctaaataa actaaagagt ccacgaaaat attacaaatc ataagcccaa    4200
caaagttatt gatcaaaaaa aaaaaacgcc caacaaagct aaacaaagtc caaaaaaaac    4260
ttctcaagtc tccatcttcc tttatgaaca ttgaaaacta tacacaaaac aagtcagata    4320
aatctctttc tgggcctgtc ttcccaacct cctacatcac ttccctatcg gattgaatgt    4380
tttacttgta cctttccgt tgcaatgata ttgatagtat gtttgtgaaa actaataggg    4440
ttaacaatcg aagtcatgga atatggattt ggtccaagat tttccgagag ctttctagta    4500
gaaagcccat caccagaaat ttactagtaa aataaatcac caattaggtt tcttattatg    4560
tgccaaattc aatataatta tagaggtat ttcaaatgaa aacgtatgaa tgttattagt    4620
aaatggtcag gtaagacatt aaaaaaatcc tacgtcagat attcaacttt aaaaattcga    4680
tcagtgtgga attgtacaaa aatttgggat ctactatata tatataatgc tttacaacac    4740
ttggattttt ttttggaggc tggaattttt aatctacata tttgttttgg ccatgcacca    4800
actcattgtt tagtgtaata ctttgatttt gtcaaatata tgtgttcgtg tatatttgta    4860
taagaatttc tttgaccata tacacacaca catatatata tatatatata tattatatat    4920
catgcacttt taattgaaaa aataatatat atatatatag tgcattttt ctaacaacca    4980 tatatgttgc gattgatctg caaaaatact gctagagtaa tgaaaaatat aatctattgc    5040
tgaaattatc tcagatgtta agatttctt aaagtaaatt ctttcaaatt ttagctaaaa    5100
gtcttgtaat aactaaagaa taatacacaa tctcgaccac ggaaaaaaaa cacataataa    5160
atttgaattt cgaccgcggt acccggaatt gggttataat tacctcaggt cgaggaatta    5220
attcggtacg tacctaataa cttcgtatag catacattat acgaagttat atggatctcg    5280
aggcattacg gcattacggc actcgcgagg gtcccaattc gagcatggag ccatttacaa    5340
ttgaatatat cctgccgccg ctgccgcttt gcacccggtg gagcttgcat gttggtttct    5400
acgcagaact gagccggtta ggcagataat ttccattgag aactgagcca tgtgcacctt    5460
ccccccaaca cggtgagcga cggggcaacg gagtgatcca catgggactt ttaaacatca    5520
tccgtcggat ggcgttgcga gagaagcagt cgatccgtga gatcagccga cgcaccgggc    5580
aggcgcgcaa cacgatcgca aagtatttga acgcaggtac aatcgagccg acgttcacgg    5640
taccggaacg accaagcaag ctagcttagt aaagccctcg ctagatttta atgcggatgt    5700
tgcgattact tcgccaacta ttgcgataac aagaaaaagc cagccttttca tgatatatct    5760 cccaatttgt gtagggctta ttatgcacgc ttaaaaataa taaaagcaga cttgacctga    5820
tagtttggct gtgagcaatt atgtgcttag tgcatctaac gcttgagtta agccgcgccg    5880
cgaagcggcg tcggcttgaa cgaattgtta gacattattt gccgactacc ttggtgatct    5940
cgcctttcac gtagtggaca aattcttcca actgatctgc gcgcgaggcc aagcgatctt    6000
cttcttgtcc aagataagcc tgtctagctt caagtatgac gggctgatac tgggccggca    6060
ggcgctccat tgcccagtcg gcagcgacat ccttcggcgc gattttgccg gttactgcgc    6120
tgtaccaaat gcgggacaac gtaagcacta catttcgctc atcgccagcc cagtcgggcg    6180
gcgagttcca tagcgttaag gtttcattta gcgcctcaaa tagatcctgt tcaggaaccg    6240
gatcaaagag ttcctccgcc gctggaccta ccaaggcaac gctatgttct cttgcttttg    6300
tcagcaagat agccagatca atgtcgatcg tggctggctc gaagatacct gcaagaatgt    6360
cattgcgctg ccattctcca aattgcagtt cgcgcttagc tggataacgc cacggaatga    6420
```

```
tgtcgtcgtg cacaacaatg gtgacttcta cagcgcggag aatctcgctc tctccagggg   6480
aagccgaagt ttccaaaagg tcgttgatca aagctcgccg cgttgtttca tcaagcctta   6540
cggtcaccgt aaccagcaaa tcaatatcac tgtgtggctt caggccgcca tccactgcgg   6600
agccgtacaa atgtacggcc agcaacgtcg gttcgagatg gcgctcgatg acgccaacta   6660
cctctgatag ttgagtcgat acttcggcga tcaccgcttc cctcatgatg tttaactttg   6720
ttttagggcg actgccctgc tgcgtaacat cgttgctgct ccataacatc aaacatcgac   6780
ccacggcgta acgcgcttgc tgcttggatg cccgaggcat agactgtacc ccaaaaaaac   6840
agtcataaca agccatgaaa accgccactg cgccgttacc accgctgcgt tcggtcaagg   6900
ttctggacca gttgcgtgag cgcatacgct acttgcatta cagcttacga accgaacagg   6960
cttatgtcca ctgggttcgt gccttcatcc gtttccacgg tgtgcgtcac ccggcaacct   7020
tgggcagcag cgaagtcgag gcatttctgt cctggctggc gaacgagcgc aaggtttcgg   7080
tctccacgca tcgtcaggca ttggcggcct tgctgttctt ctacggcaag tgctgtgcac   7140
ggatctgccc tggcttcagg agatcggaag acctcggccg tccggcgct tgccggtggt    7200 gctgaccccg gatgaagtct ctagagctct agagggttcg catcctcggt tttctggaag   7260
gcgagcatcg tttgttcgcc cagcttctgt atggaacggg catgcggatc agtgagggtt   7320
tgcaactgcg ggtcaaggat ctggatttcg atcacggcac gatcatcgtg cgggagggca   7380
agggctccaa ggatcgggcc ttgatgttac ccgagagctt ggcacccagc ctgcgcgagc   7440
agggatcgat ccaacccctc cgctgctata gtgcagtcgg cttctgacgt tcagtgcagc   7500
cgtcttctga aaacgacatg tcgcacaagt cctaagttac gcgacaggct gccgccctgc   7560
ccttttcctg gcgttttctt gtcgcgtgtt ttagtcgcat aaagtagaat acttgcgact   7620
agaaccggag acattacgcc atgaacaaga gcgccgccgc tggcctgctg gctatgccc    7680 gcgtcagcac cgacgaccag gacttgacca accaacgggc cgaactgcac gcggccggct   7740
gcaccaagct gttttccgag aagatcaccg gcaccaggcg cgaccgcccg gagctggcca   7800
ggatgcttga ccacctacgc cctggcgacg ttgtgacagt gaccaggcta gaccgcctgg   7860
cccgcagcac ccgcgaccta ctggacattg ccgagcgcat ccaggaggcc ggcgcgggcc   7920
tgcgtagcct ggcagagccg tgggccgaca ccaccacgcc ggccggccgc atggtgttga   7980
ccgtgttcgc cggcattgcc gagttcgagc gttccctaat catcgaccgc acccggagcg   8040
ggcgcgaggc cgccaaggcc cgaggcgtga agtttggccc ccgccctacc ctcaccccgg   8100
cacagatcgc gcacgcccgc gagctgatcg accaggaagg ccgcaccgtg aaagaggcgg   8160
ctgcactgct tggcgtgcat cgctcgaccc tgtaccgcgc acttgagcgc agcgaggaag   8220
tgacgcccac cgaggccagg cggcgcggtg ccttccgtga ggacgcattg accgaggccg   8280
acgccctggc ggccgccgag aatgaacgcc aagaggaaca agcatgaaac cgcaccagga   8340
cggccaggac gaaccgtttt tcattaccga agagatcgag gcggagatga tcgcggccgg   8400
gtacgtgttc gagccgcccg cgcacgtctc aaccgtgcgg ctgcatgaaa tcctggccgg   8460
tttgtctgat gccaagctgg cggcctggcc ggccagcttg gccgctgaag aaaccgagcg   8520
ccgccgtcta aaaggtgat gtgtatttga gtaaaacagc ttgcgtcatg cggtcgctgc    8580
gtatatgatg cgatgagtaa ataaacaaat acgcaagggg aacgcatgaa ggttatcgct   8640
gtacttaacc agaaaggcgg gtcaggcaag acgaccatcg caacccatct agcccgcgcc   8700
ctgcaactcg ccggggccga tgttctgtta gtcgattccg atcccagggg cagtgcccgc   8760
```

```
gattgggcgg ccgtgcggga agatcaaccg ctaaccgttg tcggcatcga ccgcccgacg   8820
attgaccgcg acgtgaaggc catcggccgg cgcgacttcg tagtgatcga cggagcgccc   8880
caggcggcgg acttggctgt gtccgcgatc aaggcagccg acttcgtgct gattccggtg   8940
cagccaagcc cttacgacat atgggccacc gccgacctgg tggagctggt taagcagcgc   9000
attgaggtca cggatggaag gctacaagcg gcctttgtcg tgtcgcgggc gatcaaaggc   9060
acgcgcatcg gcggtgaggt tgccgaggcg ctggccgggt acgagctgcc cattcttgag   9120
tcccgtatca cgcagcgcgt gagctaccca ggcactgccg ccgccggcac aaccgttctt   9180
gaatcagaac ccgagggcga cgctgcccgc gaggtccagg cgctggccgc tgaaattaaa   9240
tcaaaactca tttgagttaa tgaggtaaag agaaaatgag caaaagcaca aacacgctaa   9300
gtgccggccg tccgagcgca cgcagcagca aggctgcaac gttggccagc ctggcagaca   9360
cgccagccat gaagcgggtc aactttcagt tgccggcgga ggatcacacc aagctgaaga   9420
tgtacgcggt acgccaaggc aagaccatta ccgagctgct atctgaatac atcgcgcagc   9480
taccagagta aatgagcaaa tgaataaatg agtagatgaa ttttagcggc taaggaggc   9540 ggcatggaaa atcaagaaca accaggcacc gacgccgtgg aatgccccat gtgtggagga   9600
acgggcggtt ggccaggcgt aagcggctgg gttgtctgcc ggcctgcaa tggcactgga   9660 accccaagc ccgaggaatc ggcgtgacgg tcgcaaacca tccggcccgg tacaaatcgg   9720
cgcggcgctg ggtgatgacc tggtggagaa gttgaaggcc gcgcaggccg cccagcggca   9780
acgcatcgag gcagaagcac gccccggtga atcgtggcaa gcggccgctg atcgaatccg   9840
caaagaatcc cggcaaccgc cggcagccgg tgcgccgtcg attaggaagc cgcccaaggg   9900
cgacgagcaa ccagattttt tcgttccgat gctctatgac gtgggcaccc gcgatagtcg   9960
cagcatcatg gacgtggccg ttttccgtct gtcgaagcgt gaccgacgag ctggcgaggt  10020
gatccgctac gagcttccag acgggcacgt agaggtttcc gcagggccgg ccggcatggc  10080
cagtgtgtgg gattacgacc tggtactgat ggcggttcc catctaaccg aatccatgaa  10140
ccgataccgg gaagggaagg gagacaagcc cggccgcgtg ttccgtccac acgttgcgga  10200
cgtactcaag ttctgccggc gagccgatgg cggaaagcag aaagacgacc tggtagaaac  10260
ctgcattcgg ttaaacacca cgcacgttgc catgcagcgt acgaagaagg ccaagaacgg  10320
ccgcctggtg acggtatccg agggtgaagc cttgattagc cgctacaaga tcgtaaagag  10380
cgaaaccggg cggccggagt acatcgagat cgagctagct gattggatgt accgcgagat  10440
cacagaaggc aagaacccgg acgtgctgac ggttcacccc gattactttt tgatcgatcc  10500
cggcatcggc cgttttctct accgcctggc acgccgcgcc gcaggcaagg cagaagccag  10560
atggttgttc aagacgatct acgaacgcag tggcagcgcc ggagagttca agaagttctg  10620
tttcaccgtg cgcaagctga tcgggtcaaa tgacctgccg gagtacgatt tgaaggagga  10680 ggcgggcag ctggcccga tcctagtcat gcgctaccgc aacctgatcg agggcgaagc  10740
atccgccggt tcctaatgta cggagcagat gctagggcaa attgccctag caggggaaaa  10800
aggtcgaaaa ggtctctttc ctgtggatag cacgtacatt gggaacccaa agccgtacat  10860
tgggaaccgg aacccgtaca ttgggaaccc aaagccgtac attgggaacc ggtcacacat  10920
gtaagtgact gatataaaag agaaaaaggc gatttttcc gcctaaaact ctttaaaact  10980
tattaaaact cttaaaaccc gcctggcctg tgcataactg tctggccagc gcacagccga  11040
agagctgcaa aaagcgccta cccttcggtc gctgcgctcc ctacgccccg ccgcttcgcg  11100
tcggcctatc gcggccgctg gccgctcaaa aatggctggc ctacggccag gcaatctacc  11160
```

```
agggcgcgga caagccgcgc cgtcgccact cgaccgccgg cgcccacatc aaggcaccct    11220
gcctcgcgcg tttcggtgat gacggtgaaa acctctgaca catgcagctc ccggagacgg    11280
tcacagcttg tctgtaagcg gatgccggga gcagacaagc ccgtcagggc gcgtcagcgg    11340
gtgttggcgg gtgtcggggc gcagccatga cccagtcacg tagcgatagc ggagtgtata    11400
ctggcttaac tatgcggcat cagagcagat tgtactgaga gtgcaccata tgcggtgtga    11460
aataccgcac agatgcgtaa ggagaaaata ccgcatcagg cgctcttccg cttcctcgct    11520
cactgactcg ctgcgctcgg tcgttcggct gcggcgagcg gtatcagctc actcaaaggc    11580
ggtaatacgg ttatccacag aatcagggga taacgcagga agaacatgt gagcaaaagg    11640 ccagcaaaag gccaggaacc gtaaaaaggc cgcgttgctg gcgtttttcc ataggctccg    11700
cccccctgac gagcatcaca aaaatcgacg ctcaagtcag aggtggcgaa acccgacagg    11760
actataaaga taccaggcgt ttccccctgg aagctccctc gtgcgctctc ctgttccgac    11820
cctgccgctt accggatacc tgtccgcctt tctcccttcg ggaagcgtgg cgctttctca    11880
tagctcacgc tgtaggtatc tcagttcggt gtaggtcgtt cgctccaagc tgggctgtgt    11940
gcacgaaccc cccgttcagc ccgaccgctg cgccttatcc ggtaactatc gtcttgagtc    12000
caacccggta agacacgact tatcgccact ggcagcagcc actggtaaca ggattagcag    12060
agcgaggtat gtaggcggtg ctacagagtt cttgaagtgg tggcctaact acggctacac    12120
tagaaggaca gtatttggta tctgcgctct gctgaagcca gttaccttcg gaaaaagagt    12180
tggtagctct tgatccggca aacaaaccac cgctggtagc ggtggttttt ttgtttgcaa    12240
gcagcagatt acgcgcagaa aaaaaggatc tcaagaagat ccggaaaacg caagcgcaaa    12300
gagaaagcag gtagcttgca gtgggcttac atggcgatag ctagactggg cggttttatg    12360
gacagcaagc gaaccggaat tgcc                                          12384
```

<210> SEQ ID NO 31
<211> LENGTH: 12348
<212> TYPE: DNA
<213> ORGANISM: Artificial
<220> FEATURE:
<223> OTHER INFORMATION: pTVE 500

<400> SEQUENCE: 31

```
agattcgaag ctcggtcccg tgggtgttct gtcgtctcgt tgtacaacga aatccattcc    60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggatttta gtactggatt ttggttttag gaattagaaa ttttattgat agaagtattt    360
tacaaataca aatacatact aagggtttct tatatgctca acacatgagc gaaaccctat    420 aggaaccccta attcccttat ctgggaacta ctcacacatt attatggaga aaatagagag    480
agatagattt gtagagagag actggtgatt tcagcgtgtc caagcttgct agctcactct    540
ttgctatcca agacctgctt gaccggttca ctttgattaa tgtatagatt atactcttgg    600
atgtaacgga tgacagagtt tggaagaaga tattgaactg acattccacg tctgatgaaa    660
agccgcactt tcgtagagga atatcattg taaataagtt gtttgataat aaggatattt    720
cttctgtgtt catacatgat atcatgggaa agcgagaagg acctaacatc agaaccagtc    780
```

```
ctttccacga tcaaacatcc ataattaccc aaaatatggt gcaggtctga atcagcccac    840
acatgaggct cgcccatgga ttcgataaga tcaccgcctg ccaataacat gatttttacg    900 cccattttt  caccatctac agtcatgatt ccacctctct tgatatttat ttcatgattg    960
aaatggtcca agacttttgc tgtccttgta aacttgatt gtaaagattc ccaggcatca    1020
accattaacc aagatgatgt ccgctcgcat gctaattcgc acatgcggac acgatgataa    1080 gctgggcta  accctcgctt tgatagtta  tcacttactg gagaaaaata accaccaacc    1140
acttcaaaac gcgtttgctc attgatatca tctaaagcca tttcaaacat tctcaaatgt    1200
aggtatgtta tgggagaaaa tgatccacaa gcaacgatga tcagaggcag tttttcagga    1260
tcttgtaact ttttcgtcaa tctgtgtaca ggaaattcgt aatcttcaat agttctggct    1320
tgtcttacaa ttgtgtgagg aacttcttcc aaatcagcaa tttggctctt cagtaccccc    1380
aaattcccag tcatcgtaac atcctgtaga gtagcgtcaa ttccattcga ttgcccttca    1440
ctttcctcct ccgatgatac atcccgagat agtggctgga agtcactagt atttaatgga    1500
atatggtcca ttcggttgct tgagttggcg ttttttttcc ttgacgacag gttttgtaa    1560 atgtcgagat tgaaaggagc atcgatcgaa gaattataat cagctaaaac atatggaact    1620
atgggtccag atttggcat  cgtatgtgtt ggatctggcg gtggttgtag ttcttcattt    1680
ggctgtggcg gtttaaaatc gggtgctttg gtgggatcca tggttttggt ttaataagaa    1740
gagaaaagag ttcttttgtt atggctgaag taatagagaa atgagctcga gtcctctcca    1800
aatgaaatga acttccttat atagaggaag ggtcttgcga aggatagtgg gattgtgcgt    1860
catcccttac gtcagtggag atatcacatc aatccacttg ctttgaagac gtggttggaa    1920
cgtcttcttt ttccacgatg ctcctcgtgg gtgggggtcc atctttggga ccactgtcgg    1980
cagaggcatc ttgaacgata gcctttcctt tatcgcaatg atggcatttg taggtgccac    2040
cttccttttc tactgtcctt ttgatgaagt gacagatagc tgggcaatgg aatccgagga    2100
ggtttcccga tattacccct tgttgaaaag tctcaatagc cctttggtct tctgagactg    2160
tatctttgat attcttggag tagacgagag tgtcgtgctc caccatgttg acgaagattt    2220
tcttcttgtc attgagtcgt aaaagactct gtatgaactg ttcgccagtc ttcacggcga    2280
gttctgttag atcctcgatc tgaatttttg actccatgta tggtgcatat ggcgcgccat    2340
atgcccgggc cctgtacagc ggccgcgtta acgcgtatac tctagagcga tcgcccgggc    2400
cggccattta aatgaattcg agctcggtac ccaaacgcgg ccgcaagcta taacttcgta    2460
tagcatacat tatacgaagt tattcgactc tagaggatcc caattcccat gcatggagtc    2520
aaagattcaa atagaggaca cttctcgaac tcggccgtcg aactcggccg tcgagtacat    2580
ggtcgataag aaaaggcaat ttgtagatgt taattcccat cttgaaagaa atatagttta    2640
aatatttatt gataaaataa caagtcaggt attatagtcc aagcaaaaac ataaatttat    2700
tgatgcaagt ttaaattcag aaatatttca ataactgatt atatcagctg gtacattgcc    2760
gtagatgaaa gactgagtgc gatattatgt gtaatacata aattgatgat atagctagct    2820
tagctcatcg ggggatccta gacgcgtgag atcagatctc ggtgacgggc aggaccggac    2880
ggggcggtac cggcaggctg aagtccagct gccagaaacc cacgtcatgc cagttcccgt    2940
gcttgaagcc ggccgcccgc agcatgccgc gggggggcata tccgagcgcc tcgtgcatgc    3000
gcacgctcgg gtcgttgggc agcccgatga cagcgaccac gctcttgaag ccctgtgcct    3060
ccagggactt cagcaggtgg gtgtagagcg tggagcccag tcccgtccgc tggtggcggg    3120
gggagacgta cacggtcgac tcggccgtcc agtcgtaggc gttgcgtgcc ttccaggggc    3180
```

-continued

```
ccgcgtaggc gatgccggcg acctcgccgt ccacctcggc gacgagccag ggatagcgct    3240
cccgcagacg gacgaggtcg tccgtccact cctgcggttc ctgcggctcg gtacggaagt    3300
tgaccgtgct tgtctcgatg tagtggttga cgatggtgca gaccgccggc atgtccgcct    3360
cggtggcacg gcggatgtcg gccgggcgtc gttctgggtc cattgttctt ctttactctt    3420
tgtgtgactg aggtttggtc tagtgctttg gtcatctata taatgata acaacaatga     3480
gaacaagctt tggagtgatc ggagggtcta ggatacatga gattcaagtg gactaggatc    3540
tacaccgttg gattttgagt gtggatatgt gtgaggttaa ttttacttgg taacggccac    3600
aaaggcctaa ggagaggtgt tgagacccctt atcggcttga accgctggaa taatgccacg   3660
tggaagataa ttccatgaat cttatcgtta tctatgagtg aaattgtgtg atggtggagt    3720
ggtgcttgct cattttactt gcctggtgga cttggcccctt tccttatggg gaatttatat   3780
tttacttact atagagcttt cataccttttt ttttaccttg gatttagtta atatataatg   3840
gtatgattca tgaataaaaa tgggaaattt ttgaatttgt actgctaaat gcataagatt    3900
aggtgaaact gtggaatata tattttttc atttaaaagc aaaatttgcc ttttactaga     3960
attataaata tagaaaaata tataacattc aaataaaaat gaaaataaga actttcaaaa    4020
aacagaacta tgtttaatgt gtaaagatta gtcgcacatc aagtcatctg ttacaatatg    4080
ttacaacaag tcataagccc aacaaagtta gcacgtctaa ataaactaaa gagtccacga    4140
aaatattaca aatcataagc ccaacaaagt tattgatcaa aaaaaaaaaa cgcccaacaa    4200
agctaaacaa agtccaaaaa aaacttctca agtctccatc ttcctttatg aacattgaaa    4260
actatacaca aaacaagtca gataaatctc tttctgggcc tgtcttccca acctcctaca    4320
tcacttccct atcggattga atgttttact tgtacctttt ccgttgcaat gatattgata    4380
gtatgtttgt gaaaactaat agggttaaca atcgaagtca tggaatatgg atttggtcca    4440
agattttccg agagctttct agtagaaagc ccatcaccag aaatttacta gtaaaataaa    4500
tcaccaatta ggtttcttat tatgtgccaa attcaatata attatagagg atatttcaaa    4560
tgaaaacgta tgaatgttat tagtaaatgg tcaggtaaga cattaaaaaa atcctacgtc    4620
agatattcaa cttttaaaaat tcgatcagtg tggaattgta caaaaatttg ggatctacta   4680
tatatatata atgctttaca acacttggat tttttttgg aggctggaat ttttaatcta    4740
catatttgtt ttggccatgc accaactcat tgtttagtgt aatactttga ttttgtcaaa    4800
tatatgtgtt cgtgtatatt tgtataagaa tttctttgac catatacaca cacacatata    4860
tatatatata tatatattat atatcatgca cttttaattg aaaaaataat atatatatat    4920
atagtgcatt ttttctaaca accatatatg ttgcgattga tctgcaaaaa tactgctaga    4980
gtaatgaaaa atataatcta ttgctgaaat tatctcagat gttaagattt tcttaaagta    5040
aattctttca aattttagct aaaagtcttg taataactaa agaataatac acaatctcga    5100
ccacggaaaa aaaacacata ataaatttga atttcgaccg cggtacccgg aattgggtta    5160
taattacctc aggtcgagga attaattcgg tacgtaccta ataacttcgt atagcataca    5220
ttatacgaag ttatatggat ctcgaggcat tacggcatta cggcactcgc gagggtccca    5280
attcgagcat ggagccattt acaattgaat atatcctgcc gccgctgccg ctttgcaccc    5340
ggtggagctt gcatgttggt ttctacgcag aactgagccg gttaggcaga taatttccat    5400
tgagaactga gccatgtgca ccttccccccc aacacggtga gcgacggggc aacggagtga    5460
tccacatggg actttttaaac atcatccgtc ggatggcgtt gcgagagaag cagtcgatcc    5520
```

```
gtgagatcag ccgacgcacc gggcaggcgc gcaacacgat cgcaaagtat ttgaacgcag   5580
gtacaatcga gccgacgttc acggtaccgg aacgaccaag caagctagct tagtaaagcc   5640
ctcgctagat tttaatgcgg atgttgcgat tacttcgcca actattgcga taacaagaaa   5700
aagccagcct ttcatgatat atctcccaat ttgtgtaggg cttattatgc acgcttaaaa   5760
ataataaaag cagacttgac ctgatagttt ggctgtgagc aattatgtgc ttagtgcatc   5820
taacgcttga gttaagccgc gccgcgaagc ggcgtcggct tgaacgaatt gttagacatt   5880
atttgccgac taccttggtg atctcgcctt tcacgtagtg gacaaattct tccaactgat   5940
ctgcgcgcga ggccaagcga tcttcttctt gtccaagata agcctgtcta gcttcaagta   6000
tgacgggctg atactgggcc ggcaggcgct ccattgccca gtcggcagcg acatccttcg   6060
gcgcgatttt gccggttact cgctgtacc aaatgcggga caacgtaagc actacatttc    6120
gctcatcgcc agcccagtcg ggcggcgagt tccatagcgt taaggtttca tttagcgcct   6180
caaatagatc ctgttcagga accggatcaa agagttcctc cgccgctgga cctaccaagg   6240
caacgctatg ttctcttgct tttgtcagca agatagccag atcaatgtcg atcgtggctg   6300
gctcgaagat acctgcaaga atgtcattgc gctgccattc tccaaattgc agttcgcgct   6360
tagctggata acgccacgga atgatgtcgt cgtgcacaac aatggtgact tctacagcgc   6420
ggagaatctc gctctctcca ggggaagccg aagtttccaa aaggtcgttg atcaaagctc   6480
gccgcgttgt ttcatcaagc cttacggtca ccgtaaccag caaatcaata tcactgtgtg   6540
gcttcaggcc gccatccact gcggagccgt acaaatgtac ggccagcaac gtcggttcga   6600
gatggcgctc gatgacgcca actacctctg atagttgagt cgatacttcg gcgatcaccg   6660
cttccctcat gatgtttaac tttgttttag ggcgactgcc ctgctgcgta acatcgttgc   6720
tgctccataa catcaaacat cgacccacgg cgtaacgcgc ttgctgcttg gatgcccgag   6780
gcatagactg tacccaaaaa aaacagtcat aacaagccat gaaaaccgcc actgcgccgt   6840
taccaccgct gcgttcggtc aaggttctgg accagttgcg tgagcgcata cgctacttgc   6900
attacagctt acgaaccgaa caggcttatg tccactgggt tcgtgccttc atccgtttcc   6960
acggtgtgcg tcacccggca accttgggca gcagcgaagt cgaggcattt ctgtcctggc   7020
tggcgaacga gcgcaaggtt tcggtctcca cgcatcgtca ggcattggcg gccttgctgt   7080
tcttctacgg caagtgctgt gcacggatct gccctggctt caggagatcg gaagacctcg   7140
gccgtccggg cgcttgccgg tggtgctgac cccggatgaa gtctctagag ctctagaggg   7200
ttcgcatcct cggttttctg gaaggcgagc atcgtttgtt cgcccagctt ctgtatggaa   7260
cgggcatgcg gatcagtgag ggtttgcaac tgcgggtcaa ggatctggat ttcgatcacg   7320
gcacgatcat cgtgcgggag ggcaagggct ccaaggatcg ggccttgatg ttacccgaga   7380
gcttggcacc cagcctgcgc gagcagggat cgatccaacc cctccgctgc tatagtgcag   7440
tcggcttctg acgttcagtg cagccgtctt ctgaaaacga catgtcgcac aagtcctaag   7500
ttacgcgaca ggctgccgcc ctgcccttt cctggcgttt tcttgtcgcg tgttttagtc    7560
gcataaagta gaatacttgc gactagaacc ggagacatta cgccatgaac aagagcgccg   7620
ccgctggcct gctgggctat gcccgcgtca gcaccgacga ccaggacttg accaaccaac   7680
gggccgaact gcacgcggcc ggctgcacca agctgtttc cgagaagatc accggcacca    7740
ggcgcgaccg cccggagctg gccaggatgc ttgaccacct acgccctggc gacgttgtga   7800
cagtgaccag gctagaccgc ctggcccgca gcacccgcga cctactggac attgccgagc   7860
gcatccagga ggccggcgcg ggcctgcgta gcctggcaga gccgtgggcc gacaccacca   7920
```

```
cgccggccgg ccgcatggtg ttgaccgtgt tcgccggcat tgccgagttc gagcgttccc    7980
taatcatcga ccgcacccgg agcgggcgcg aggccgccaa ggcccgaggc gtgaagtttg    8040
gcccccgccc taccctcacc ccggcacaga tcgcgcacgc ccgcgagctg atcgaccagg    8100
aaggccgcac cgtgaaagag gcggctgcac tgcttggcgt gcatcgctcg accctgtacc    8160
gcgcacttga gcgcagcgag gaagtgacgc ccaccgagcc caggcggcgc ggtgccttcc    8220
gtgaggacgc attgaccgag gccgacgccc tggcggccgc cgagaatgaa cgccaagagg    8280
aacaagcatg aaaccgcacc aggacgggca ggacgaaccg tttttcatta ccgaagagat    8340
cgaggcggag atgatcgcgg ccgggtacgt gttcgagccg cccgcgcacg tctcaaccgt    8400
gcggctgcat gaaatcctgg ccggtttgtc tgatgccaag ctggcggcct ggccggccag    8460
cttggccgct gaagaaaccg agcgccgccg tctaaaaagg tgatgtgtat ttgagtaaaa    8520
cagcttgcgt catgcggtcg ctgcgtatat gatgcgatga gtaaataaac aaatacgcaa    8580
ggggaacgca tgaaggttat cgctgtactt aaccagaaag gcgggtcagg caagacgacc    8640
atcgcaaccc atctagcccg cgccctgcaa ctcgccgggg ccgatgttct gttagtcgat    8700
tccgatcccc agggcagtgc ccgcgattgg gcggccgtgc gggaagatca accgctaacc    8760
gttgtcggca tcgaccgccc gacgattgac cgcgacgtga aggccatcgg ccggcgcgac    8820
ttcgtagtga tcgacggagc gccccaggcg gcggacttgg ctgtgtccgc gatcaaggca    8880
gccgacttcg tgctgattcc ggtgcagcca agcccttacg acatatgggc caccgccgac    8940
ctggtggagc tggttaagca gcgcattgag gtcacggatg aaggctaca agcggccttt    9000
gtcgtgtcgc gggcgatcaa aggcacgcgc atcggcggtg aggttgccga ggcgctggcc    9060
gggtacgagc tgcccattct tgagtcccgt atcacgcagc gcgtgagcta cccaggcact    9120
gccgccgccg gcacaaccgt tcttgaatca gaacccgagg cgacgctgc ccgcgaggtc    9180
caggcgctgg ccgctgaaat taaatcaaaa ctcatttgag ttaatgaggt aaagagaaaa    9240
tgagcaaaag cacaaacacg ctaagtgccg gccgtccgag cgcacgcagc agcaaggctg    9300
caacgttggc cagcctggca gacacgccag ccatgaagcg ggtcaacttt cagttgccgg    9360
cggaggatca caccaagctg aagatgtacg cggtacgcca aggcaagacc attaccgagc    9420
tgctatctga atacatcgcg cagctaccag agtaaatgag caaatgaata atgagtagat    9480
gaattttag cggctaaagg aggcggcatg gaaaatcaag aacaaccagg caccgacgcc    9540
gtggaatgcc ccatgtgtgg aggaacgggc ggttggccag gcgtaagcgg ctgggttgtc    9600
tgccggccct gcaatggcac tggaaccccc aagcccgagg aatcggcgtg acggtcgcaa    9660
accatccggc ccggtacaaa tcggcgcggc gctgggtgat gacctggtgg agaagttgaa    9720
ggccgcgcag gccgcccagc ggcaacgcat cgaggcagaa gcacgccccg gtgaatcgtg    9780
gcaagcggcc gctgatcgaa tccgcaaaga atcccggcaa ccgccggcag ccggtgcgcc    9840
gtcgattagg aagccgccca agggcgacga gcaaccagat ttttcgttc cgatgctcta    9900
tgacgtgggc acccgcgata gtcgcagcat catggacgtg gccgttttcc gtctgtcgaa    9960
gcgtgaccga cgagctggcg aggtgatccg ctacgagctt ccagacgggc acgtagaggt   10020
ttccgcaggg ccggccggca tggccagtgt gtgggattac gacctggtac tgatggcggt   10080
ttcccatcta accgaatcca tgaaccgata ccgggaaggg aagggagaca gcccggccg   10140
cgtgttccgt ccacacgttg cggacgtact caagttctgc cggcgagccg atggcggaaa   10200
gcagaaagac gacctggtag aaacctgcat tcggttaaac accacgcacg ttgccatgca   10260
```

```
gcgtacgaag aaggccaaga acggccgcct ggtgacggta tccgagggtg aagccttgat   10320
tagccgctac aagatcgtaa agagcgaaac cgggcggccg gagtacatcg agatcgagct   10380
agctgattgg atgtaccgcg agatcacaga aggcaagaac ccggacgtgc tgacggttca   10440
ccccgattac tttttgatcg atcccggcat cggccgtttt ctctaccgcc tggcacgccg   10500
cgccgcaggc aaggcagaag ccagatggtt gttcaagacg atctacgaac gcagtggcag   10560
cgccggagag ttcaagaagt tctgtttcac cgtgcgcaag ctgatcgggt caaatgacct   10620
gccggagtac gatttgaagg aggaggcggg gcaggctggc ccgatcctag tcatgcgcta   10680
ccgcaacctg atcgagggcg aagcatccgc cggttcctaa tgtacggagc agatgctagg   10740
gcaaattgcc ctagcagggg aaaaggtcg aaaggtctc tttcctgtgg atagcacgta    10800
cattgggaac ccaaagccgt acattgggaa ccggaacccg tacattggga acccaaagcc   10860
gtacattggg aaccggtcac acatgtaagt gactgatata aaagagaaaa aaggcgattt   10920
ttccgcctaa aactctttaa aacttattaa aactcttaaa acccgcctgg cctgtgcata   10980
actgtctggc cagcgcacag ccgaagagct gcaaaaagcg cctacccttc ggtcgctgcg   11040
ctccctacgc cccgccgctt cgcgtcggcc tatcgcggcc gctggccgct caaaaatggc   11100
tggcctacgg ccaggcaatc taccagggcg cggacaagcc gcgccgtcgc cactcgaccg   11160
ccggcgccca catcaaggca ccctgcctcg cgcgtttcgg tgatgacggt gaaaacctct   11220
gacacatgca gctcccggag acggtcacag cttgtctgta agcggatgcc gggagcagac   11280
aagcccgtca gggcgcgtca gcgggtgttg gcgggtgtcg gggcgcagcc atgacccagt   11340
cacgtagcga tagcggagtg tatactggct taactatgcg gcatcagagc agattgtact   11400
gagagtgcac catatgcggt gtgaaatacc gcacagatgc gtaaggagaa ataccgcat   11460 caggcgctct tccgcttcct cgctcactga ctcgctgcgc tcggtcgttc ggctgcggcg   11520
agcggtatca gctcactcaa aggcggtaat acgttatcc acagaatcag gggataacgc    11580
aggaaagaac atgtgagcaa aaggccagca aaaggccagg aaccgtaaaa aggccgcgtt   11640
gctggcgttt ttccataggc tccgcccccc tgacgagcat cacaaaaatc gacgctcaag   11700
tcagaggtgg cgaaacccga caggactata aagataccag gcgtttcccc ctggaagctc   11760
cctcgtgcgc tctcctgttc cgaccctgcc gcttaccgga tacctgtccg cctttctccc   11820
ttcgggaagc gtggcgcttt ctcatagctc acgctgtagg tatctcagtt cggtgtaggt   11880
cgttcgctcc aagctgggct gtgtgcacga accccccgtt cagcccgacc gctgcgcctt   11940
atccggtaac tatcgtcttg agtccaaccc ggtaagacac gacttatcgc cactggcagc   12000
agccactggt aacaggatta gcagagcgag gtatgtaggc ggtgctacag agttcttgaa   12060
gtggtggcct aactacggct acactagaag gacagtattt ggtatctgcg ctctgctgaa   12120
gccagttacc ttcggaaaaa gagttggtag ctcttgatcc ggcaaacaaa ccaccgctgg   12180
tagcggtggt ttttttgttt gcaagcagca gattacgcgc agaaaaaaag gatctcaaga   12240
agatccggaa aacgcaagcg caaagagaaa gcaggtagct tgcagtgggc ttacatggcg   12300
atagctagac tgggcggttt tatgacagc aagcgaaccg gaattgcc                12348
```

<210> SEQ ID NO 32
<211> LENGTH: 12366
<212> TYPE: DNA
<213> ORGANISM: Artificial
<220> FEATURE:
<223> OTHER INFORMATION: pTVE 501

<400> SEQUENCE: 32

```
agattcgaag ctcggtcccg tgggtgttct gtcgtctcgt tgtacaacga aatccattcc      60
cattccgcgc tcaagatggc ttcccctcgg cagttcatca gggctaaatc aatctagccg     120
acttgtccgg tgaaatgggc tgcactccaa cagaaacaat caaacaaaca tacacagcga     180
cttattcaca cgcgacaaat tacaacggta tatatcctgc cagtactcgg ccgtcgaccg     240
cggtaccccg gaattaagct tgcatgcctg caggcaattg gccgctgtac catgcatgat     300
ctggatttta gtactggatt ttggttttag gaattagaaa ttttattgat agaagtattt     360
tacaaataca aatacatact aagggtttct tatatgctca acacatgagc gaaaccctat     420
aggaacccta attcccttat ctgggaacta ctcacacatt attatggaga aaatagagag     480
agatagattt gtagagagag actggtgatt tcagcgtgtc caagcttgct agctcactct     540
ttgctatcca agacctgctt gaccggttca ctttgattaa tgtatagatt atactcttgg     600
atgtaacgga tgacagagtt tggaagaaga tattgaactg acattccacg tctgatgaaa     660
agccgcactt tcgtagagga aatatcattg taaataagtt gtttgataat aaggatattt     720
cttctgtgtt catacatgat atcatgggaa agcgagaagg acctaacatc agaaccagtc     780
cttttccacga tcaaacatcc ataattaccc aaaatatggt gcaggtctga atcagcccac     840
acatgaggct cgcccatgga ttcgataaga tcaccgcctg ccaataacat gattttacg      900
cccatttttt caccatctac agtcatgatt ccacctctct tgatatttat ttcatgattg     960
aaatggtcca agacttttgc tgtccttgta taacttgatt gtaaagattc ccaggcatca    1020
accattaacc aagatgatgt ccgctcgcat gctaattcgc acatgcggac acgatgataa    1080
gctgggcta accctcgctt tgatagtta tcacttactg gagaaaaata accaccaacc     1140
acttcaaaac gcgtttgctc attgatatca tctaaagcca tttcaaacat tctcaaatgt    1200
aggtatgtta tgggagaaaa tgatccacaa gcaacgatga tcagaggcag tttttcagga    1260
tcttgtaact ttttcgtcaa tctgtgtaca ggaaattcgt aatcttcaat agttctggct    1320
tgtcttacaa ttgtgtgagg aacttcttcc aaatcagcaa tttggctctt cagtacccccc   1380
aaattcccag tcatcgtaac atcctgtaga gtagcgtcaa ttccattcga ttgcccttca    1440
ctttcctcct ccgatgatac atcccgagat agtggctgga agtcactagt atttaatgga    1500
atatggtcca ttcggttgct tgagttggcg tttttttttcc ttgacgacag ggttttgtaa   1560
atgtcgagat tgaaaggagc atcgatcgaa gaattataat cagctaaaac atatggaact    1620
atgggtccag attttggcat cgtatgtgtt ggatctggcg gtggttgtag ttcttcatttt   1680
ggctgtggcg gtttaaaatc gggtgctttg gtaaccttgc gcttcttctt gggatccatg    1740
gttttggttt aataagaaga gaaagagtt cttttgttat ggctgaagta atagagaaat     1800
gagctcgagt cctctccaaa tgaaatgaac ttccttatat agaggaaggg tcttgcgaag    1860
gatagtggga ttgtgcgtca tcccttacgt cagtggagat atcacatcaa tccacttgct    1920
ttgaagacgt ggttggaacg tcttctttttt ccacgatgct cctcgtgggt gggggtccat   1980
ctttgggacc actgtcggca gaggcatctt gaacgatagc cttccttta tcgcaatgat     2040
ggcatttgta ggtgccacct tccttttcta ctgtcctttt gatgaagtga cagatagctg    2100
ggcaatggaa tccgaggagg tttcccgata ttaccctttg ttgaaaagtc tcaatagccc    2160
tttggtcttc tgagactgta tctttgatat tcttggagta gacgagagtg tcgtgctcca    2220
ccatgttgac gaagattttc ttcttgtcat tgagtcgtaa aagactctgt atgaactgtt    2280
cgccagtctt cacggcgagt tctgttagat cctcgatctg aattttgac tccatgtatg    2340
```

```
gtgcatatgg cgcgccatat gcccgggccc tgtacagcgg ccgcgttaac gcgtatactc    2400
tagagcgatc gcccgggccg gccatttaaa tgaattcgag ctcggtaccc aaacgcggcc    2460
gcaagctata acttcgtata gcatacatta tacgaagtta ttcgactcta gaggatccca    2520
attcccatgc atggagtcaa agattcaaat agaggacact tctcgaactc ggccgtcgaa    2580
ctcggccgtc gagtacatgg tcgataagaa aaggcaattt gtagatgtta attcccatct    2640
tgaaagaaat atagtttaaa tatttattga taaaataaca agtcaggtat tatagtccaa    2700
gcaaaaacat aaatttattg atgcaagttt aaattcagaa atatttcaat aactgattat    2760
atcagctggt acattgccgt agatgaaaga ctgagtgcga tattatgtgt aatacataaa    2820
ttgatgatat agctagctta gctcatcggg ggatcctaga cgcgtgagat cagatctcgg    2880
tgacgggcag gaccggacgg ggcggtaccg gcaggctgaa gtccagctgc cagaaaccca    2940
cgtcatgcca gttcccgtgc ttgaagccgg ccgcccgcag catgccgcgg ggggcatatc    3000
cgagcgcctc gtgcatgcgc acgctcgggt cgttgggcag cccgatgaca gcgaccacgc    3060
tcttgaagcc ctgtgcctcc agggacttca gcaggtgggt gtagagcgtg agcccagtc    3120 ccgtccgctg gtgcgggggg gagacgtaca cggtcgactc ggccgtccag tcgtaggcgt    3180
tgcgtgcctt ccaggggccc gcgtaggcga tgccggcgac ctcgccgtcc acctcggcga    3240
cgagccaggg atagcgctcc cgcagacgga cgaggtcgtc cgtccactcc tgcggttcct    3300
gcggctcggt acggaagttg accgtgcttg tctcgatgta gtggttgacg atggtgcaga    3360
ccgccggcat gtccgcctcg gtggcacggc ggatgtcggc cgggcgtcgt tctgggtcca    3420
ttgttcttct ttactctttg tgtgactgag gtttggtcta gtgctttggt catctatata    3480
taatgataac aacaatgaga acaagctttg gagtgatcgg agggtctagg atacatgaga    3540
ttcaagtgga ctaggatcta caccgttgga ttttgagtgt ggatatgtgt gaggttaatt    3600
ttacttggta acggccacaa aggcctaagg agaggtgttg agacccttat cggcttgaac    3660
cgctggaata atgccacgtg gaagataatt ccatgaatct tatcgttatc tatgagtgaa    3720
attgtgtgat ggtggagtgg tgcttgctca ttttacttgc ctggtggact tggccctttc    3780
cttatgggga atttatattt tacttactat agagctttca tacctttttt ttaccttgga    3840
tttagttaat atataatggt atgattcatg aataaaaatg ggaattttt gaatttgtac     3900 tgctaaatgc ataagattag gtgaaactgt ggaatatata tttttttcat ttaaaagcaa    3960
aatttgcctt ttactagaat tataaatata gaaaaatata taacattcaa ataaaaatga    4020
aaataagaac tttcaaaaaa cagaactatg tttaatgtgt aaagattagt cgcacatcaa    4080
gtcatctgtt acaatatgtt acaacaagtc ataagcccaa caaagttagc acgtctaaat    4140
aaactaaaga gtccacgaaa atattacaaa tcataagccc aacaaagtta ttgatcaaaa    4200
aaaaaaaacg cccaacaaag ctaaacaaag tccaaaaaaa acttctcaag tctccatctt    4260
cctttatgaa cattgaaaac tatacacaaa acaagtcaga taaatctctt tctgggcctg    4320
tcttcccaac ctcctacatc acttccctat cggattgaat gttttacttg tacctttcc     4380 gttgcaatga tattgatagt atgtttgtga aaactaatag ggttaacaat cgaagtcatg    4440
gaatatggat ttggtccaag attttccgag agctttctag tagaaagccc atcaccagaa    4500
atttactagt aaaataaatc accaattagg tttcttatta tgtgccaaat tcaatataat    4560
tatagaggat atttcaaatg aaaacgtatg aatgttatta gtaaatggtc aggtaagaca    4620
ttaaaaaaat cctacgtcag atattcaact ttaaaaattc gatcagtgtg gaattgtaca    4680
aaaatttggg atctactata tatatataat gctttacaac acttggattt tttttggag     4740
```

```
gctggaattt ttaatctaca tatttgtttt ggccatgcac caactcattg tttagtgtaa    4800
tactttgatt ttgtcaaata tatgtgttcg tgtatatttg tataagaatt tctttgacca    4860
tatacacaca cacatatata tatatatata tatattatat atcatgcact tttaattgaa    4920
aaataatat atatatatat agtgcatttt ttctaacaac catatatgtt gcgattgatc     4980
tgcaaaaata ctgctagagt aatgaaaaat aaatctatt gctgaaatta tctcagatgt     5040
taagattttc ttaaagtaaa ttctttcaaa ttttagctaa aagtcttgta ataactaaag    5100
aataatacac aatctcgacc acggaaaaaa aacacataat aaatttgaat ttcgaccgcg    5160
gtacccggaa ttgggttata attacctcag gtcgaggaat taattcggta cgtacctaat   5220
aacttcgtat agcatacatt atacgaagtt atatggatct cgaggcatta cggcattacg    5280
gcactcgcga gggtcccaat tcgagcatgg agccatttac aattgaatat atcctgccgc    5340
cgctgccgct ttgcacccgg tggagcttgc atgttggttt ctacgcagaa ctgagccggt    5400
taggcagata atttccattg agaactgagc catgtgcacc ttccccccaa cacggtgagc    5460
gacggggcaa cggagtgatc cacatgggac ttttaaacat catccgtcgg atggcgttgc    5520
gagagaagca gtcgatccgt gagatcagcc gacgcaccgg gcaggcgcgc aacacgatcg    5580
caaagtattt gaacgcaggt acaatcgagc cgacgttcac ggtaccgaa cgaccaagca     5640
agctagctta gtaaagccct cgctagattt taatgcggat gttgcgatta cttcgccaac    5700
tattgcgata acaagaaaaa gccagccttt catgatatat ctcccaattt gtgtagggct    5760
tattatgcac gcttaaaaat aataaaagca gacttgaccct gatagtttgg ctgtgagcaa   5820
ttatgtgctt agtgcatcta acgcttgagt taagccgcgc cgcgaagcgg cgtcggcttg    5880
aacgaattgt tagacattat ttgccgacta ccttggtgat ctcgcctttc acgtagtgga    5940
caaattcttc caactgatct gcgcgcgagg ccaagcgatc ttcttcttgt ccaagataag    6000
cctgtctagc ttcaagtatg acgggctgat actgggccgg caggcgctcc attgcccagt    6060
cggcagcgac atccttcggc gcgatttttgc cggttactgc gctgtaccaa atgcgggaca    6120
acgtaagcac tacatttcgc tcatcgccag cccagtcggg cggcgagttc catagcgtta    6180
aggtttcatt tagcgcctca aatagatcct gttcaggaac cggatcaaag agttcctccg    6240
ccgctggacc taccaaggca acgctatgtt ctcttgcttt tgtcagcaag atagccagat    6300
caatgtcgat cgtggctggc tcgaagatac ctgcaagaat gtcattgcgc tgccattctc    6360
caaattgcag ttcgcgctta gctggataac gccacggaat gatgtcgtcg tgcacaacaa    6420
tggtgacttc tacagcgcgg agaatctcgc tctctccagg ggaagccgaa gtttccaaaa    6480
ggtcgttgat caaagctcgc cgcgttgttt catcaagcct tacggtcacc gtaaccagca    6540
aatcaatatc actgtgtggc ttcaggccgc catccactgc ggagccgtac aaatgtacgg    6600
ccagcaacgt cggttcgaga tggcgctcga tgacgccaac tacctctgat agttgagtcg    6660
atacttcggc gatcaccgct tccctcatga tgtttaactt tgttttaggg cgactgccct    6720
gctgcgtaac atcgttgctg ctccataaca tcaaacatcg acccacggcg taacgcgctt    6780
gctgcttgga tgcccgaggc atagactgta ccccaaaaaa acagtcataa caagccatga    6840
aaaccgccac tgcgccgtta ccaccgctgc gttcggtcaa ggttctggac cagttgcgtg    6900
agcgcatacg ctacttgcat tacagcttac gaaccgaaca ggcttatgtc cactgggttc    6960
gtgccttcat ccgtttccac ggtgtgcgtc acccggcaac cttgggcagc agcgaagtcg    7020
aggcatttct gtcctggctg gcgaacgagc gcaaggtttc ggtctccacg catcgtcagg    7080
```

-continued

```
cattggcggc cttgctgttc ttctacggca agtgctgtgc acggatctgc cctggcttca   7140
ggagatcgga agacctcggc cgtccgggcg cttgccggtg gtgctgaccc cggatgaagt   7200
ctctagagct ctagagggtt cgcatcctcg gttttctgga aggcgagcat cgtttgttcg   7260
cccagcttct gtatggaacg ggcatgcgga tcagtgaggg tttgcaactg cgggtcaagg   7320
atctggattt cgatcacggc acgatcatcg tgcgggaggg caagggctcc aaggatcggg   7380
ccttgatgtt acccgagagc ttggcaccca gcctgcgcga gcaggatcg atccaacccc    7440
tccgctgcta tagtgcagtc ggcttctgac gttcagtgca gccgtcttct gaaaacgaca   7500
tgtcgcacaa gtcctaagtt acgcgacagg ctgccgccct gccctttcc tggcgttttc    7560
ttgtcgcgtg ttttagtcgc ataaagtaga atacttgcga ctagaaccgg agacattacg   7620
ccatgaacaa gagcgccgcc gctggcctgc tgggctatgc ccgcgtcagc accgacgacc   7680
aggacttgac caaccaacgg gccgaactgc acgcggccgg ctgcaccaag ctgttttccg   7740
agaagatcac cggcaccagg cgcgaccgcc cggagctggc caggatgctt gaccacctac   7800
gccctggcga cgttgtgaca gtgaccaggc tagaccgcct ggcccgcagc acccgcgacc   7860
tactggacat tgccgagcgc atccaggagg ccggcgcggg cctgcgtagc ctggcagagc   7920
cgtgggccga caccaccacg ccggccggcc gcatggtgtt gaccgtgttc gccggcattg   7980
ccgagttcga gcgttcccta atcatcgacc gcacccggag cgggcgcgag gccgccaagg   8040
cccgaggcgt gaagtttggc ccccgcccta ccctcacccc ggcacagatc gcgcacgccc   8100
gcgagctgat cgaccaggaa ggccgcaccg tgaaagaggc ggctgcactg cttggcgtgc   8160
atcgctcgac cctgtaccgc gcacttgagc gcagcgagga agtgacgccc accgaggcca   8220
ggcggcgcgg tgccttccgt gaggacgcat tgaccgaggc cgacgccctg gcggccgccg   8280
agaatgaacg ccaagaggaa caagcatgaa accgcaccag gacggccagg acgaaccgtt   8340
tttcattacc gaagagatcg aggcggagat gatcgcggcc gggtacgtgt tcgagccgcc   8400
cgcgcacgtc tcaaccgtgc ggctgcatga atcctggcc ggtttgtctg atgccaagct    8460
ggcggcctgg ccggccagct tggccgctga agaaaccgag cgccgccgtc taaaaggtg    8520
atgtgtattt gagtaaaaca gcttgcgtca tgcggtcgct gcgtatatga tgcgatgagt   8580
aaataaacaa atacgcaagg ggaacgcatg aaggttatcg ctgtacttaa ccagaaaggc   8640
gggtcaggca agacgaccat cgcaacccat ctagcccgcg ccctgcaact cgccggggcc   8700
gatgttctgt tagtcgattc cgatccccag ggcagtgccc gcgattgggc ggccgtgcgg   8760
gaagatcaac cgctaaccgt tgtcggcatc gaccgcccga cgattgaccg cgacgtgaag   8820
gccatcggcc ggcgcgactt cgtagtgatc gacggagcgc cccaggcggc ggacttggct   8880
gtgtccgcga tcaaggcagc cgacttcgtg ctgattccgg tgcagccaag cccttacgac   8940
atatgggcca ccgccgacct ggtggagctg gttaagcagc gcattgaggt cacggatgga   9000
aggctacaag cggcctttgt cgtgtcgcgg gcgatcaaag gcacgcgcat cggcggtgag   9060
gttgccgagg cgctggccgg gtacgagctg cccattcttg agtcccgtat cacgcagcgc   9120
gtgagctacc aggcactgc cgccgccggc acaaccgttc ttgaatcaga acccgagggc    9180
gacgctgccc gcgaggtcca ggcgctggcc gctgaaatta aatcaaaact catttgagtt   9240
aatgaggtaa agagaaaatg agcaaaagca caaacacgct aagtgccggc cgtccgagcg   9300
cacgcagcag caaggctgca acgttggcca gcctggcaga cacgccagcc atgaagcggg   9360
tcaactttca gttgccggcg gaggatcaca ccaagctgaa gatgtacgcg gtacgccaag   9420
gcaagaccat taccgagctg ctatctgaat acatcgcgca gctaccagag taaatgagca   9480
```

```
aatgaataaa tgagtagatg aattttagcg gctaaaggag gcggcatgga aaatcaagaa   9540
caaccaggca ccgacgccgt ggaatgcccc atgtgtggag gaacgggcgg ttggccaggc   9600
gtaagcggct gggttgtctg ccggccctgc aatggcactg gaaccccaa gcccgaggaa    9660 tcggcgtgac ggtcgcaaac catccggccc ggtacaaatc ggcgcggcgc tgggtgatga   9720
cctggtggag aagttgaagg ccgcgcaggc cgcccagcgg caacgcatcg aggcagaagc   9780
acgccccggt gaatcgtggc aagcggccgc tgatcgaatc cgcaaagaat cccggcaacc   9840
gccggcagcc ggtgcgccgt cgattaggaa gccgcccaag ggcgacgagc aaccagattt   9900
tttcgttccg atgctctatg acgtgggcac ccgcgatagt cgcagcatca tggacgtggc   9960
cgttttccgt ctgtcgaagc gtgaccgacg agctggcgag gtgatccgct acgagcttcc  10020
agacgggcac gtagaggttt ccgcagggcc ggccggcatg gccagtgtgt gggattacga  10080
cctggtactg atggcggttt ccatctaac cgaatccatg aaccgatacc gggaagggaa   10140
gggagacaag cccggccgcg tgttccgtcc acacgttgcg gacgtactca agttctgccg  10200
gcgagccgat ggcggaaagc agaaagacga cctggtagaa acctgcattc ggttaaacac  10260
cacgcacgtt gccatgcagc gtacgaagaa ggccaagaac ggccgcctgg tgacggtatc  10320
cgagggtgaa gccttgatta ccgctacaa gatcgtaaag agcgaaaccg ggcggccgga   10380
gtacatcgag atcgagctag ctgattggat gtaccgcgag atcacagaag gcaagaaccc  10440
ggacgtgctg acggttcacc ccgattactt tttgatcgat cccggcatcg gccgttttct  10500
ctaccgcctg gcacgccgcg ccgcaggcaa ggcagaagcc agatggttgt tcaagacgat  10560
ctacgaacgc agtggcagcg ccggagagtt caagaagttc tgtttcaccg tgcgcaagct  10620
gatcgggtca aatgacctgc cggagtacga tttgaaggag gaggcggggc aggctggccc  10680
gatcctagtc atgcgctacc gcaacctgat cgagggcgaa gcatccgccg gttcctaatg  10740 tacgagcag atgctagggc aaattgccct agcaggggaa aaaggtcgaa aaggtctctt   10800
tcctgtggat agcacgtaca ttgggaaccc aaagccgtac attgggaacc ggaacccgta  10860
cattgggaac ccaaagccgt acattgggaa ccggtcacac atgtaagtga ctgatataaa  10920
agagaaaaaa ggcgattttt ccgcctaaaa ctctttaaaa cttattaaaa ctcttaaaac  10980
ccgcctggcc tgtgcataac tgtctggcca gcgcacagcc gaagagctgc aaaaagcgcc  11040 taccettcgg tcgctgcgct ccctacgccc cgccgcttcg cgtcggccta tcgcggccgc  11100
tggccgctca aaaatggctg gcctacggcc aggcaatcta ccaggcgcg gacaagccgc   11160 gccgtcgcca ctcgaccgcc ggcgcccaca tcaaggcacc ctgcctcgcg cgtttcggtg  11220 atgacgcgtga aaacctctga cacatgcagc tcccggagac ggtcacagct tgtctgtaag  11280
cggatgccgg gagcagacaa gcccgtcagg gcgcgtcagc gggtgttggc gggtgtcggg  11340
gcgcagccat gacccagtca cgtagcgata gcggagtgta tactggctta actatgcggc  11400
atcagagcag attgtactga gagtgcacca tatgcggtgt gaaataccgc acagatgcgt  11460
aaggagaaaa taccgcatca ggcgctcttc cgcttcctcg ctcactgact cgctgcgctc  11520
ggtcgttcgg ctgcggcgag cggtatcagc tcactcaaag gcggtaatac ggttatccac  11580
agaatcaggg gataacgcag gaaagaacat gtgagcaaaa ggccagcaaa aggccaggaa  11640
ccgtaaaaag gccgcgttgc tggcgttttt ccataggctc cgcccccctg acgagcatca  11700
caaaaatcga cgctcaagtc agaggtggcg aaacccgaca ggactataaa gataccaggc  11760
gtttccccct ggaagctccc tcgtgcgctc tcctgttccg accctgccgc ttaccggata  11820
```

```
cctgtccgcc tttctccctt cgggaagcgt ggcgctttct catagctcac gctgtaggta   11880
tctcagttcg gtgtaggtcg ttcgctccaa gctgggctgt gtgcacgaac ccccgttca   11940 gcccgaccgc tgcgccttat ccggtaacta tcgtcttgag tccaacccgg taagacacga   12000
cttatcgcca ctggcagcag ccactggtaa caggattagc agagcgaggt atgtaggcgg   12060
tgctacagag ttcttgaagt ggtggcctaa ctacggctac actagaagga cagtatttgg   12120
tatctgcgct ctgctgaagc cagttacctt cggaaaaaga gttggtagct cttgatccgg   12180
caaacaaacc accgctggta gcggtggttt ttttgtttgc aagcagcaga ttacgcgcag   12240
aaaaaaagga tctcaagaag atccggaaaa cgcaagcgca agagaaagc aggtagcttg   12300 cagtgggctt acatggcgat agctagactg ggcggtttta tggacagcaa gcgaaccgga   12360
attgcc                                                              12366

<210> SEQ ID NO 33
<211> LENGTH: 13305
<212> TYPE: DNA
<213> ORGANISM: Artificial
<220> FEATURE:
<223> OTHER INFORMATION: pTVE502

<400> SEQUENCE: 33
agattcgaag ctcggtcccg tgggtgttct gtcgtctcgt tgtacaacga aatccattcc     60
cattccgcgc tcaagatggc ttcccctcgg cagttcatca gggctaaatc aatctagccg    120
acttgtccgg tgaaatgggc tgcactccaa cagaaacaat caaacaaaca tacacagcga    180
cttattcaca cgcgacaaat tacaacggta tatatcctgc cagtactcgg ccgtcgaccg    240
cggtaccccg gaattaagct tgcatgcctg caggcaattg gccgctgtac catgcatgat    300
ctggatttta gtactggatt ttggttttag gaattagaaa ttttattgat agaagtattt    360
tacaaataca aatacatact aagggtttct tatatgctca acacatgagc gaaaccctat    420
aggaacccta attcccttat ctgggaacta ctcacacatt attatggaga aaatagagag    480
agatagattt gtagagagag actggtgatt tcagcgtgtc caagcttgct agcctaatca    540
atagacataa tgtcaagcgt tgagccttta tgtgcttcac actgctcgac aacttcatca    600
atttttcttg aagcccatgg aaatcttggg ttgattaaga aaggacgtaa gtcaaatctg    660
ttgtcttctg gtgaatactg ttcagcatga taactaggag ttaaaacagt ttgcttgtgt    720
ctgttgatgg catagaagaa gaaaaatctt ttcacctttt cagatatttg acgaggtgtt    780
aactttgggg accattgatg aagaagtttt aagaacatag ataaggacc acattttca    840 acctttctta ggtaaccaaa cacgcccaat tcttcatacg tcatcccat atctatctca    900 tccgattgaa cgtaatcttt agtcataggt tctaattctg cagttggtgt agcgtttaaa    960
aagtcattca agattggcat gttatattgt tttgatgcgt aggcaatgaa tcttttcaag   1020 tcagttttg aaatacccc aatagggttg atatctgcgg aggagcagtc atattttgtt   1080
agatacccac gtaagcactc atcaacattt gcgctaccaa gtactaacaa tccacccgag   1140
tttgggatac cacgaaccca cggcaacagt tgcgcaaaaa gataagaaag accattctt   1200 agacgcgcct ggatgttttg taaagccaag ttctcgattt gagatccccc aaatattttg   1260
tatattggtt ttttgccagt ggctacttcg aataaggaca ccacactgga taccaatgag   1320 tccatctta aatccacgtg gtaagatcca attgcattgg aaaggtcctt tgctctgttt   1380
cttgtctcct tggatgaatt ttccgtaccc atgaaacagg agtgaaatat ttttgaggct   1440
agatcctgtg gactgtctgg aatccaatca tcgccgctac gtgttatctt acgaacgtct   1500
```

-continued

```
ttgataactt gctcatttcc attttgagca gcgtcggtca ctaaacggca catagagtgg    1560
acaatcattg cagttgcaca agagtcaatg cccccagata agggaaggaa aaaccctgtt    1620
ccgttacaac gtcttaaata atcccacatc cagcaagcag gtcccagtgc aatttcttcc    1680
tcaggagagt gatagaaagg ctcgcggact tttgttggac acactgtagg atcaaatctg    1740
gaggtcatta aagccaattc tacaggaata tcaatacgct tgaactttat ttctgccaag    1800
gaggcttgta ggccacgaga catgacagct gcacgataac tcctcacctc ttctaggtcc    1860
acagtagcag taactacttc cacatcatct agcgaaaatt gtgaaccttg gctacaatt    1920 gtaccattga tggcaattag tgcacagcca tcataatata atctgtcacc atcacaacct    1980
ctttgatttg catacaagta aacaccacca caacgtttag tggcatttaa aattaggtct    2040
aaccttttat ttaacttacg cagttcatga tgagaaccag atgagtttgt catgatttcc    2100
acaccatcta aagacatggc gatgtggggg gattgaggtg taaacaattc ttcacaagtt    2160
tctgtaccaa tgcatgtatc caatgaattt atcacagcgt ccccaaatgg cacaagtctc    2220
tggccggtaa ctttctgaat ctcaggtgga aggataaagt cctccaccac gccaggtttc    2280
atccaaggtg tgaaaaatct catttcccta tagttaccat cattagctaa ccaaatctta    2340
ggtcttatga acaatatctc accatccaag gataacaaac gacaattata acgaacattc    2400
ttgtgtagaa cgggcatacc aatgtcaagt attaatccat gggtttcttt attcttaatg    2460
atttgagcat acatttccca tgaatgaagg caaacgtcat tttctaaaaa atgatctaaa    2520
catccgtagc cagttatttc cagttctggg ccgacacgta acctggcacc cctctctttg    2580
gcaatcttaa tggactgtag gatacggtct ctattacctt caaaatctag ggcccattga    2640
ttcaagttgc atgtagctaa agtgataaga tgtgccatgg ttttggttta ataagaagag    2700
aaaagagttc ttttgttatg gctgaagtaa tagagaaatg agctcgagtc ctctcccaaat   2760 gaaatgaact tccttatata gaggaagggg cttgcgaagg atagtgggat tgtgcgtcat    2820
cccttacgtc agtggagata tcacatcaat ccacttgctt tgaagacgtg gttggaacgt    2880 cttcttttc cacgatgctc ctcgtgggtg ggggtccatc tttgggacca ctgtcggcag     2940
aggcatcttg aacgatagcc tttcctttat cgcaatgatg gcatttgtag gtgccacctt    3000
ccttttctac tgtccttttg atgaagtgac agatagctgg gcaatggaat ccgaggaggt    3060
ttcccgatat tacccttgt tgaaaagtct caatagccct ttggtcttct gagactgtat     3120
ctttgatatt cttggagtag acgagagtgt cgtgctccac catgttgacg aagattttct    3180
tcttgtcatt gagtcgtaaa agactctgta tgaactgttc gccagtcttc acggcgagtt    3240
ctgttagatc ctcgatctga attttttgact ccatgtatgg tgcatatggc gcgccatatg   3300
cccgggccct gtacagcggc gcgttaacg cgtatactct agagcgatcg cccgggccgg     3360
ccatttaaat gaattcgagc tcggtaccca aacgcggccg caagctataa cttcgtatag    3420
catacattat acgaagttat tcgactctag aggatcccaa ttcccatgca tggagtcaaa    3480
gattcaaata gaggacactt ctcgaactcg gccgtcgaac tcggccgtcg agtacatggt    3540
cgataagaaa aggcaatttg tagatgttaa ttcccatctt gaaagaaata tagtttaaat    3600
atttattgat aaaataacaa gtcaggtatt atagtccaag caaaaacata aatttattga    3660
tgcaagttta aattcagaaa tatttcaata actgattata tcagctggta cattgccgta    3720
gatgaaagac tgagtgcgat attatgtgta atacataaat tgatgatata gctagcttag    3780
ctcatcgggg gatcctagac gcgtgagatc agatctcggt gacgggcagg accggacggg    3840
```

```
gcggtaccgg caggctgaag tccagctgcc agaaacccac gtcatgccag ttcccgtgct   3900
tgaagccggc cgcccgcagc atgccgcggg gggcatatcc gagcgcctcg tgcatgcgca   3960
cgctcgggtc gttgggcagc ccgatgacag cgaccacgct cttgaagccc tgtgcctcca   4020
gggacttcag caggtgggtg tagagcgtgg agcccagtcc cgtccgctgg tggcgggggg   4080
agacgtacac ggtcgactcg gccgtccagt cgtaggcgtt gcgtgccttc caggggcccg   4140
cgtaggcgat gccggcgacc tcgccgtcca cctcggcgac gagccaggga tagcgctccc   4200
gcagacggac gaggtcgtcc gtccactcct gcggttcctg cggctcggta cggaagttga   4260
ccgtgcttgt ctcgatgtag tggttgacga tggtgcagac cgccggcatg tccgcctcgg   4320
tggcacggcg gatgtcggcc gggcgtcgtt ctgggtccat tgttcttctt tactctttgt   4380
gtgactgagg tttggtctag tgctttggtc atctatatat aatgataaca acaatgagaa   4440
caagctttgg agtgatcgga gggtctagga tacatgagat tcaagtggac taggatctac   4500
accgttggat tttgagtgtg gatatgtgtg aggttaattt tacttggtaa cggccacaaa   4560
ggcctaagga gaggtgttga gacccttatc ggcttgaacc gctggaataa tgccacgtgg   4620
aagataattc catgaatctt atcgttatct atgagtgaaa ttgtgtgatg gtggagtggt   4680
gcttgctcat tttacttgcc tggtggactt ggcccttttcc ttatggggaa tttatatttt   4740
acttactata gagctttcat acctttttttt taccttggat ttagttaata tataatggta   4800
tgattcatga ataaaaatgg gaaattttttg aatttgtact gctaaatgca taagattagg   4860
tgaaactgtg gaatatatat ttttttcatt taaaagcaaa atttgccttt tactagaatt   4920
ataaatatag aaaaatatat aacattcaaa taaaaatgaa aataagaact ttcaaaaaac   4980
agaactgtgt ttaatgtgta aagattagtc gcacatcaag tcatctgtta caatatgtta   5040
caacaagtca taagcccaac aaagttagca cgtctaaata aactaaagag tccacgaaaa   5100
tattacaaat cataagccca acaaagttat tgatcaaaaa aaaaaaacgc ccaacaaagc   5160
taaacaaagt ccaaaaaaaa cttctcaagt ctccatcttc ctttatgaac attgaaaact   5220
atacacaaaa caagtcagat aaatctcttt ctgggcctgt cttcccaacc tcctacatca   5280
cttccctatc ggattgaatg ttttacttgt accttttccg ttgcaatgat attgatagta   5340
tgtttgtgaa aactaatagg gttaacaatc gaagtcatgg aatatggatt tggtccaaga   5400
ttttccgaga gctttctagt agaaagccca tcaccagaaa tttactagta aaataaatca   5460
ccaattaggt ttcttattat gtgccaaatt caatataatt atagaggata tttcaaatga   5520
aaacgtatga atgttattag taaatggtca ggtaagacat taaaaaaatc ctacgtcaga   5580
tattcaactt taaaaattcg atcagtgtgg aattgtacaa aaatttggga tctactatat   5640
atatataatg ctttacaaca cttggatttt tttttggagg ctggaatttt taatctcact   5700
atttgttttg gccatgcacc aactcattgt ttagtgtaat actttgattt tgtcaaatat   5760
atgtgttcgt gtatatttgt ataagaattt ctttgaccat atacacacac acatatatat   5820
atatatatat atattatata tcatgcactt ttaattgaaa aaataatata tatatatata   5880
gtgcattttt tctaacaacc atatatgttg cgattgatct gcaaaaatac tgctagagta   5940
atgaaaaata taatctattg ctgaaattat ctcagatgtt aagattttct taaagtaaat   6000
tctttcaaat tttagctaaa agtcttgtaa taactaaaga ataatacaca atctcgacca   6060
cggaaaaaaa acacataata aatttgaatt tcgaccgcgg tacccggaat tgggttataa   6120
ttacctcagg tcgaggaatt aattcggtac gtacctaata acttcgtata gcatacatta   6180
tacgaagtta tatggatctc gaggcattac ggcattacgg cactcgcgag ggtcccaatt   6240
```

```
cgagcatgga gccatttaca attgaatata tcctgccgcc gctgccgctt tgcacccggt    6300
ggagcttgca tgttggtttc tacgcagaac tgagccggtt aggcagataa tttccattga    6360
gaactgagcc atgtgcacct tcccccaac  acggtgagcg acggggcaac ggagtgatcc    6420
acatgggact tttaaacatc atccgtcgga tggcgttgcg agagaagcag tcgatccgtg    6480
agatcagccg acgcaccggg caggcgcgca acacgatcgc aaagtatttg aacgcaggta    6540
caatcgagcc gacgttcacg gtaccggaac gaccaagcaa gctagcttag taaagccctc    6600
gctagatttt aatgcggatg ttgcgattac ttcgccaact attgcgataa caagaaaaag    6660
ccagcctttc atgatatatc tcccaatttg tgtagggctt attatgcacg cttaaaaata    6720
ataaaagcag acttgacctg atagtttggc tgtgagcaat tatgtgctta gtgcatctaa    6780
cgcttgagtt aagccgcgcc gcgaagcggc gtcggcttga acgaattgtt agacattatt    6840
tgccgactac cttggtgatc tcgcctttca cgtagtggac aaattcttcc aactgatctg    6900
cgcgcgaggc caagcgatct tcttcttgtc aagataagc  ctgtctagct tcaagtatga    6960
cgggctgata ctgggccggc aggcgctcca ttgcccagtc ggcagcgaca tccttcgggcg   7020 cgattttgcc ggttactgcg ctgtaccaaa tgcgggacaa cgtaagcact acatttcgct    7080
catcgccagc ccagtcgggc ggcgagttcc atagcgttaa ggtttcattt agcgcctcaa    7140
atagatcctg ttcaggaacc ggatcaaaga gttcctccgc cgctggacct accaaggcaa    7200
cgctatgttc tcttgctttt gtcagcaaga tagccagatc aatgtcgatc gtggctggct    7260
cgaagatacc tgcaagaatg tcattgcgct gccattctcc aaattgcagt tcgcgcttag    7320
ctggataacg ccacggaatg atgtcgtcgt gcacaacaat ggtgacttct acagcgcgga    7380
gaatctcgct ctctccaggg gaagccgaag tttccaaaag gtcgttgatc aaagctcgcc    7440
gcgttgtttc atcaagcctt acggtcaccg taaccagcaa atcaatatca ctgtgtggct    7500
tcaggccgcc atccactgcg gagccgtaca aatgtacggc cagcaacgtc ggttcgagat    7560
ggcgctcgat gacgccaact acctctgata gttgagtcga tacttcggcg atcaccgctt    7620
ccctcatgat gtttaacttt gttttagggc gactgccctg ctgcgtaaca tcgttgctgc    7680
tccataacat caaacatcga cccacggcgt aacgcgcttg ctgcttggat gcccgaggca    7740
tagactgtac cccaaaaaaa cagtcataac aagccatgaa aaccgccact cgcgccgttac   7800 caccgctgcg ttcggtcaag gttctggacc agttgcgtga gcgcatacgc tacttgcatt    7860
acagcttacg aaccgaacag gcttatgtcc actgggttcg tgccttcatc cgtttccacg    7920
gtgtgcgtca cccggcaacc ttgggcagca gcgaagtcga ggcatttctg tcctggctgg    7980
cgaacgagcg caaggtttcg gtctccacgc atcgtcaggc attggcggcc ttgctgttct    8040
tctacggcaa gtgctgtgca cggatctgcc ctggcttcag gagatcggaa gacctcggcc    8100 gtccgggcg  ttgccggtgg tgctgacccc ggatgaagtc tctagagctc tagagggttc    8160
gcatcctcgg ttttctggaa ggcgagcatc gtttgttcgc ccagcttctg tatggaacgg    8220
gcatgcggat cagtgagggt ttgcaactgc gggtcaagga tctggatttc gatcacggca    8280
cgatcatcgt gcgggagggc aagggctcca aggatcgggc cttgatgtta cccgagagct    8340
tggcacccag cctgcgcgag cagggatcga tccaacccct ccgctgctat agtgcagtcg    8400
gcttctgacg ttcagtgcag ccgtcttctg aaaacgacat gtcgcacaag tcctaagtta    8460
cgcgacaggc tgccgccctg ccctttttcct ggcgttttct tgtcgcgtgt tttagtcgca    8520
taaagtagaa tacttgcgac tagaaccgga gacattacgc catgaacaag agcgccgccg    8580
```

```
ctggcctgct gggctatgcc cgcgtcagca ccgacgacca ggacttgacc aaccaacggg    8640
ccgaactgca cgcggccggc tgcaccaagc tgttttccga aagatcacc ggcaccaggc     8700 gcgaccgccc ggagctggcc aggatgcttg accacctacg ccctggcgac gttgtgacag    8760
tgaccaggct agaccgcctg gcccgcagca cccgcgacct actggacatt gccgagcgca    8820
tccaggaggc cggcgcgggc ctgcgtagcc tggcagagcc gtgggccgac accaccacgc    8880
cggccggccg catggtgttg accgtgttcg ccggcattgc cgagttcgag cgttccctaa    8940
tcatcgaccg cacccggagc gggcgcgagg ccgccaaggc ccgaggcgtg aagtttggcc    9000
cccgccctac cctcaccccg gcacagatcg cgcacgcccg cgagctgatc gaccaggaag    9060
gccgcaccgt gaaagaggcg gctgcactgc ttggcgtgca tcgctcgacc ctgtaccgcg    9120
cacttgagcg cagcgaggaa gtgacgccca ccgaggccag gcggcgcggt gccttccgtg    9180
aggacgcatt gaccgaggcc gacgccctgg cggccgccga gaatgaacgc caagaggaac    9240
aagcatgaaa ccgcaccagg acggccagga cgaaccgttt ttcattaccg aagagatcga    9300
ggcggagatg atcgcggccg ggtacgtgtt cgagccgccc gcgcacgtct caaccgtgcg    9360
gctgcatgaa atcctggccg gtttgtctga tgccaagctg gcggcctggc cggccagctt    9420
ggccgctgaa gaaaccgagc gccgccgtct aaaaaggtga tgtgtatttg agtaaaacag    9480
cttgcgtcat gcggtcgctg cgtatatgat gcgatgagta aataaacaaa tacgcaaggg    9540
gaacgcatga aggttatcgc tgtacttaac cagaaaggcg ggtcaggcaa gacgaccatc    9600
gcaacccatc tagcccgcgc cctgcaactc gccggggccg atgttctgtt agtcgattcc    9660
gatccccagg gcagtgcccg cgattgggcg gccgtgcggg aagatcaacc gctaaccgtt    9720
gtcggcatcg accgcccgac gattgaccgc gacgtgaagg ccatcggccg gcgcgacttc    9780
gtagtgatcg acggagcgcc ccaggcggcg gacttggctg tgtccgcgat caaggcagcc    9840
gacttcgtgc tgattccggt gcagccaagc ccttacgaca tatgggccac cgccgacctg    9900
gtggagctgg ttaagcagcg cattgaggtc acggatggaa ggctacaagc ggcctttgtc    9960
gtgtcgcggg cgatcaaagg cacgcgcatc ggcggtgagg ttgccgaggc gctgccgggg    10020
tacgagctgc ccattcttga gtcccgtatc acgcagcgcg tgagctaccc aggcactgcc    10080
gccgccggca caaccgttct tgaatcagaa cccgagggcg acgctgcccg cgaggtccag    10140
gcgctggccg ctgaaattaa atcaaaactc atttgagtta atgaggtaaa gagaaaatga    10200
gcaaaagcac aaaacacgcta agtgccggcc gtccgagcgc acgcagcagc aaggctgcaa    10260
cgttggccag cctggcagac acgccagcca tgaagcgggt caactttcag ttgccggcgg    10320
aggatcacac caagctgaag atgtacgcgg tacgccaagg caagaccatt accgagctgc    10380
tatctgaata catcgcgcag ctaccagagt aaatgagcaa atgaataaat gagtagatga    10440
attttagcgg ctaaaggagg cggcatggaa atcaagaac aaccaggcac cgacgccgtg    10500
gaatgcccca tgtgtggagg aacgggcggt tggccaggcg taagcggctg ggttgtctgc    10560
cggccctgca atggcactgg aaccccaag cccgaggaat cggcgtgacg gtcgcaaacc    10620
atccggcccg gtacaaatcg gcgcggcgct gggtgatgac ctggtggaga gttgaaggc     10680 cgcgcaggcc gcccagcggc aacgcatcga ggcagaagca cgccccggtg aatcgtggca    10740
agcggccgct gatcgaatcc gcaaagaatc ccggcaaccg ccggcagccg gtgcgccgtc    10800
gattaggaag ccgcccaagg cgacgagca accagatttt ttcgttccga tgctctatga    10860
cgtgggcacc cgcgatagtc gcagcatcat ggacgtggcc gttttccgtc tgtcgaagcg    10920
tgaccgacga gctggcgagg tgatccgcta cgagcttcca gacgggcacg tagaggtttc    10980
```

```
cgcagggccg gccggcatgg ccagtgtgtg ggattacgac ctggtactga tggcggtttc   11040
ccatctaacc gaatccatga accgataccg ggaagggaag ggagacaagc ccggccgcgt   11100
gttccgtcca cacgttgcgg acgtactcaa gttctgccgg cgagccgatg gcggaaagca   11160
gaaagacgac ctggtagaaa cctgcattcg gttaaacacc acgcacgttg ccatgcagcg   11220
tacgaagaag gccaagaacg gccgcctggt gacggtatcc gagggtgaag ccttgattag   11280
ccgctacaag atcgtaaaga gcgaaaccgg gcggccggag tacatcgaga tcgagctagc   11340
tgattggatg taccgcgaga tcacagaagg caagaacccg gacgtgctga cggttcaccc   11400
cgattacttt ttgatcgatc ccggcatcgg ccgttttctc taccgcctgg cacgccgcgc   11460
cgcaggcaag gcagaagcca gatggttgtt caagacgatc tacgaacgca gtggcagcgc   11520
cggagagttc aagaagttct gtttcaccgt gcgcaagctg atcgggtcaa atgacctgcc   11580
ggagtacgat ttgaaggagg aggcggggca ggctggcccg atcctagtca tgcgctaccg   11640
caacctgatc gagggcgaag catccgccgg ttcctaatgt acggagcaga tgctagggca   11700
aattgcccta gcaggggaaa aaggtcgaaa aggtctcttt cctgtggata gcacgtacat   11760
tgggaaccca aagccgtaca ttgggaaccg gaacccgtac attgggaacc caaagccgta   11820
cattgggaac cggtcacaca tgtaagtgac tgatataaaa gagaaaaaag gcgattttc    11880 cgcctaaaac tctttaaaac ttattaaaac tcttaaaacc cgcctggcct gtgcataact   11940
gtctggccag cgcacagccg aagagctgca aaaagcgcct acccttcggt cgctgcgctc   12000
cctacgcccc gccgcttcgc gtcggcctat cgcggccgct ggccgctcaa aaatggctgg   12060
cctacggcca ggcaatctac cagggcgcgg acaagccgcg ccgtcgccac tcgaccgccg   12120
gcgcccacat caaggcaccc tgcctcgcgc gtttcggtga tgacggtgaa aacctctgac   12180
acatgcagct cccggagacg gtcacagctt gtctgtaagc ggatgccggg agcagacaag   12240
cccgtcaggg cgcgtcagcg ggtgttggcg ggtgtcgggg cgcagccatg acccagtcac   12300
gtagcgatag cggagtgtat actggcttaa ctatgcggca tcagagcaga ttgtactgag   12360
agtgcaccat atgcggtgtg aaataccgca cagatgcgta aggagaaaat accgcatcag   12420
gcgctcttcc gcttcctcgc tcactgactc gctgcgctcg gtcgttcggc tgcggcgagc   12480
ggtatcagct cactcaaagg cggtaatacg gttatccaca gaatcagggg ataacgcagg   12540
aaagaacatg tgagcaaaag gccagcaaaa ggccaggaac cgtaaaaagg ccgcgttgct   12600
ggcgtttttc cataggctcc gcccccctga cgagcatcac aaaaatcgac gctcaagtca   12660
gaggtggcga aacccgacag gactataaag ataccaggcg tttccccctg gaagctccct   12720
cgtgcgctct cctgttccga ccctgccgct taccggatac ctgtccgcct ttctcccttc   12780
gggaagcgtg gcgctttctc atagctcacg ctgtaggtat ctcagttcgg tgtaggtcgt   12840
tcgctccaag ctgggctgtg tgcacgaacc ccccgttcag cccgaccgct gcgccttatc   12900
cggtaactat cgtcttgagt ccaacccggt aagacacgac ttatcgccac tggcagcagc   12960
cactggtaac aggattagca gagcgaggta tgtaggcggt gctacagagt tcttgaagtg   13020
gtggcctaac tacggctaca ctagaaggac agtatttggt atctgcgctc tgctgaagcc   13080
agttaccttc ggaaaaagag ttggtagctc ttgatccggc aaacaaacca ccgctggtag   13140
cggtggtttt tttgtttgca agcagcagat tacgcgcaga aaaaaaggat ctcaagaaga   13200
tccggaaaac gcaagcgcaa agagaaagca ggtagcttgc agtgggctta catggcgata   13260
gctagactgg gcggttttat ggacagcaag cgaaccggaa ttgcc                   13305
```

<210> SEQ ID NO 34
<211> LENGTH: 13326
<212> TYPE: DNA
<213> ORGANISM: Artificial
<220> FEATURE:
<223> OTHER INFORMATION: pTVE503

<400> SEQUENCE: 34

| | | | | | |
|---|---|---|---|---|---|
| agattcgaag | ctcggtcccg | tgggtgttct | gtcgtctcgt | tgtacaacga | aatccattcc | 60 |
| cattccgcgc | tcaagatggc | ttcccctcgg | cagttcatca | gggctaaatc | aatctagccg | 120 |
| acttgtccgg | tgaaatgggc | tgcactccaa | cagaaacaat | caaacaaaca | tacacagcga | 180 |
| cttattcaca | cgcgacaaat | tacaacggta | tatatcctgc | cagtactcgg | ccgtcgaccg | 240 |
| cggtaccccg | gaattaagct | tgcatgcctg | caggcaattg | gccgctgtac | catgcatgat | 300 |
| ctggatttta | gtactggatt | ttggttttag | gaattagaaa | ttttattgat | agaagtattt | 360 |
| tacaaataca | aatacatact | aagggtttct | tatatgctca | acacatgagc | gaaaccctat | 420 |
| aggaaccta | attcccttat | ctgggaacta | ctcacacatt | attatggaga | aaatagagag | 480 |
| agatagattt | gtagagagag | actggtgatt | tcagcgtgtc | caagcttgct | agcctaatca | 540 |
| atagacataa | tgtcaagcgt | tgagccttta | tgtgcttcac | actgctcgac | aacttcatca | 600 |
| atttttcttg | aagcccatgg | aaatcttggg | ttgattaaga | aaggacgtaa | gtcaaatctg | 660 |
| ttgtcttctg | gtgaatactg | ttcagcatga | taactaggag | ttaaaacagt | tgcttgtgt | 720 |
| ctgttgatgg | catagaagaa | gaaaaatctt | ttcacctttt | cagatatttg | acgaggtgtt | 780 |
| aactttgggg | accattgatg | aagaagtttt | aagaacatag | aataaggacc | acattttca | 840 |
| acctttctta | ggtaaccaaa | cacgcccaat | tcttcatacg | tcatccccat | atctatctca | 900 |
| tccgattgaa | cgtaatcttt | agtcataggt | tctaattctg | cagttggtgt | agcgtttaaa | 960 |
| aagtcattca | agattggcat | gttatattgt | tttgatgcgt | aggcaatgaa | tcttttcaag | 1020 |
| tcagttttg | aaatacccc | aataggggttg | atatctgcgg | aggagcagtc | atattttgtt | 1080 |
| agatacccac | gtaagcactc | atcaacattt | gcgctaccaa | gtactaacaa | tccacccgag | 1140 |
| tttgggatac | cacgaaccca | cggcaacagt | tgcgcaaaaa | gataagaaag | aaccattctt | 1200 |
| agacgcgcct | ggatgttttg | taaagccaag | ttctcgattt | gagatccccc | aaatattttg | 1260 |
| tatattggtt | ttttgccagt | ggctacttcg | aataaggaca | ccacactgga | taccaatgag | 1320 |
| tccatcttta | aatccacgtg | gtaagatcca | attgcattgg | aaaggtcctt | tgctctgttt | 1380 |
| cttgtctcct | tggatgaatt | ttccgtaccc | atgaaacagg | agtgaaatat | ttttgaggct | 1440 |
| agatcctgtg | gactgtctgg | aatccaatca | tcgccgctac | gtgttatctt | acgaacgtct | 1500 |
| ttgataactt | gctcatttcc | attttgagca | gcgtcggtca | ctaaacggca | catagagtgg | 1560 |
| acaatcattg | cagttgcaca | agagtcaatg | ccccagata | agggaaggaa | aaaccctgtt | 1620 |
| ccgttacaac | gtcttaaata | atcccacatc | cagcaagcag | gtcccagtgc | aatttcttcc | 1680 |
| tcaggagagt | gatagaaagg | ctcgcggact | tttgttggac | acactgtagg | atcaaatctg | 1740 |
| gaggtcatta | aagccaattc | tacaggaata | tcaatacgct | tgaactttat | ttctgccaag | 1800 |
| gaggcttgta | ggccacgaga | catgacagct | gcacgataac | tcctcacctc | ttctaggtcc | 1860 |
| acagtagcag | taactacttc | cacatcatct | agcgaaaatt | gtgaacctg | ggctacaatt | 1920 |
| gtaccattga | tggcaattag | tgcacagcca | tcataatata | atctgtcacc | atcacaacct | 1980 |
| ctttgatttg | catacaagta | aacaccacca | caacgtttag | tggcatttaa | aattaggtct | 2040 |
| aacctttat | ttaacttacg | cagttcatga | tgagaaccag | atgagtttgt | catgatttcc | 2100 |

```
acaccatcta aagacatggc gatgtggggg gattgaggtg taaacaattc ttcacaagtt    2160
tctgtaccaa tgcatgtatc caatgaattt atcacagcgt ccccaaatgg cacaagtctc    2220
tggccggtaa ctttctgaat ctcaggtgga aggataaagt cctccaccac gccaggtttc    2280
atccaaggtg tgaaaaatct catttcccta tagttaccat cattagctaa ccaaatctta    2340
ggtcttatga acaatatctc accatccaag gataacaaac gacaattata acgaacattc    2400
ttgtgtagaa cgggcatacc aatgtcaagt attaatccat gggtttcttt attcttaatg    2460
atttgagcat acatttccca tgaatgaagg caaacgtcat tttctaaaaa atgatctaaa    2520
catccgtagc cagttatttc cagttctggg ccgacacgta acctggcacc cctctctttg    2580
gcaatcttaa tggactgtag gatacggtct ctattacctt caaaatctag gcccattga     2640 ttcaagttgc atgtagctaa agtgataaga accttgcgct tcttcttggg atgtgccatg    2700
gttttggttt aataagaaga gaaaagagtt cttttgttat ggctgaagta atagagaaat    2760
gagctcgagt cctctccaaa tgaaatgaac ttccttatat agaggaaggg tcttgcgaag    2820
gatagtggga ttgtgcgtca tcccttacgt cagtggagat atcacatcaa tccacttgct    2880
ttgaagacgt ggttggaacg tcttcttttt ccacgatgct cctcgtgggt gggggtccat    2940 cttttgggacc actgtcggca gaggcatctt gaacgatagc cttccttta tcgcaatgat    3000 ggcatttgta ggtgccacct tccttttcta ctgtcctttt gatgaagtga cagatagctg    3060
ggcaatggaa tccgaggagg tttcccgata ttacccttg ttgaaaagtc tcaatagccc     3120
tttggtcttc tgagactgta tctttgatat tcttggagta gacgagagtg tcgtgctcca    3180
ccatgttgac gaagattttc ttcttgtcat tgagtcgtaa aagactctgt atgaactgtt    3240
cgccagtctt cacggcgagt tctgttagat cctcgatctg aattttgac tccatgtatg     3300 gtgcatatgg cgcgccatat gcccgggccc tgtacagcgg ccgcgttaac gcgtatactc    3360
tagagcgatc gcccgggccg gccatttaaa tgaattcgag ctcggtaccc aaacgcggcc    3420
gcaagctata acttcgtata gcatacatta tacgaagtta ttcgactcta gaggatccca    3480
attcccatgc atggagtcaa agattcaaat agaggacact tctcgaactc ggccgtcgaa    3540
ctcggccgtc gagtacatgg tcgataagaa aaggcaattt gtagatgtta ttcccatct    3600 tgaaagaaat atagtttaaa tatttattga taaaataaca agtcaggtat tatagtccaa    3660
gcaaaaacat aaatttattg atgcaagttt aaattcagaa atatttcaat aactgattat    3720
atcagctggt acattgccgt agatgaaaga ctgagtgcga tattatgtgt aatacataaa    3780
ttgatgatat agctagctta gctcatcggg ggatcctaga cgcgtgagat cagatctcgg    3840
tgacgggcag gaccggacgg ggcggtaccg gcaggctgaa gtccagctgc cagaaaccca    3900
cgtcatgcca gttcccgtgc ttgaagccgg ccgcccgcag catgccgcgg ggggcatatc    3960
cgagcgcctc gtgcatgcgc acgctcgggt cgttgggcag cccgatgaca gcgaccacgc    4020
tcttgaagcc ctgtgcctcc agggacttca gcaggtgggt gtagagcgtg agcccagtc     4080 ccgtccgctg gtggcggggg gagacgtaca cggtcgactc ggccgtccag tcgtaggcgt    4140
tgcgtgcctt ccaggggccc gcgtaggcga tgccggcgac ctcgccgtcc acctcggcga    4200
cgagccaggg atagcgctcc cgcagacgga cgaggtcgtc cgtccactcc tgcggttcct    4260
gcggctcggt acggaagttg accgtgcttg tctcgatgta gtggttgacg atggtgcaga    4320
ccgccggcat gtccgcctcg gtggcacggc ggatgtcggc cgggcgtcgt tctgggtcca    4380
ttgttcttct ttactctttg tgtgactgag gtttggtcta gtgctttggt catctatata    4440
```

```
taatgataac aacaatgaga acaagctttg gagtgatcgg agggtctagg atacatgaga    4500
ttcaagtgga ctaggatcta caccgttgga ttttgagtgt ggatatgtgt gaggttaatt    4560
ttacttggta acggccacaa aggcctaagg agaggtgttg agacccttat cggcttgaac    4620
cgctggaata atgccacgtg aagataatt ccatgaatct tatcgttatc tatgagtgaa     4680
attgtgtgat ggtggagtgg tgcttgctca ttttacttgc ctggtggact tggcccttc     4740 cttatgggga atttatattt tacttactat agagctttca taccttttt ttaccttgga     4800 tttagttaat atataatggt atgattcatg aataaaaatg ggaatttttt gaatttgtac    4860
tgctaaatgc ataagattag gtgaaactgt ggaatatata ttttttcat ttaaaagcaa     4920 aatttgcctt ttactagaat tataaatata gaaaaatata taacattcaa ataaaaatga    4980
aaataagaac tttcaaaaaa cagaactatg tttaatgtgt aaagattagt cgcacatcaa    5040
gtcatctgtt acaatatgtt acaacaagtc ataagcccaa caaagttagc acgtctaaat    5100
aaactaaaga gtccacgaaa atattacaaa tcataagccc aacaaagtta ttgatcaaaa    5160
aaaaaaaacg cccaacaaag ctaaacaaag tccaaaaaaa acttctcaag tctccatctt    5220
cctttatgaa cattgaaaac tatacacaaa acaagtcaga taaatctctt tctgggcctg    5280
tcttcccaac ctcctacatc acttccctat cggattgaat gttttacttg tacctttcc    5340 gttgcaatga tattgatagt atgtttgtga aaactaatag ggttaacaat cgaagtcatg    5400
gaatatggat ttggtccaag attttccgag agctttctag tagaaagccc atcaccagaa    5460
atttactagt aaaataaatc accaattagg tttcttatta tgtgccaaat tcaatataat    5520
tatagaggat atttcaaatg aaaacgtatg aatgttatta gtaaatggtc aggtaagaca    5580
ttaaaaaaat cctacgtcag atattcaact ttaaaaattc gatcagtgtg gaattgtaca    5640
aaaatttggg atctactata tatatataat gctttacaac acttggatt tttttttggag    5700 gctggaattt ttaatctaca tatttgtttt ggccatgcac caactcattg tttagtgtaa    5760
tactttgatt ttgtcaaata tatgtgttcg tgtatatttg tataagaatt tctttgacca    5820
tatacacaca cacatatata tatatatata tatattat atcatgcact tttaattgaa      5880
aaaataatat atatatatat agtgcatttt ttctaacaac catatatgtt gcgattgatc    5940
tgcaaaaata ctgctagagt aatgaaaaat ataatctatt gctgaaatta tctcagatgt    6000
taagattttc ttaaagtaaa ttcttcaaa ttttagctaa aagtcttgta ataactaaag     6060
aataatacac aatctcgacc acggaaaaaa aacacataat aaatttgaat ttcgaccgcg    6120
gtacccggaa ttgggttata attacctcag gtcgaggaat taattcggta cgtacctaat    6180
aacttcgtat agcatacatt atacgaagtt atatggatct cgaggcatta cggcattacg    6240
gcactcgcga gggtcccaat tcgagcatgg agccatttac aattgaatat atcctgccgc    6300
cgctgccgct ttgcacccgg tggagcttgc atgttggttt ctacgcagaa ctgagccggt    6360
taggcagata atttccattg agaactgagc catgtgcacc ttcccccccaa cacggtgagc   6420 gacggggcaa cggagtgatc cacatgggac ttttaaacat catccgtcgg atggcgttgc    6480
gagagaagca gtcgatccgt gagatcagcc gacgcaccgg gcaggcgcgc aacacgatcg    6540
caaagtattt gaacgcaggt acaatcgagc cgacgttcac ggtaccggaa cgaccaagca    6600
agctagctta gtaaagccct cgctagattt taatgcggat gttgcgatta cttcgccaac    6660
tattgcgata acaagaaaaa gccagccttt catgatatat ctcccaattt gtgtagggct    6720
tattatgcac gcttaaaaat aataaaagca gacttgacct gatagtttgg ctgtgagcaa    6780
ttatgtgctt agtgcatcta acgcttgagt taagccgcgc cgcgaagcgg cgtcggcttg    6840
```

```
aacgaattgt tagacattat ttgccgacta ccttggtgat ctcgcctttc acgtagtgga   6900
caaattcttc caactgatct gcgcgcgagg ccaagcgatc ttcttcttgt ccaagataag   6960
cctgtctagc ttcaagtatg acgggctgat actgggccgg caggcgctcc attgcccagt   7020
cggcagcgac atccttcggc gcgattttgc cggttactgc gctgtaccaa atgcgggaca   7080
acgtaagcac tacatttcgc tcatcgccag cccagtcggg cggcgagttc catagcgtta   7140
aggtttcatt tagcgcctca aatagatcct gttcaggaac cggatcaaag agttcctccg   7200
ccgctggacc taccaaggca acgctatgtt ctcttgcttt tgtcagcaag atagccagat   7260
caatgtcgat cgtggctggc tcgaagatac ctgcaagaat gtcattgcgc tgccattctc   7320
caaattgcag ttcgcgctta gctggataac gccacggaat gatgtcgtcg tgcacaacaa   7380
tggtgacttc tacagcgcgg agaatctcgc tctctccagg ggaagccgaa gtttccaaaa   7440
ggtcgttgat caaagctcgc cgcgttgttt catcaagcct tacggtcacc gtaaccagca   7500
aatcaatatc actgtgtggc ttcaggccgc catccactgc ggagccgtac aaatgtacgg   7560
ccagcaacgt cggttcgaga tggcgctcga tgacgccaac tacctctgat agttgagtcg   7620
atacttcggc gatcaccgct tccctcatga tgtttaactt tgttttaggg cgactgccct   7680
gctgcgtaac atcgttgctg ctccataaca tcaaacatcg acccacggcg taacgcgctt   7740
gctgcttgga tgcccgaggc atagactgta ccccaaaaaa acagtcataa caagccatga   7800
aaaccgccac tgcgccgtta ccaccgctgc gttcggtcaa ggttctggac cagttgcgtg   7860
agcgcatacg ctacttgcat tacagcttac gaaccgaaca ggcttatgtc cactgggttc   7920
gtgccttcat ccgtttccac ggtgtgcgtc acccggcaac cttgggcagc agcgaagtcg   7980
aggcatttct gtcctggctg gcgaacgagc gcaaggtttc ggtctccacg catcgtcagg   8040
cattggcggc cttgctgttc ttctacggca agtgctgtgc acggatctgc cctggcttca   8100
ggagatcgga agacctcggc cgtccgggcg cttgccggtg gtgctgaccc cggatgaagt   8160
ctctagagct ctagagggtt cgcatcctcg gttttctgga aggcgagcat cgtttgttcg   8220
cccagcttct gtatggaacg ggcatgcgga tcagtgaggg tttgcaactg cgggtcaagg   8280
atctggattt cgatcacggc acgatcatcg tgcgggaggg caagggctcc aaggatcggg   8340
ccttgatgtt acccgagagc ttggcaccca gcctgcgcga gcaggatcg atccaacccc    8400
tccgctgcta tagtgcagtc ggcttctgac gttcagtgca gccgtcttct gaaaacgaca   8460
tgtcgcacaa gtcctaagtt acgcgacagg ctgccgccct gcccttttcc tggcgttttc   8520
ttgtcgcgtg ttttagtcgc ataaagtaga atacttgcga ctagaaccgg agacattacg   8580
ccatgaacaa gagcgccgcc gctggcctgc tgggctatgc ccgcgtcagc accgacgacc   8640
aggacttgac caaccaacgg gccgaactgc acgcggccgg ctgcaccaag ctgttttccg   8700
agaagatcac cggcaccagg cgcgaccgcc cggagctggc caggatgctt gaccacctac   8760
gccctggcga cgttgtgaca gtgaccaggc tagaccgcct ggcccgcagc acccgcgacc   8820
tactggacat tgccgagcgc atccaggagg ccggcgcggg cctgcgtagc ctggcagagc   8880
cgtgggccga caccaccacg ccggccggcc gcatggtgtt gaccgtgttc gccggcattg   8940
ccgagttcga gcgttcccta atcatcgacc gcacccggag cgggcgcgag gccgccaagg   9000
cccgaggcgt gaagtttggc cccgccccta ccctcacccc ggcacagatc gcgcacgccc   9060
gcgagctgat cgaccaggaa ggccgcaccg tgaaagaggc ggctgcactg cttggcgtgc   9120
atcgctcgac cctgtaccgc gcacttgagc gcagcgagga agtgacgccc accgaggcca   9180
```

-continued

```
ggcggcgcgg tgccttccgt gaggacgcat tgaccgaggc cgacgccctg gcggccgccg   9240
agaatgaacg ccaagaggaa caagcatgaa accgcaccag gacggccagg acgaaccgtt   9300
tttcattacc gaagagatcg aggcggagat gatcgcggcc gggtacgtgt tcgagccgcc   9360
cgcgcacgtc tcaaccgtgc ggctgcatga atcctggcc ggtttgtctg atgccaagct    9420
ggcggcctgg ccggccagct tggccgctga agaaaccgag cgccgccgtc taaaaaggtg   9480
atgtgtattt gagtaaaaca gcttgcgtca tgcggtcgct cgtatatga tgcgatgagt    9540 aaataaacaa atacgcaagg ggaacgcatg aaggttatcg ctgtacttaa ccagaaaggc   9600
gggtcaggca agacgaccat cgcaacccat ctagcccgcg ccctgcaact cgccggggcc   9660
gatgttctgt tagtcgattc cgatccccag ggcagtgccc gcgattgggc ggccgtgcgg   9720
gaagatcaac cgctaaccgt tgtcggcatc gaccgcccga cgattgaccg cgacgtgaag   9780
gccatcggcc ggcgcgactt cgtagtgatc gacggagcgc cccaggcggc ggacttggct   9840
gtgtccgcga tcaaggcagc cgacttcgtg ctgattccgg tgcagccaag cccttacgac   9900
atatgggcca ccgccgacct ggtggagctg gttaagcagc gcattgaggt cacggatgga   9960
aggctacaag cggcctttgt cgtgtcgcgg gcgatcaaag gcacgcgcat cggcggtgag   10020
gttgccgagg cgctggccgg gtacgagctg cccattcttg agtcccgtat cacgcagcgc   10080
gtgagctacc caggcactgc cgccgccggc acaaccgttc ttgaatcaga acccgagggc   10140
gacgctgccc gcgaggtcca ggcgctggcc gctgaaatta aatcaaaact catttgagtt   10200
aatgaggtaa agagaaaatg agcaaaagca caaacacgct aagtgccggc cgtccgagcg   10260
cacgcagcag caaggctgca acgttggcca gcctggcaga cacgccagcc atgaagcggg   10320
tcaactttca gttgccggcg gaggatcaca ccaagctgaa gatgtacgcg gtacgccaag   10380
gcaagaccat taccgagctg ctatctgaat acatcgcgca gctaccagag taaatgagca   10440
aatgaataaa tgagtagatg aattttagcg gctaaaggag gcggcatgga aaatcaagaa   10500
caaccaggca ccgacgccgt ggaatgcccc atgtgtggag gaacgggcgg ttggccaggc   10560
gtaagcggct gggttgtctg ccggccctgc aatggcactg gaaccccaa gcccgaggaa    10620 tcggcgtgac ggtcgcaaac catccggccc ggtacaaatc ggcgcggcgc tgggtgatga   10680
cctggtggag aagttgaagg ccgcgcaggc cgcccagcgg caacgcatcg aggcagaagc   10740
acgccccggt gaatcgtggc aagcggccgc tgatcgaatc cgcaaagaat cccggcaacc   10800
gccggcagcc ggtgcgccgt cgattaggaa gccgcccaag ggcgacgagc aaccagattt   10860
tttcgttccg atgctctatg acgtgggcac ccgcgatagt cgcagcatca tggacgtggc   10920
cgttttccgt ctgtcgaagc gtgaccgacg agctggcgag gtgatccgct acgagcttcc   10980
agacgggcac gtagaggttt ccgcagggcc ggccggcatg ccagtgtgt gggattacga    11040 cctggtactg atggcggttt cccatctaac cgaatccatg aaccgatacc gggaagggaa   11100
gggagacaag cccggccgcg tgttccgtcc acacgttgcg gacgtactca agttctgccg   11160
gcgagccgat ggcggaaagc agaaagacga cctggtagaa acctgcattc ggttaaacac   11220
cacgcacgtt gccatgcagc gtacgaagaa ggccaagaac ggccgcctgg tgacggtatc   11280
cgagggtgaa gccttgatta ccgctacaa gatcgtaaag agcgaaaccg gcggccgga    11340 gtacatcgag atcgagctag ctgattggat gtaccgcgag atcacagaag caagaaccc    11400 ggacgtgctg acggttcacc ccgattactt tttgatcgat cccggcatcg gccgttttct   11460
ctaccgcctg gcacgccgcg ccgcaggcaa ggcagaagcc agatggttgt tcaagacgat   11520
ctacgaacgc agtggcagcg ccggagagtt caagaagttc tgtttcaccg tgcgcaagct   11580
```

-continued

```
gatcgggtca aatgacctgc cggagtacga tttgaaggag gaggcggggc aggctggccc   11640
gatcctagtc atgcgctacc gcaacctgat cgagggcgaa gcatccgccg gttcctaatg   11700
tacggagcag atgctagggc aaattgccct agcaggggaa aaaggtcgaa aaggtctctt   11760
tcctgtggat agcacgtaca ttgggaaccc aaagccgtac attgggaacc ggaacccgta   11820
cattgggaac ccaaagccgt acattgggaa ccggtcacac atgtaagtga ctgatataaa   11880
agagaaaaaa ggcgattttt ccgcctaaaa ctctttaaaa cttattaaaa ctcttaaaac   11940
ccgcctggcc tgtgcataac tgtctggcca gcgcacagcc gaagagctgc aaaaagcgcc   12000 taccctttcgg tcgctgcgct ccctacgccc cgccgcttcg cgtcggccta tcgcggccgc   12060
tggccgctca aaaatggctg gcctacggcc aggcaatcta ccagggcgcg acaagccgc   12120 gccgtcgcca ctcgaccgcc ggcgcccaca tcaaggcacc ctgcctcgcg cgtttcggtg   12180
atgacggtga aaacctctga cacatgcagc tcccggagac ggtcacagct tgtctgtaag   12240
cggatgccgg gagcagacaa gcccgtcagg gcgcgtcagc gggtgttggc gggtgtcggg   12300
gcgcagccat gacccagtca cgtagcgata gcggagtgta tactggctta actatgcggc   12360
atcagagcag attgtactga gagtgcacca tatgcggtgt gaaataccgc acagatgcgt   12420
aaggagaaaa taccgcatca ggcgctcttc cgcttcctcg ctcactgact cgctgcgctc   12480
ggtcgttcgg ctgcggcgag cggtatcagc tcactcaaag gcggtaatac ggttatccac   12540
agaatcaggg gataacgcag gaaagaacat gtgagcaaaa ggccagcaaa aggccaggaa   12600
ccgtaaaaag gccgcgttgc tggcgttttt ccataggctc cgcccccctg acgagcatca   12660
caaaaatcga cgctcaagtc agaggtggcg aaacccgaca ggactataaa gataccaggc   12720
gtttccccct ggaagctccc tcgtgcgctc tcctgttccg accctgccgc ttaccggata   12780
cctgtccgcc tttctccctt cgggaagcgt ggcgctttct catagctcac gctgtaggta   12840
tctcagttcg gtgtaggtcg ttcgctccaa gctgggctgt gtgcacgaac cccccgttca   12900
gcccgaccgc tgcgccttat ccggtaacta tcgtcttgag tccaacccgg taagacacga   12960
cttatcgcca ctggcagcag ccactggtaa caggattagc agagcgaggt atgtaggcgg   13020
tgctacagag ttcttgaagt ggtggcctaa ctacggctac actagaagga cagtatttgg   13080
tatctgcgct ctgctgaagc cagttacctt cggaaaaaga gttggtagct cttgatccgg   13140
caaacaaacc accgctggta gcggtggttt ttttgtttgc aagcagcaga ttacgcgcag   13200
aaaaaaagga tctcaagaag atccggaaaa cgcaagcgca aagagaaagc aggtagcttg   13260
cagtgggctt acatggcgat agctagactg gcggttttta tggacagcaa gcgaaccgga   13320
attgcc                                                              13326
```